United States Patent
Takayama et al.

(10) Patent No.: US 8,461,329 B2
(45) Date of Patent: Jun. 11, 2013

(54) ISOQUINOLINE DERIVATIVE

(75) Inventors: Tetsuo Takayama, Tokyo (JP); Hajime Asanuma, Tokyo (JP); Daisuke Wakasugi, Tokyo (JP); Rie Nishikawa, Tokyo (JP); Yoshinori Sekiguchi, Tokyo (JP); Madoka Kawamura, Tokyo (JP); Naoya Ono, Tokyo (JP); Tetsuya Yabuuchi, Tokyo (JP); Takahiro Oi, Tokyo (JP); Yusuke Oka, Tokyo (JP); Shoichi Kuroda, Tokyo (JP); Fumito Uneuchi, Tokyo (JP); Takeshi Koami, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 77 days.

(21) Appl. No.: 13/142,230

(22) PCT Filed: Dec. 25, 2009

(86) PCT No.: PCT/JP2009/071633
§ 371 (c)(1),
(2), (4) Date: Aug. 15, 2011

(87) PCT Pub. No.: WO2010/074244
PCT Pub. Date: Jul. 1, 2010

(65) Prior Publication Data
US 2011/0288293 A1 Nov. 24, 2011

(30) Foreign Application Priority Data
Dec. 25, 2008 (JP) ................................ 2008-329064

(51) Int. Cl.
C07D 413/12 (2006.01)
C07D 401/12 (2006.01)
C07D 405/12 (2006.01)
C07D 217/24 (2006.01)

(52) U.S. Cl.
USPC ........... 544/128; 544/238; 544/333; 544/353; 544/355; 544/405; 546/113; 546/121; 546/122; 546/140; 546/141; 546/146; 546/147

(58) Field of Classification Search
None
See application file for complete search history.

(56) References Cited

U.S. PATENT DOCUMENTS

2004/0259910 A1 12/2004 Bolin et al.
2006/0264444 A1 11/2006 Bonnert et al.
2007/0129355 A1 6/2007 Ly et al.

FOREIGN PATENT DOCUMENTS

| JP | 2006-524645 A | 11/2006 |
|---|---|---|
| JP | 2006-528218 A | 12/2006 |
| JP | 2007-502804 A | 2/2007 |
| WO | 2004/096777 A1 | 11/2004 |
| WO | 2004/101528 A2 | 11/2004 |
| WO | 2005/019171 A1 | 3/2005 |
| WO | 2005/115382 A1 | 8/2005 |
| WO | 2005/115382 A1 | 12/2005 |

OTHER PUBLICATIONS

Supplementary Extended European Search report dated May 22, 2012, issued in corresponding European Patent Application No. 09835040.8.
Database Registry [Online], Chemical Abstracts Service, Columbus, OH, US; Jun. 11, 2008; XP002675593.
Kinya Nagata, et al., "Selective Expression of a Novel Surface Molecule by Human Th2 Cells In Vivo", The Journal of Immunology, Feb. 1999, 2 pages, vol. 162, No. 3.
Del Prete G., "Human Th1 and Th2 lymphocytes: their role in the pathophysiology of atopy", Allergy, Basic Review Article, 1992, pp. 450-455, vol. 47.
Samuel M. Pope, et al., "IL-13 induces eosinophil recruitment into the lung by an IL-5- and eotaxin-dependent mechanism", The Journal of Allergy and Clinical Immunology, Oct. 2001, p. 594, vol. 108, No. 4.
Booki Min, et al., "Basophils and type 2 immunity", Current Opinion in Hematology, 2008, pp. 59-63, vol. 15.
David H. Broide, MD, "Molecular and cellular mechanisms of allergic disease", The Journal of Allergy and Clinical Immunology, Aug. 2001, p. S65-71, vol. 108, No. 2.
Hiroyuki Abe, et al., "Molecular cloning, chromosome mapping and characterization of the mouse CRTH2 gene, a putative member of the leukocyte chemoattractant receptor family", Gene, 1999, pp. 71-77, vol. 227.
Hiroyuki Hirai, et al., Prostaglandin D2 Selectively Induces Chemotaxis in T Helper Type 2 Cells, Eosinophils, and Basophils via Seven-Transmembrane Receptor CRTH2, The Journal of Experimental Medicine, Jan. 2001, 255-261, vol. 193, No. 2.
Yoshiki Shiraishi, et al., "Prostaglandin $D_2$-Induced Eosinophilic Airway Inflammation Is Mediated by CRTH2 Receptor", The Journal of Pharmacology and Experimental Therapeutics, Mar. 2005, pp. 954-960, vol. 312, No. 3.
Takahiro Satoh, et al., "Prostaglandin $D_2$ Plays an Essential Role in Chronic Allergic Inflammation of the Skin via CRTH2 Receptor", The Journal of Immunology, Aug. 2006, pp. 2621-2629, vol. 177, No. 4.
Mitsuhiro Okano, et al., "Presence and characterization of prostaglandin D2-related molecules in nasal mucosa of patients with allergic rhinitis", American Journal of Rhinol., May-Jun. 2006, pp. 342-348, vol. 20, No. 3.
International Search Report of PCT/JP2009/071633, dated Feb. 2, 2010.

*Primary Examiner* — Zinna Northington Davis
(74) *Attorney, Agent, or Firm* — Sughrue Mion, PLLC

(57) ABSTRACT

A compound represented by formula (I) or a pharmaceutically acceptable salt thereof has an effect of inhibiting CRTH2 and, therefore, is useful as a preventive or a remedy for allergic diseases such as asthma, atopic dermatitis and allergic rhinitis.

14 Claims, No Drawings

ISOQUINOLINE DERIVATIVE

CROSS REFERENCE TO RELATED APPLICATIONS

This application is a National Stage of International Application No. PCT/JP2009/071633, filed Dec. 25, 2009, which claims priority from Japanese Patent Application No. 2008-329064, filed Dec. 25, 2008, the contents of all of which are incorporated herein by reference in their entirety.

TECHNICAL FIELD

The present invention relates to a compound having an inhibitory effect on CRTH2 (Chemoattractant Receptor-homologous molecule expressed on Th2 cells), and pharmaceutical preparations containing the compound as an active ingredient.

BACKGROUND ART

CRTH2 is a G-protein coupled 7th transmembrane domain molecule cloned by Nagata et al. in 1999 as a molecule expressed selectively on Th2 cells (see Non Patent Document 1).

It has been reported that the Th2 cell is one form of activated T cells and induces production of IgE from B cells via production of cytokines such as IL-4, IL-5, and IL-13 (see Non Patent Document 2). Furthermore, it has been reported that the cytokines induce the activation of eosinophil and basophil (see Non Patent Documents 3 and 4). From the above reports, it has been believed that the Th2 cells are strongly involved in the formation of pathologic conditions of allergic diseases such as asthma, allergic rhinitis, and atopic dermatitis directly or indirectly via other cells or factors (see Non Patent Document 5).

Because CRTH2 is cloned as a molecule expressed selectively on the Th2 cell as mentioned above, and also, it has relatively high homology to a chemokine receptor (see Non Patent Document 6), it has been assumed that CRTH2 is involved in immune responses or immune-related disorders. Thereafter, it has been revealed that CRTH2 is expressed in eosinophil and basophil in addition to the Th2 cell, and that the ligand is PGD2 and the action thereof induces a cell migration reaction and the like (see Non Patent Document 7). In particular, it has been suggested that CRTH2 is involved in allergic diseases.

In addition to such in vitro tests, in exacerbation of symptoms in an asthma model by a CRTH2-specific ligand and in a dermatitis model (see Non Patent Document 8), suppression of symptoms in dermatitis in a CRTH2 defective mouse (see Non Patent Document 9), increase in expression of CRTH2 in human patients with allergic rhinitis (Non Patent Document 10), and the like, the possibility that CRTH2 is involved in allergic diseases such as asthma, atopic dermatitis, and allergic rhinitis has been reported. From such information, the possibility of creation of therapeutic agents for the above-mentioned diseases, which have a mechanism of inhibiting CRTH2, has been suggested.

Conventionally, as CRTH2 inhibitors, indolyl acetic acid derivatives (see Patent Document 1), phenoxy acetic acid derivatives (see Patent Document 2), pyrimidinyl acetic acid derivative (see Patent Document 3) and the like have been reported. However, a compound having the structure of the present invention has not been disclosed. Furthermore, although a compound of which the structure is similar to that of the compound of the present invention has been reported, there is neither description nor suggestion that such compounds have a CRTH2 inhibitory effect (see Patent Document 4).

PRIOR ART DOCUMENT

Patent Document

Patent Document 1: WO2005/019171
Patent Document 2: WO2005/115382
Patent Document 3: WO2004/096777
Patent Document 4: WO2004/101528

Non Patent Document

Non Patent Document 1: Nagata. et al. J. Immunol. 162. 1278. 1999
Non Patent Document 2: Del Prete. et al. Allergy. 47. 450. 1992
Non Patent Document 3: Pope. et al. J. Allergy. Clin. Immunol. 108. 594. 2001
Non Patent Document 4: Min. et al. Curr. Opin. Hematol. 15. 59. 2008
Non Patent Document 5: Broide. et al. J. Allergy. Clin. Immunol. 108 (2 suppl.). S65.2001
Non Patent Document 6: Abe. et al. Gene. 227. 71. 1999
Non Patent Document 7: Hirai. et al. J. Exp. Med. 193. 225. 2001
Non Patent Document 8: Shiraishi. et al. J. Pharmacol. Exp. Ther. 312. 954. 2005
Non Patent Document 9: Satoh. et al. J. Immunol. 177. 2621. 2006
Non Patent Document 10: Kano. et al. Am. J. Rhinol. 20. 342. 2006

SUMMARY OF INVENTION

Problem to be Solved by the Invention

An object of the present invention is to provide a compound having an inhibitory effect on CRTH2 and being useful as pharmaceutical preparations.

Means for Solving the Problem

The present inventors have keenly carried out investigations for achieving the above-mentioned objects, and resulted in finding that novel isoquinoline derivatives achieve the above-mentioned object and have arrived at the present invention.

That is to say, the present invention is (1) a compound represented by formula (I):

[Ka 1]

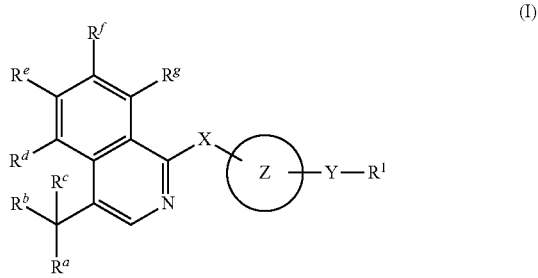

or a pharmaceutically acceptable salt thereof.

In the formula, $R^1$ represents a $C_{1-6}$ alkyl group, a $C_{2-6}$ alkenyl group, a $C_{3-6}$ cycloalkyl group, a $C_{3-6}$ cycloalkenyl group, an adamantyl group, an indanyl group, a tetrahydronaphthyl group, a tetrahydroindolyl group, a tetrahydropyranyl group, a morpholinyl group, a phenyl group, a naphthyl group, or an aromatic heterocyclic group, wherein the phenyl group, the naphthyl group, and the aromatic heterocyclic group may be substituted with 1 to 5 substituent(s) selected from the group consisting of a $C_{1-6}$ alkyl group, a $C_{2-6}$ alkenyl group, a $C_{3-6}$ cycloalkyl group, a halogen atom, a $C_{1-6}$ alkoxy group, a hydroxy group, a $C_{1-6}$ alkylthio group, a $C_{1-6}$ haloalkyl group, a $C_{1-6}$ haloalkoxy group, a $C_{1-6}$ haloalkylthio group, a cyano group, a nitro group, a guanidino group, a $C_{1-6}$ alkylsulfonyl group, a carboxy group, a $C_{2-7}$ alkoxycarbonyl group, a $C_{2-7}$ alkanoyloxy group, a phenyl group, a benzoyl group, a phenoxy group, a pyrrolyl group, a thienyl group, an imidazolyl group, a thiadiazolyl group, a morpholino group, the formula: —$NR^5R^6$, the formula: —$SO_2NR^7R^8$, the formula: —$NR^9SO_2R^{10}$, the formula: —$CONR^{11}R^{12}$, and the formula: —$NR^{13}COR^{14}$, wherein $R^5$, $R^6$, $R^7$, $R^8$, $R^9$, $R^{10}$, $R^{11}$, $R^{12}$, $R^{13}$, and $R^{14}$ each independently represent a hydrogen atom or a $C_{1-6}$ alkyl group;

X represents an oxygen atom, a sulfur atom, the formula: —$CH_2$—, the formula: —CO—, or the formula: —$NR^2$—, wherein $R^2$ represents a hydrogen atom or a $C_{1-6}$ alkyl group;

Y represents a single bond, the formula: —$NR^3CO$—W—, the formula: —$NR^3CO$—W—O—, the formula: —$NR^3CO_2$—W—, the formula: —$NR^3$—W—, the formula: —$NR^3SO_2$—W—, the formula: —$NR^3CONR^4$—W—, the formula: —$NR^3CO$—W—$NR^4SO_2$—, the formula: —$SO_2NR^3$—W—, the formula: —$CH_2$—W—, the formula: —$CONR^3$—W—, the formula: —$CONR^3$—W—O—, the formula: —$CH_2$—O—W—, the formula: —$CH_2NR^3$—W—, the formula: —$CONR^3$—W—$NR^4CO$—, the formula: —O—W—, or the formula: —O—W—O—, wherein $R^3$ and $R^4$ each independently represent a hydrogen atom or a $C_{1-6}$ alkyl group, W is a single bond, a $C_{1-6}$ alkylene group, a $C_{2-6}$ alkylene group including a carbon atom that is also a member of a $C_{3-6}$ cycloalkyl ring, a $C_{2-6}$ alkenylene group, or a $C_{3-6}$ cycloalkylene group (provided that, when Y is the formula: —$CONR^3$—W—$NR^4CO$— or the formula: —O—W—O—, W is not a single bond);

Z is a benzene ring, a pyrimidine ring, or a pyrazine ring;

$R^a$ is a carboxy group, a carbamoyl group, a tetrazolyl group, or the formula: —CONHOH;

$R^b$ and $R^c$ each independently represent a hydrogen atom, a halogen atom, or a $C_{1-6}$ alkyl group; and $R^d$, $R^e$, $R^f$ and $R^g$ each independently represent a hydrogen atom, a halogen atom, a $C_{1-6}$ alkyl group, or a $C_{1-6}$ alkoxy group (provided that the compound is not {1-[3-(butan-2-yloxy)benzyl]6,7-dimethoxyisoquinolin-4-yl}acetic acid, (1-{[3-(butan-2-yl)phenyl]carbonyl}-6,7-dimethoxyisoquinolin-4-yl)acetic acid, (1-{[3-(butan-2-yloxy)phenyl]carbonyl}-6,7-dimethoxyisoquinolin-4-yl)acetic acid, 2-(6,7-dimethoxy-1-{[3-(propan-2-yloxy)phenyl]carbonyl}isoquinolin-4-yl)acetamide, (6,7-dimethoxy-1-{[3-(propan-2-yloxy)phenyl]carbonyl}isoquinolin-4-yl)acetic acid, 2-{6,7-dimethoxy-1-[(3-methoxyphenyl)carbonyl]isoquinolin-4-yl}acetamide, or {6,7-dimethoxy-1-[(3-methoxyphenyl)carbonyl] isoquinolin-4-yl}acetic acid).

(2) The compound or a pharmaceutically acceptable salt thereof as stated in (1), wherein $R^d$, $R^e$, $R^f$ and $R^g$ each independently represent a hydrogen atom, a halogen atom, a $C_{1-6}$ alkyl group, or a $C_{1-6}$ alkoxy group (except the compound or a pharmaceutically acceptable salt thereof in which both $R^d$ and $R^g$ are hydrogen atoms and both $R^e$ and $R^f$ are $C_{1-6}$ alkoxy groups).

(3) The compound or a pharmaceutically acceptable salt thereof as stated in (1) or (2), wherein $R^1$ is a $C_{1-6}$ alkyl group, a $C_{2-6}$ alkenyl group, a $C_{3-6}$ cycloalkyl group, a $C_{3-6}$ cycloalkenyl group, an adamantyl group, an indanyl group, a tetrahydronaphthyl group, a tetrahydroindolyl group, a tetrahydropyranyl group, a morpholinyl group, a phenyl group, a naphthyl group, or an aromatic heterocyclic group, wherein the phenyl group, the naphthyl group, and the aromatic heterocyclic group may be substituted with 1 to 5 substituent(s) selected from the group consisting of a $C_{1-6}$ alkyl group, a $C_{2-6}$ alkenyl group, a $C_{3-6}$ cycloalkyl group, a halogen atom, a $C_{1-6}$ alkoxy group, a hydroxy group, a $C_{1-6}$ haloalkyl group, a $C_{1-6}$ haloalkoxy group, a cyano group, a nitro group, a $C_{1-6}$ alkylsulfonyl group, a carboxy group, a phenyl group, a benzoyl group, a phenoxy group, the formula: —$NR^5R^6$, and the formula: —$SO_2NR^7R^8$;

X is an oxygen atom, the formula: —$CH_2$—, or the formula: —CO—;

Z is a benzene ring;

$R^a$ is a carboxy group, a carbamoyl group, a tetrazolyl group, or the formula: —CONHOH;

$R^b$ and $R^c$ each independently represent a hydrogen atom, or a $C_{1-6}$ alkyl group; and $R^d$, $R^e$, $R^f$ and $R^g$ each independently represent a hydrogen atom, a halogen atom, or a $C_{1-6}$ alkoxy group.

(4) The compound or a pharmaceutically acceptable salt thereof as stated in (1), wherein $R^1$ is a $C_{1-6}$ alkyl group, a $C_{3-6}$ cycloalkyl group, a phenyl group, a naphthyl group, or an aromatic heterocyclic group, wherein the phenyl group, the naphthyl group, and the aromatic heterocyclic group may be substituted with 1 to 3 substituent(s) selected from the group consisting of a $C_{1-6}$ alkyl group, a halogen atom, a $C_{1-6}$ alkoxy group, a hydroxy group, a $C_{1-6}$ alkylthio group, a $C_{1-6}$ haloalkyl group, a $C_{1-6}$ haloalkoxy group, a $C_{1-6}$ haloalkylthio group, a cyano group, a nitro group, a guanidino group, a $C_{1-6}$ alkylsulfonyl group, a carboxy group, a $C_{2-7}$ alkoxycarbonyl group, a $C_{2-7}$ alkanoyloxy group, a phenyl group, a phenoxy group, a pyrrolyl group, a thienyl group, an imidazolyl group, a thiadiazolyl group, a morpholino group, the formula: —$NR^5R^6$, the formula: —$SO_2NR^7R^8$, the formula: —$NR^9SO_2R^{10}$, the formula: —$CONR^{11}R^{12}$, and the formula: —$NR^{13}COR^{14}$;

Y is a single bond, the formula: —$NR^3CO$—W—, the formula: —$NR^3CO$—W—O—, the formula: —$NR^3CO_2$—W—, the formula: —$NR^3$—W—, the formula: —$NR^3SO_2$—W—, the formula: —$NR^3CONR^4$—W—, the formula: —$CONR^3$—W—, the formula: —O—W—, the formula: —$CH_2O$—, or the formula: —$CH_2NR^3$—;

W is a single bond, a $C_{1-6}$ alkylene group, a $C_{2-6}$ alkenylene group, or a $C_{3-6}$ cycloalkylene group;

$R^a$ is a carboxy group;

$R^b$ and $R^c$ are each a hydrogen atom, and $R^d$, $R^e$, $R^f$ and $R^g$ are each a hydrogen atom.

(5) The compound or a pharmaceutically acceptable salt thereof as stated in (1), wherein $R^1$ is a $C_{1-6}$ alkyl group, a $C_{3-6}$ cycloalkyl group, a phenyl group, a naphthyl group, or an aromatic heterocyclic group, wherein the phenyl group, the naphthyl group, and the aromatic heterocyclic group may be substituted with 1 to 3 substituent(s) selected from the group consisting of a $C_{1-6}$ alkyl group, a halogen atom, a $C_{1-6}$ alkoxy group, a $C_{1-6}$ haloalkyl group, a $C_{1-6}$ haloalkoxy group, a cyano group, a nitro group, a phenyl group, a phenoxy group, and the formula: —$NR^5R^6$;

X is the formula: —$CH_2$—, or the formula: —CO—;

Y is the formula: —$NR^3CO$—W—, the formula: —$NR^3CO$—W—O—, the formula: —$NR^3CO_2$—W—, the formula: —$NR^3$—W—, the formula: —$NR^3SO_2$—W—, the formula: —$NR^3CONR^4$—W—, or the formula: —O—W—;

W is a single bond, a $C_{1-6}$ alkylene group, a $C_{2-6}$ alkenylene group, or a $C_{3-6}$ cycloalkylene group;

Z is a benzene ring;

$R^a$ is a carboxy group;

$R^b$ and $R^c$ are each a hydrogen atom, and $R^d$, $R^e$, $R^f$ and $R^g$ are each a hydrogen atom.

(6) The compound or a pharmaceutically acceptable salt thereof as stated in (1), which is represented by formula (II):

[Ka 2]

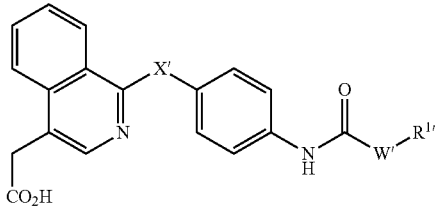

(II)

In the formula, $R^{1\prime}$ is a $C_{3-6}$ cycloalkyl group, a $C_{3-6}$ cycloalkenyl group, an adamantyl group, an indanyl group, a tetrahydronaphthyl group, a tetrahydroindolyl group, a phenyl group, a naphthyl group, or an aromatic heterocyclic group, wherein the phenyl group, the naphthyl group, and the aromatic heterocyclic group may be substituted with 1 to 5 substituent(s) selected from the group consisting of a $C_{1-6}$ alkyl group, a $C_{2-6}$ alkenyl group, a $C_{3-6}$ cycloalkyl group, a halogen atom, a $C_{1-6}$ alkoxy group, a hydroxy group, a $C_{1-6}$ haloalkyl group, a $C_{1-6}$ haloalkoxy group, a cyano group, a nitro group, a $C_{1-6}$ alkylsulfonyl group, a phenyl group, a benzoyl group, a phenoxy group, the formula: —$NR^5R^6$, and the formula: —$SO_2NR^7R^8$, wherein $R^5$, $R^6$, $R^7$, and $R^8$ each independently represent a hydrogen atom or a $C_{1-6}$ alkyl group;

X' is the formula: —$CH_2$—, or the formula: —CO—; and

W' is a single bond, a $C_{1-6}$ alkylene group, a $C_{2-6}$ alkenylene group, or a $C_{3-6}$ cycloalkylene group.

(7) The compound or a pharmaceutically acceptable salt thereof as stated in (6), wherein $R^{1\prime}$ is a $C_{3-6}$ cycloalkyl group, a tetrahydronaphthyl group, a tetrahydroindolyl group, a phenyl group, a naphthyl group, an indolyl group, a benzofuranyl group, a benzothienyl group, a quinolyl group, or an isoquinolyl group, wherein the phenyl group, the naphthyl group, the indolyl group, the benzofuranyl group, the benzothienyl group, the quinolyl group, or the isoquinolyl group may be substituted with 1 to 3 substituent(s) selected from the group consisting of a $C_{1-6}$ alkyl group, a halogen atom, a $C_{1-6}$ alkoxy group, a $C_{1-6}$ haloalkyl group, a $C_{1-6}$ haloalkoxy group, a cyano group, a nitro group, a phenyl group, a phenoxy group, and the formula: —$NR^5R^6$.

(8) The compound or a pharmaceutically acceptable salt thereof as stated in (6), wherein $R^{1\prime}$ is a phenyl group, which may be substituted with 1 to 3 substituent(s) selected from the group consisting of a $C_{1-6}$ alkyl group, a halogen atom, a $C_{1-6}$ alkoxy group, a $C_{1-6}$ haloalkyl group, a $C_{1-6}$ haloalkoxy group, a cyano group, a nitro group, a phenyl group, a phenoxy group, and the formula: —$NR^5R^6$; and W' is a single bond.

(9) The compound or a pharmaceutically acceptable salt thereof as stated in any one of (6) to (8), wherein X' is the formula: —$CH_2$—.

(10) The compound or a pharmaceutically acceptable salt thereof as stated in (8), wherein X' is the formula: —CO—.

(11) The compound or a pharmaceutically acceptable salt thereof as stated in (1) which is represented by formula (III):

[Ka 3]

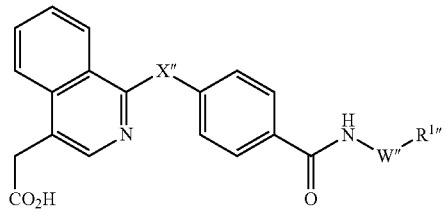

(III)

In the formula, $R^{1\prime\prime}$ is a $C_{3-6}$ cycloalkyl group, a $C_{3-6}$ cycloalkenyl group, an adamantyl group, a tetrahydronaphthyl group, a tetrahydroindolyl group, a phenyl group, a naphthyl group, or an aromatic heterocyclic group, wherein the phenyl group, the naphthyl group, and the aromatic heterocyclic group may be substituted with 1 to 5 substituent(s) selected from the group consisting of a $C_{1-6}$ alkyl group, a $C_{3-6}$ cycloalkyl group, a halogen atom, a $C_{1-6}$ alkoxy group, a hydroxy group, a $C_{1-6}$ haloalkyl group, a $C_{1-6}$ haloalkoxy group, a cyano group, a nitro group, a phenyl group, a phenoxy group, and the formula: —$NR^5R^6$;

$R^5$ and $R^6$ each independently represent a hydrogen atom or a $C_{1-6}$ alkyl group;

X" is the formula: —$CH_2$—, or the formula: —CO—; and

W" is a single bond, a $C_{2-6}$ alkylene group including a carbon atom that is also a member of a $C_{3-6}$ cycloalkyl ring, or a $C_{1-6}$ alkylene group.

(12) The compound or a pharmaceutically acceptable salt thereof as stated in (11), $R^{1\prime\prime}$ is a $C_{3-6}$ cycloalkyl group, an adamantyl group, a tetrahydronaphthyl group, a phenyl group, a naphthyl group, an indolyl group, a benzothiazolyl group, a benzofuranyl group, or a benzothienyl group, wherein the phenyl group, the naphthyl group, the indolyl group, benzothiazolyl group, the benzofuranyl group, and the benzothienyl group may be substituted with 1 to 3 substituent(s) selected from the group consisting of a $C_{1-6}$ alkyl group, a $C_{3-6}$ cycloalkyl group, a halogen atom, a $C_{1-6}$ alkoxy group, a $C_{1-6}$ haloalkyl group, a $C_{1-6}$ haloalkoxy group, a phenyl group, and a phenoxy group.

(13) The compound or a pharmaceutically acceptable salt thereof as stated in (11) or (12), wherein X" is the formula: —$CH_2$—.

(14) The compound or a pharmaceutically acceptable salt thereof as stated in any one of (11) to (13), wherein W" is a $C_{1-6}$ alkylene group.

(15) A preventive agent or a therapeutic agent for allergic diseases such as asthma, atopic dermatitis, and allergic rhinitis including a compound or a pharmaceutically acceptable salt thereof as stated in any one of the above-mentioned (1) to (14) as an active ingredient.

Advantageous Effects of the Invention

The compound of the present invention has an inhibitory effect on CRTH2.

MODE FOR CARRYING OUT THE INVENTION

In the present invention, the $C_{1-6}$ alkyl group refers to a linear or branched alkyl group having 1 to 6 carbon atoms, and examples thereof include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, and a n-hexyl group.

The $C_{2-6}$ alkenyl group refers to a linear or branched alkenyl group having 2 to 6 carbon atoms, and examples thereof include a vinyl group, an allyl group, a 1-propenyl group, an isopropenyl group, a 1-butenyl group, a 2-butenyl group, a 3-butenyl group, a 1-pentenyl group, a 2-pentenyl group, a 1-hexenyl group, and a 1,3-butadienyl group.

The $C_{1-6}$ alkylene group refers to a linear or branched alkylene group having 1 to 6 carbon atoms, and examples thereof include a methylene group, an ethylene group, a trimethylene group, a tetramethylene group, a pentamethylene group, a hexamethylene group, an ethylidene group, a dimethyl methylene group, and a methyl ethylene group.

Examples of the $C_{2-6}$ alkylene group including a carbon atom that is also a member of a $C_{3-6}$ cycloalkyl ring include a 1,1-ethylene ethylene group, a 1,1-trimethylene ethylene group, a 1,1-tetramethylene ethylene group, a 1,1-pentamethylene ethylene group, a 1,1-ethylene trimethylene group, and a 2,2-ethylene trimethylene group. Each of the above-mentioned groups is shown below.

[Ka 4]

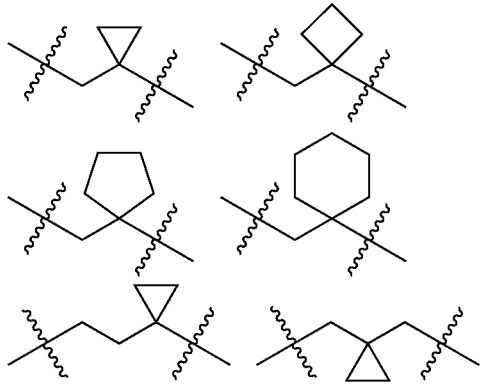

The $C_{2-6}$ alkenylene group refers to a linear or branched alkenylene group having 2 to 6 carbon atoms, and examples thereof include an ethenylene group, a propenylene group, and a methylethenylene group.

The $C_{3-6}$ cycloalkyl group refers to a cyclopropyl group, a cyclobutyl group, a cyclopentyl group, and a cyclohexyl group.

The $C_{3-6}$ cycloalkenyl group refers to a cycloalkenyl group having 3 to 6 carbon atoms, and examples thereof include a cyclobutenyl group, a cyclopentenyl group, a cyclohexenyl group, a cyclopentadienyl group, and a cyclohexadienyl group.

The $C_{3-6}$ cycloalkylene group refers to a cycloalkylene group having 3 to 6 carbon atoms, and examples thereof include a cyclopropane-1,1-diyl group, a cyclobutane-1,1-diyl group, a cyclopentane-1,1-diyl group, a cyclohexane-1,1-diyl group, and a cyclohexane-1,4-diyl group.

The aromatic heterocyclic group refers to a monocyclic aromatic heterocyclic group or a condensed ring aromatic heterocyclic group including one or two heteroatom(s) selected from an oxygen atom, a nitrogen atom, and a sulfur atom in its ring, and examples thereof include a pyridyl group, a pyrimidyl group, a pyridazyl group, a pyrazinyl group, an oxazolyl group, a thiazolyl group, an isoxazolyl group, an isothiazolyl group, an indolyl group, a benzofuranyl group, a benzothienyl group, an imidazolyl group, a thienyl group, a furyl group, a pyrazolyl group, a pyrrolyl group, a quinoxalyl group, a quinolyl group, an isoquinolyl group, a quinazolyl group, a cinnolinyl group, a pyrrolopyridyl group, a naphthyridyl group, an imidazopyridyl group, an indazolyl group, a benzothiazolyl group, a benzoimidazolyl group, and a benzooxazolyl group.

The halogen atom refers to a fluorine atom, a chlorine atom, a bromine atom, and an iodine atom.

The $C_{1-6}$ alkoxy group refers to a linear or branched alkoxy group having 1 to 6 carbon atoms, and examples thereof include a methoxy group, an ethoxy group, a n-propoxy group, an isopropoxy group, a n-butoxy group, an isobutoxy group, a tert-butoxy group, a sec-butoxy group, a n-pentyloxy group, an isopentyloxy group, a neopentyloxy group, a tert-pentyloxy group, and a n-hexyloxy group.

The $C_{1-6}$ alkylthio group refers to a linear or branched alkylthio group having 1 to 6 carbon atoms, and examples thereof include a methylthio group, an ethylthio group, a n-propylthio group, an isopropylthio group, a n-butylthio group, an isobutylthio group, a tert-butylthio group, a sec-butylthio group, a n-pentylthio group, an isopentylthio group, a neopentylthio group, a tert-pentylthio group, and a n-hexylthio group.

The $C_{1-6}$ haloalkyl group refers to a linear or branched alkyl group having 1 to 6 carbon atoms, substituted with halogen atoms, in which the preferable number of halogen atoms is 3 to 5. Examples thereof include a trifluoromethyl group and a pentafluoroethyl group.

The $C_{1-6}$ haloalkylthio group refers to a linear or branched alkylthio group having 1 to 6 carbon atoms, substituted with halogen atoms, in which the preferable number of halogen atoms is 3 to 5. Examples thereof include a trifluoromethylthio group and a pentafluoroethylthio group.

The $C_{1-6}$ haloalkoxy group refers to a linear or branched alkoxy group having 1 to 6 carbon atoms, substituted with halogen atoms, in which the preferable number of halogen atoms is 3 to 5. Examples thereof include a trifluoromethoxy group and a pentafluoroethoxy group.

The $C_{1-6}$ alkylsulfonyl group refers to a linear or branched alkylsulfonyl group having 1 to 6 carbon atoms, and examples thereof include a methylsulfonyl group, an ethylsulfonyl group, a n-propylsulfonyl group, an isopropylsulfonyl group, a n-butylsulfonyl group, an isobutylsulfonyl group, a tert-butylsulfonyl group, a sec-butylsulfonyl group, a n-pentylsulfonyl group, an isopentylsulfonyl group, a neopentylsulfonyl group, a tert-pentylsulfonyl group, and a n-hexylsulfonyl group.

The $C_{2-7}$ alkoxycarbonyl group refers to a linear or branched alkoxycarbonyl group having 2 to 7 carbon atoms, and examples thereof include a methoxycarbonyl group, an ethoxycarbonyl group, a n-propoxycarbonyl group, an isopropoxycarbonyl group, a n-butoxycarbonyl group, an isobutoxycarbonyl group, a tert-butoxycarbonyl group, a sec-butoxycarbonyl group, a n-pentyloxycarbonyl group, an isopentyloxycarbonyl group, a neopentyloxycarbonyl group, a tert-pentyloxycarbonyl group, and a n-hexyloxycarbonyl group.

The $C_{2-7}$ alkanoyloxy group refers to a linear or branched alkanoyloxy group having 2 to 7 carbon atoms, and examples thereof include an acetoxy group, propanoyloxy group, a n-butanoyloxy group, and an isobutyroyloxy group.

The pharmaceutically-acceptable salt refers to a salt with an alkali metal, an alkali earth metal, ammonium, alkylammonium, or the like, or a salt with a mineral acid or an organic acid. Examples thereof include sodium salts, potassium salts, calcium salts, ammonium salts, aluminum salts, triethylammonium salts, acetates, propionates, butyrates, formates, trifluoroacetates, maleates, tartarates, citrates, stearates, succinates, ethylsuccinates, lactobionates, gluconates, glucoheptonates, benzoates, methanesulfonates, ethanesulfonates, 2-hydroxyethanesulfonates, benzenesulfonates, para-toluenesulfonates, laurylsulfates, malates, aspartates, glutamates, adipates, salts with cysteine, salts with N-acetylcysteines, hydrochlorides, hydrobromides, phosphates, sulfates, hydroiodides, nicotinates, oxalates, picrates, thiocyanates, undecanates, salts with acrylic acid polymers, and salts with carboxyvinyl polymers.

The compound of the present invention or a pharmaceutically acceptable salt thereof may be present as a solvate. Examples of the solvate may include hydrates of the compounds, and hydrates of the pharmaceutically acceptable salts of the compounds. They are all encompassed in the present invention.

When the compounds of the present invention are used as pharmaceutical preparations, the compounds of the present invention may be formulated, by the addition of commonly used excipients, extenders, pH adjusting agents, solubilizers, and the like, into tablets, granules, pills, capsules, powders, solutions, suspensions, injectable agents, liniment, and the like, by using standard techniques. The pharmaceutical preparations can be administered via oral route or percutaneous route, or via intravenous route.

The compound of the present invention can be administered to an adult patient in a dosage of 0.01 to 100 mg/kg, given as a single dose or in divided several doses per day. This dose can be appropriately increased or decreased depending on the type of diseases, age and body weight, symptoms of the patient, and the like.

A preferable aspect of the compound of the present invention includes the following compounds. A compound in which X is the formula: —$CH_2$— or the formula: —CO— is preferred. A compound in which Y is the formula: —$NR^3CO$—W—, the formula: —$NR^3CO$—W—O—, the formula: —$NR^3CO_2$—W—, the formula: —$NR^3$—W—, the formula: —$NR^3SO_2$—W—, the formula: —$NR^3CONR^4$—W—, the formula: —$NR^3CO$—W—$NR^4SO_2$—, the formula: —$CONR^3$—W—, the formula: —$CONR^3$—W—O—, the formula: —$CH_2$—O—W—, the formula: —$CH_2NR^3$—W—, the formula: —$CONR^3$—W—$NR^4CO$—, the formula: —O—W—, or the formula: —O—W—O— is preferred; a compound in which Y is the formula: —$NR^3CO$—W—, or the formula: —$CONR^3$—W— is more preferred; and a compound in which Y is the formula: —NHCO—, or the formula: —CONH—W— (W is a $C_{1-6}$ alkylene group) is further preferred. A compound in which Z is a benzene ring is preferred. More preferably, X and Y are bonded in the para position. A compound in which $R^1$ is a $C_{3-6}$ cycloalkyl group, a $C_{3-6}$ cycloalkenyl group, an adamantyl group, an indanyl group, a tetrahydronaphthyl group, a tetrahydroindolyl group, a phenyl group, a naphthyl group, an indolyl group, a benzofuranyl group, a benzothienyl group, a quinolyl group, or an isoquinolyl group, in which the phenyl group, the naphthyl group, the indolyl group, the benzofuranyl group, the benzothienyl group, the quinolyl group, and the isoquinolyl group may be substituted with 1 to 5 substituent(s) selected from the group consisting of a $C_{1-6}$ alkyl group, a $C_{2-6}$ alkenyl group, a $C_{3-6}$ cycloalkyl group, a halogen atom, a $C_{1-6}$ alkoxy group, a hydroxy group, a $C_{1-6}$ haloalkyl group, a $C_{1-6}$ haloalkoxy group, a cyano group, a nitro group, a $C_{1-6}$ alkylsulfonyl group, a phenyl group, a benzoyl group, a phenoxy group, the formula: —$NR^5R^6$, and the formula: —$SO_2NR^7R^8$ is preferred; a compound in which $R^1$ is a phenyl group, which may be substituted with 1 to 3 substituent(s) selected from the group consisting of a $C_{1-6}$ alkyl group, a halogen atom, a $C_{1-6}$ alkoxy group, a $C_{1-6}$ haloalkyl group, a $C_{1-6}$ haloalkoxy group, a cyano group, a nitro group, a phenyl group, a phenoxy group, and the formula: —$NR^5R^6$ is more preferred; and a compound in which $R^1$ is a phenyl group, which is substituted with 1 to 3 halogen atom(s) is further preferred. A compound in which $R^a$ is a carboxy group is preferred. A compound in which both $R^b$ and $R^c$ are hydrogen atoms is preferred. A compound in which $R^d$, $R^e$, $R^f$ and $R^g$ are each a hydrogen atom is preferred.

The compounds of the present invention can be synthesized by, for example, the below-mentioned production method.

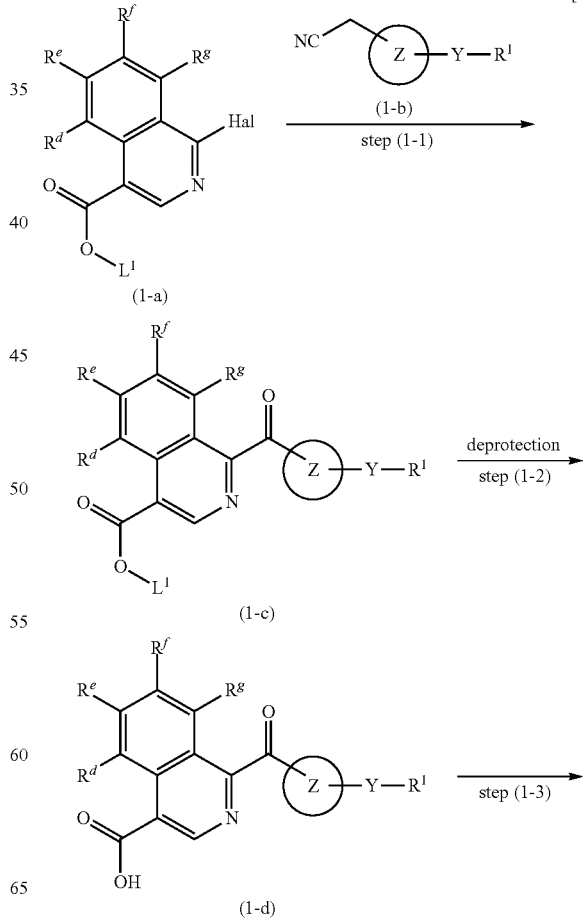

Scheme 1

[Ka 5]

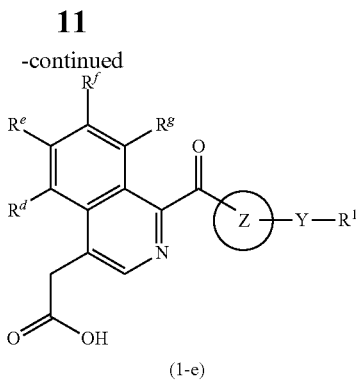

(1-e)

In the scheme, Z, Y, $R^1$, $R^d$, $R^e$, $R^f$ and $R^g$ are the same as defined above, and Hal represents a chlorine atom, a bromine atom, and an iodine atom, and $L^1$ represents general protective groups of carboxylic acid, for example, groups described in Protective Groups in Organic Synthesis (third edition, 1999, P. G. M. Wuts and T. Green) etc., and specifically represents a $C_{1-6}$ alkyl group, a benzyl group, a 4-methoxybenzyl group, or the like.

Step (1-1): Compound 1-c can be produced by allowing compound 1-a to react with compound 1-b in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence of bases such as sodium hydride, tert-butoxy potassium and sodium hexamethyldisilazide, and furthermore by stirring the reacted product in the presence of oxygen.

Step (1-2): This reaction may be carried out by the method described in, for example, Protective Groups in Organic Synthesis (third edition 1999, P. G. M. Wuts and T. Green) etc., or methods similar to this method. Specifically, compound 1-d can be produced by subjecting compound 1-c to hydrolysis with mineral acid such as hydrochloric acid or an inorganic base such as sodium hydroxide and potassium hydroxide in an alcohol solvent such as methanol and ethanol, or in an ether solvent such as tetrahydrofuran and dioxane. When $L^1$ is a benzyl group or a 4-methoxybenzyl group, compound 1-d may be produced by subjecting compound 1-c to hydrogenation in an alcohol solvent such as methanol and ethanol, an ether solvent such as tetrahydrofuran and dioxane, a halogen solvent such as methylene chloride and chloroform, an aromatic hydrocarbon solvent such as toluene and xylene, in the presence of a catalyst such as palladium carbon. When $L^1$ is a 4-methoxybenzyl group, compound 1-d may be produced by deprotection reaction using ceric ammonium nitrate (CAN) or 2,3-dichloro-5,6-dicyano-1,4-benzoquinone (DDQ).

Step (1-3): Carboxylic acid chloride obtained by treating compound 1-d with oxalyl chloride, thionyl chloride, or the like, in a halogen solvent such as methylene chloride and chloroform or in an aromatic hydrocarbon solvent such as toluene and xylene, is treated with diazomethane, trimethylsilyl diazomethane, or the like, in ether solvent such as tetrahydrofuran and dioxane and in a polar solvent such as acetonitrile, or the like. Thereby, α-diazomethyl ketone can be produced. This compound is allowed to react with silver oxide, silver acetate, or the like, in a mixture solvent of water and an ether solvent such as tetrahydrofuran and dioxane, or in an aqueous solution, and thereby compound 1-e of the present invention can be produced.

Scheme 2

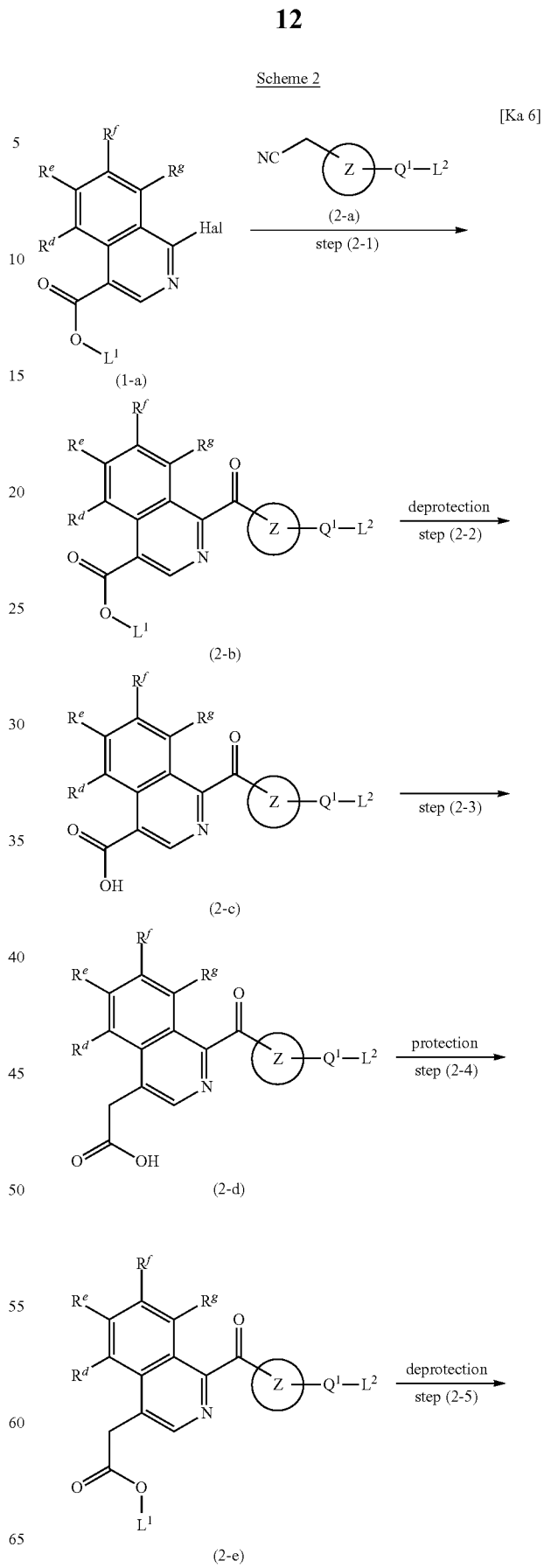

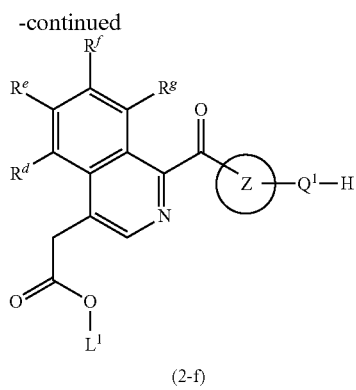

(2-f)

In the scheme, Z, $R^d$, $R^e$, $R^f$, $R^g$, $L^1$, and Hal are the same as defined above, and $Q^1$ represents the formula: —NH—, the formula: —O—, the formula: —CO$_2$—, the formula: —CH$_2$O—, the formula: —CH$_2$NH—, and $L^2$ represents general protective groups of aniline, phenol, carboxylic acid, primary amine, or primary alcohol, for example, groups described in Protective Groups in Organic Synthesis (third edition, 1999, P. G. M. Wuts and T. Green) etc., and specifically represents a tert-butoxycarbonyl group, a benzyl group, a 4-methoxybenzyl group, a methyl group, an acetyl group, a trimethylsilyl group, a tert-butyldimethylsilyl group, or the like, when $Q^1$ is the formula: —NH—, the formula: —O—, the formula: —CH$_2$O—, or the formula: —CH$_2$NH—, and represents a $C_{1-6}$ alkyl group, a benzyl group, a 4-methoxybenzyl group, or the like, when $Q^1$ is the formula: —CO$_2$—.

Step (2-1): Compound 2-b can be produced by using compound 2-a by the same procedure as used in step (1-1).

Step (2-2): Compound 2-c can be produced by using compound 2-b by the same procedure as used in step (1-2).

Step (2-3): Compound 2-d can be produced by using compound 2-c by the same procedure as used in step (1-3).

Step (2-4): Compound 2-e can be produced by subjecting compound 2-d to esterification with $C_{1-6}$ alkyl alcohol, benzyl alcohol, 4-methoxybenzyl alcohol, or the like in the presence of mineral acid such as sulfuric acid. Alternatively, compound 2-e may be produced by allowing compound 2-d to react with $C_{1-6}$ alkyl alcohol, benzyl alcohol, 4-methoxybenzyl alcohol, or the like, in ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or the absence of a base such as triethylamine and pyridine, and in the presence of a condensing agent such as dicyclohexyl carbodiimide (DCC), 1-ethyl-3-(dimethylaminopropyl)-carbodiimide hydrochloride (EDC), benzotriazol-1-yloxytripyrrolidinophosphonium hexafluorophosphate (PyBOP (registered trademark)), 1-hydroxybenzotriazole hydrate (HOBt), or the like. Alternately, compound 2-e may be produced by reacting carboxylic acid chloride obtained by treating compound 2-d with oxalyl chloride, thionyl chloride, or the like, in a halogen solvent such as methylene chloride and chloroform or an aromatic hydrocarbon solvent such as toluene and xylene, with $C_{1-6}$ alkyl alcohol, benzyl alcohol, 4-methoxybenzyl alcohol, or the like. Furthermore, when $L^1$ is a methyl group, compound 2-e may be produced by allowing compound 2-d to react with diazomethane, trimethylsilyl diazomethane, or the like, in an alcohol solvent such as methanol and ethanol. Also, compound 2-e may be produced by allowing compound 2-d to react with iodomethane in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide in the presence of a base such as triethylamine, pyridine, potassium carbonate, or the like.

Step (2-5): This reaction may be carried out by the method described in, for example, Protective Groups in Organic Synthesis (third edition 1999, P. G. M. Wuts and T. Green) etc., or methods similar to this method. Specifically, when $L^2$ is a tert-butoxycarbonyl group, a tert-butyl group, a 4-methoxybenzyl group, or a trimethylsilyl group, compound 2-f can be produced by subjecting compound 2-e to deprotection reaction using mineral acid such as hydrochloric acid, acetic acid, trifluoroacetic acid, or the like, in an ether solvent such as tetrahydrofuran and dioxane, a halogen solvent such as methylene chloride and chloroform, or an aromatic hydrocarbon solvent such as toluene and xylene. When $L^2$ is a benzyl group or a 4-methoxybenzyl group, compound 2-f may be produced by subjecting compound 2-e to hydrogenation in an alcohol solvent such as methanol and ethanol, an ether solvent such as tetrahydrofuran and dioxane, a halogen solvent such as methylene chloride and chloroform, an aromatic hydrocarbon solvent such as toluene and xylene, in the presence of a catalyst such as palladium carbon. When $L^2$ is a trimethylsilyl group or a tert-butyldimethylsilyl group, compound 2-f can be produced by treating compound 2-e with potassium fluoride, tetrabutylammonium fluoride, or the like. When $Q^1$ is the formula: —O— or the formula: —CH$_2$O—, and $L^2$ is a methyl group, compound 2-f can be produced by treating compound 2-e with BBr$_3$ in a halogen solvent such as methylene chloride and chloroform or an aromatic hydrocarbon solvent such as toluene and xylene. When $L^2$ is an acetyl group, compound 2-f can be produced by subjecting compound 2-e to hydrolysis with mineral acid such as hydrochloric acid or an inorganic base such as sodium hydroxide and potassium hydroxide in an alcohol solvent such as methanol and ethanol or an ether solvent such as tetrahydrofuran and dioxane. When $Q^1$ is the formula: —CO$_2$—, compound 2-f can be produced by the same procedure as used in step (1-2).

Scheme 3

[Ka 7]

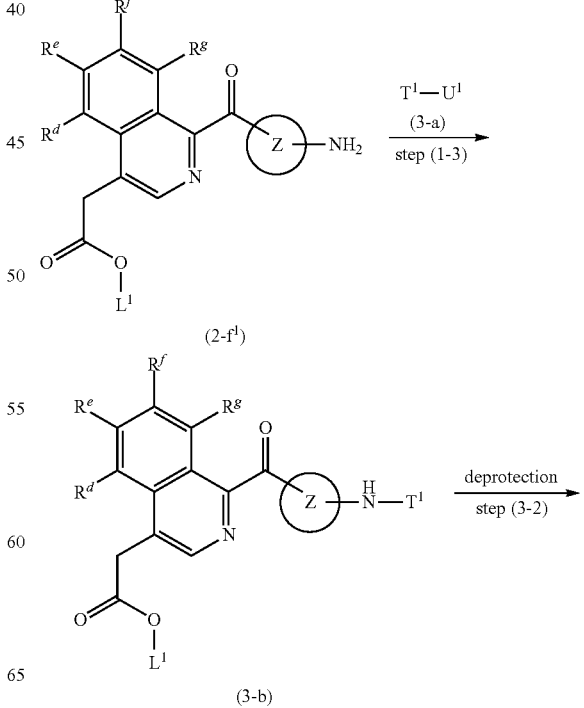

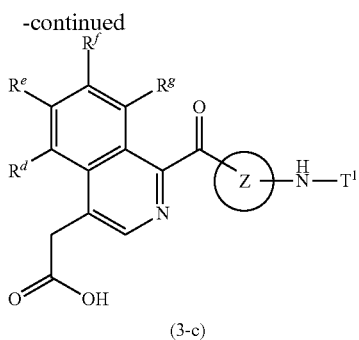

(3-c)

In the scheme, Z, $R^d$, $R^e$, $R^f$, $R^g$, and $L^1$ are the same as defined above, and $T^1$ represents the formula: —CO—W—$R^1$, the formula: $CO_2$—W—$R^1$, the formula: —CO—W—O—$R^1$, the formula: —$SO_2$—W—$R^1$, or the formula: —CO—W—$NR^4SO_2$—$R^1$ (W, $R^1$, and $R^4$ are the same as defined above), $U^1$ represents a general leaving group, for example, a chlorine atom, a bromine atom, an iodine atom, a phenoxy group, an imidazolyl group, a triazolyl group, and the like.

Step (3-1): When $U^1$ is a chlorine atom, a bromine atom, an iodine atom, a phenoxy group, an imidazolyl group, or a triazolyl group, compound 3-b can be produced by allowing compound 3-a to react with compound 2-$f^1$ in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or absence of a base such as triethylamine and pyridine. Also, compound 3-b may be produced by allowing compound 3-a to react with compound 2-$f^1$ by using a base such as pyridine and triethylamine as a solvent. When $T^1$ is the formula: —CO—W—$R^1$, the formula: —CO—W—O—$R^1$, or the formula: —CO—W—$NR^4SO_2$—$R^1$, $U^1$ may be a hydroxyl group, and compound 3-b may be produced by allowing compound 3-a with compound 2-$f^1$ in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or absence of a base such as triethylamine and pyridine, and in the presence of a condensing agent such as dicyclohexyl carbodiimide (DCC), 1-ethyl-3-(dimethylaminopropyl)-carbodiimide hydrochloride (EDC), benzotriazol-1-yloxytripyrrolidinophosphonium hexafluorophosphate (PyBOP (registered trademark)), 1-hydroxybenzotriazole hydrate (HOBt), or the like.

Step (3-2): Compound 3-c can be produced by using compound 3-b by the same procedure as used in step (1-2).

Scheme 4

[Ka 8]

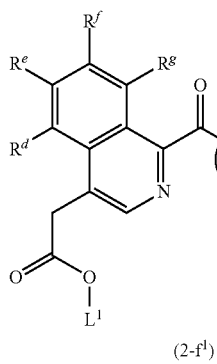

(2-$f^1$)

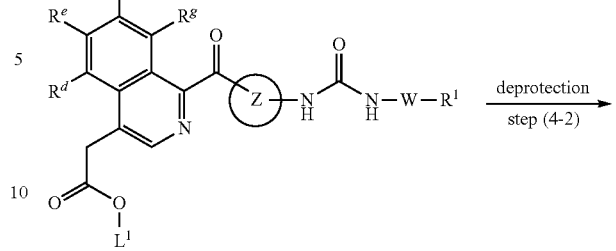

(4-b)

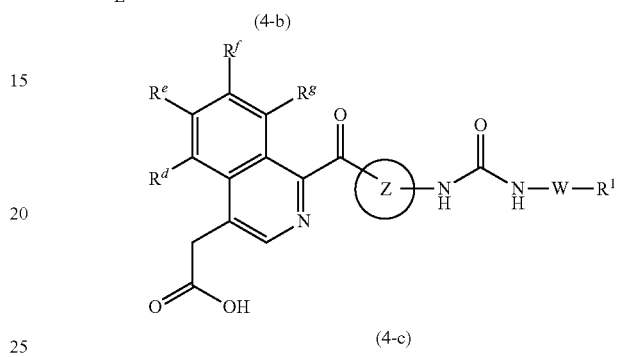

(4-c)

In the scheme, Z, $R^d$, $R^e$, $R^f$, $R^g$, W, and $L^1$ are the same as defined above.

Step (4-1): Compound 4-b can be produced by allowing compound 4-a to react with compound 2-$f^1$ in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide.

Step (4-2): Compound 4-c can be produced by using compound 4-b by the same procedure as used in step (1-2).

Scheme 5

[Ka 9]

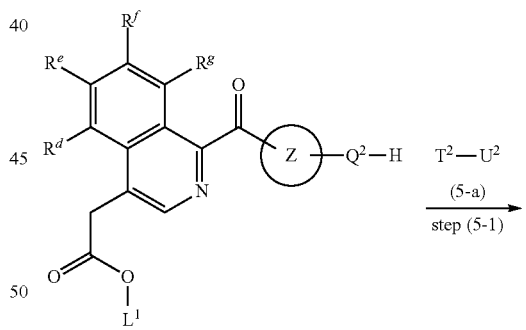

(5-a)
step (5-1)

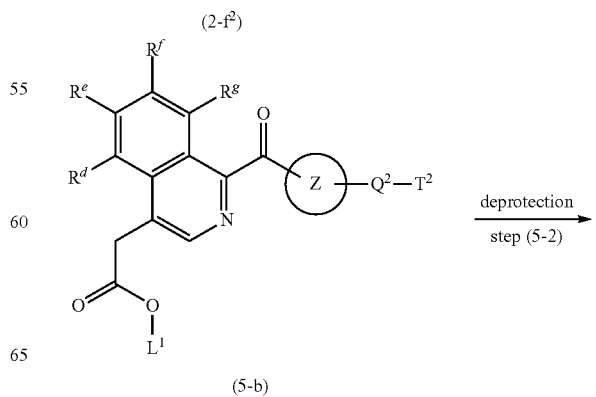

(5-b)

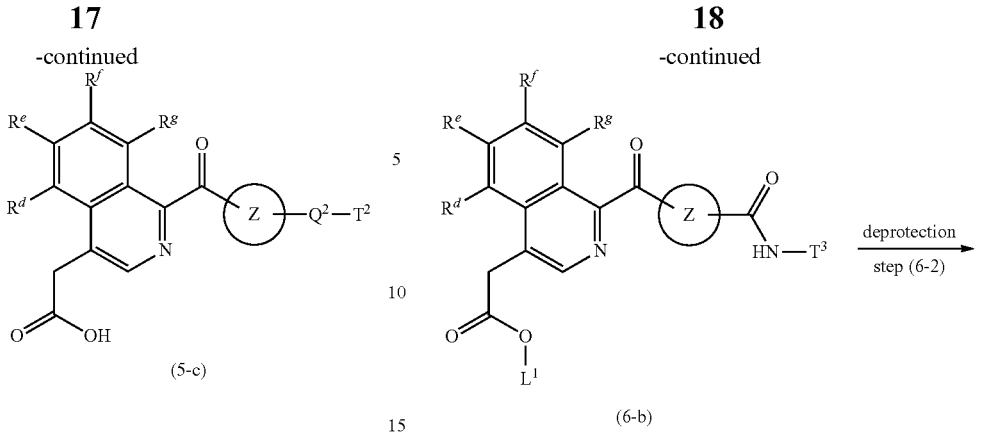

In the scheme, Z, $R^d$, $R^e$, $R^f$, $R^g$ and $L^1$ are the same as defined above, and $Q^2$ represents the formula: —NH—, the formula: —O—, the formula: —CH$_2$O—, or the formula: —CH$_2$NH—, $T^2$ represents the formula: —W—$R^1$, or the formula: —W—O—$R^1$ (W, $R^1$ are the same as defined above), $U^2$ represents a general leaving group, for example, a chlorine atom, a bromine atom, an iodine atom, a methane sulfonyloxy group, a p-toluene sulfonyloxy group, or the like.

Step (5-1): Compound 5-b can be produced by allowing compound 5-a to react with compound 2-f$^2$ in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or absence of a base such as triethylamine, pyridine, and potassium carbonate. When $Q^2$ is the formula: —O—, $U^2$ may be a hydroxyl group, and compound 5-b may be produced by allowing compound 5-a to react with compound 2-f$^2$ in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence of a reagent such as triphenylphosphine and tri-n-butyl phosphine, diethyl azodicarboxylate and tetramethyl azodicarboxy amide.

Step (5-2): Compound 5-c can be produced by using compound 5-b by the same procedure as used in step (1-2).

Scheme 6

[Ka 10]

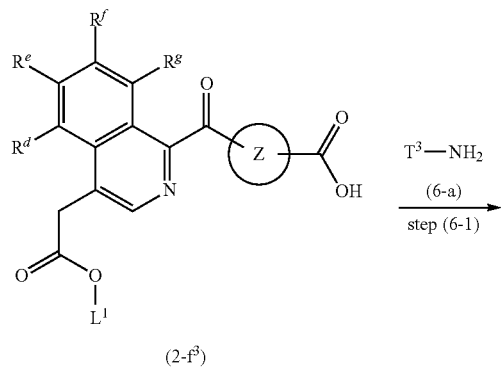

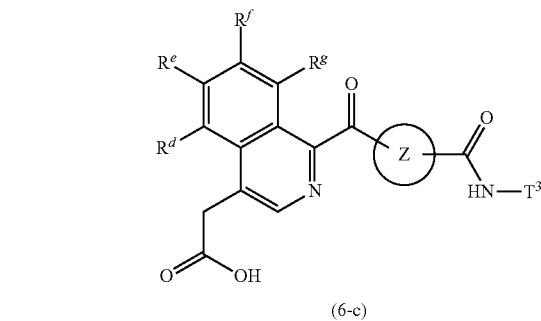

In the scheme, Z, $R^d$, $R^e$, $R^f$, $R^g$ and $L^1$ are the same as defined above, and $T^3$ represents the formula: the formula: —W—O—$R^1$, or the formula: —W—NR$^4$CO—$R^1$ (W, $R^1$ and $R^4$ are the same as defined above).

Step (6-1): Compound 6-b can be produced by allowing compound 6-a to react with compound 2-f$^3$ in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or absence of a base such as triethylamine and pyridine, in the presence of a condensing agent such as dicyclohexyl carbodiimide (DCC), 1-ethyl-3-(dimethylaminopropyl)-carbodiimide hydrochloride (EDC), benzotriazol-1-yloxytripyrrolidinophosphonium hexafluorophosphate (PyBOP (registered trademark)), 1-hydroxybenzotriazole hydrate (HOBt), or the like. Alternatively, compound 6-b may be produced by allowing carboxylic acid chloride obtained by treating compound 2-f$^3$ with oxalyl chloride, thionyl chloride, or the like, in a halogen solvent such as methylene chloride and chloroform, or an aromatic hydrocarbon solvent such as toluene and xylene to react with compound 6-a in an ether solvent such as tetrahydrofuran and dioxane, a halogen solvent such as methylene chloride and chloroform, or an aromatic hydrocarbon solvent such as toluene and xylene.

Step (6-2): Compound 6-c can be produced by using compound 6-b by the same procedure as used in step (1-2).

Scheme 7

[Ka 11]

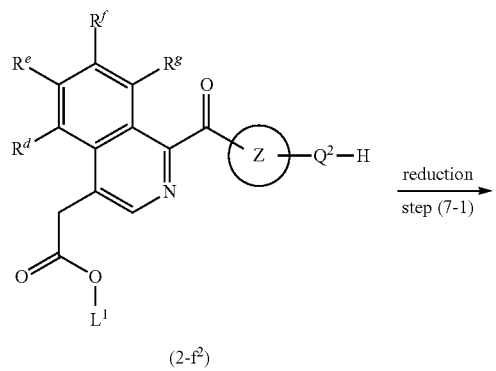

(2-f$^2$)

↓ reduction
step (7-1)

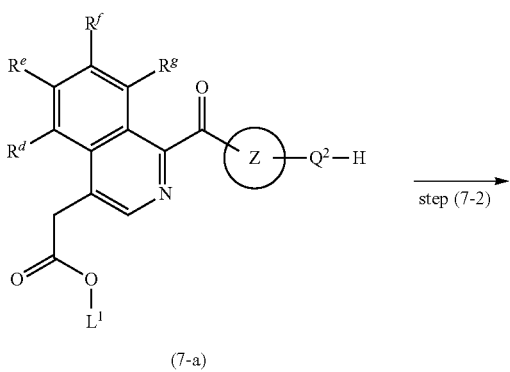

(7-a)

↓ step (7-2)

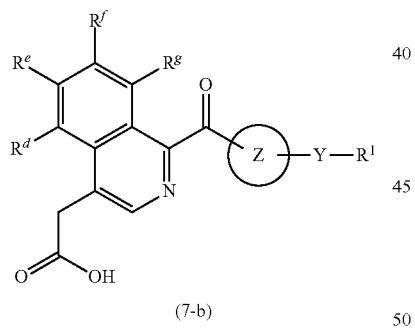

(7-b)

In the scheme, Z, $R^1$, $R^d$, $R^e$, $R^f$, $R^g$, $L^1$, and $Q^2$ are the same as defined above.

Step (7-1): Compound 7-a can be produced by treating compound 2-f$^2$ with a reducing agent such as sodium borohydride and lithium aluminum hydride in an alcohol solvent such as methanol and ethanol, an ether solvent such as tetrahydrofuran and dioxane, a halogen solvent such as methylene chloride and chloroform, or an aromatic hydrocarbon solvent such as toluene and xylene. Compound 7-a may be produced by reacting with trimethylsilane in an ether solvent such as tetrahydrofuran and dioxane, a halogen solvent such as methylene chloride and chloroform, or an aromatic hydrocarbon solvent such as toluene and xylene in the presence of trifluoroacetic acid, boron trifluoride etherate, or the like. Alternatively, compound 7-a may be produced by hydrogenating compound 2-f$^2$ in an alcohol solvent such as methanol and ethanol, an ether solvent such as tetrahydrofuran and dioxane, a halogen solvent such as methylene chloride and chloroform, or an aromatic hydrocarbon solvent such as toluene and xylene, in the presence of a catalyst such as palladium carbon.

Step (7-2): Compound 7-b can be produced by using compound 7-a by the same procedure as in the schemes 3 to 5. In this case, however, Y represents the formula: —NR$^3$CO—W—, the formula: —NR$^3$CO—W—O—, the formula: —NR$^3$CO$_2$—W—, the formula: —NR$^3$—W—, the formula: —NR$^3$SO$_2$—W—, the formula: —NR$^3$CONR$^4$—W—, the formula: —NR$^3$CO—W—NR$^4$SO$_2$—, the formula: —CH$_2$—O—W—, the formula: —CH$_2$NR$^3$—W—, the formula: —O—W—, or the formula: —O—W—O— (W, R$^3$, and R$^4$ are the same as defined above).

Scheme 8

[Ka 12]

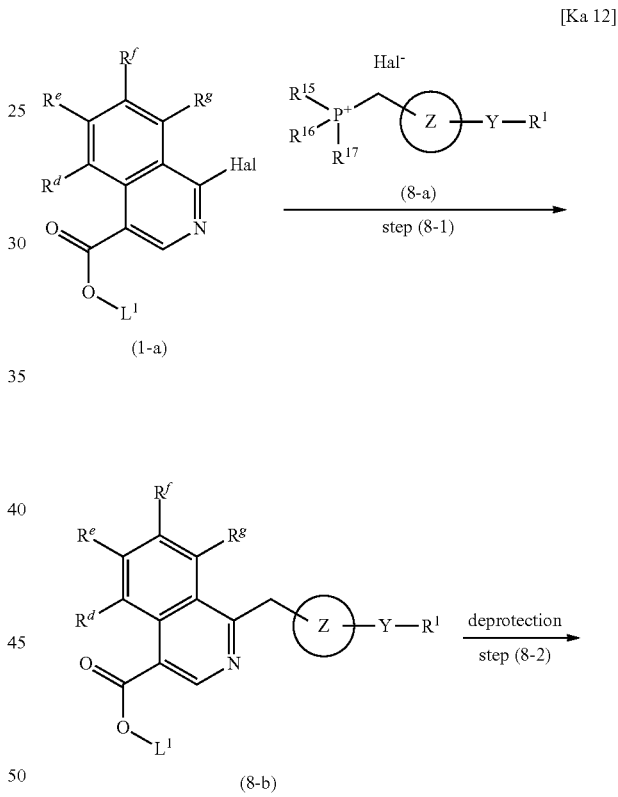

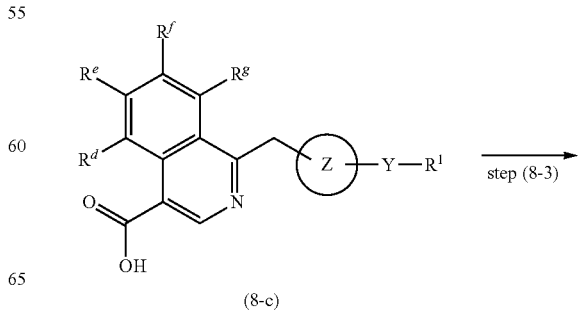

(8-c)

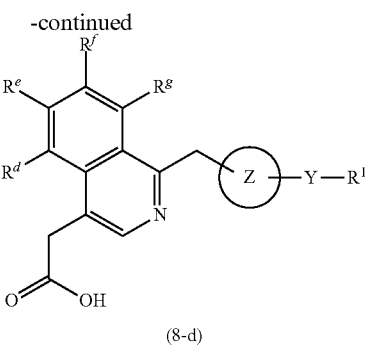

(8-d)

In the scheme, Z, Y, $R^1$, $R^d$, $R^e$, $R^f$, $R^g$, $L^1$, and Hal are the same as defined above, and $R^{15}$, $R^{16}$, and $R^{17}$ represent a $C_{1-6}$ alkyl group.

Step (8-1): Compound 8-b can be produced by allowing compound 8-a to react with compound 1-a in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence of a base such as sodium hydride, tert-butoxy potassium and sodium hexamethyldisilazide, and further treating the reacted product in an aqueous solution of sodium carbonate, potassium carbonate, or the like.

Step (8-2): Compound 8-c can be produced by using compound 8-b by the same procedure as used in step (1-2).

Step (8-3): Compound 8-d can be produced by using compound 8-c by the same procedure as used in step (1-3).

Scheme 9

[Ka 13]

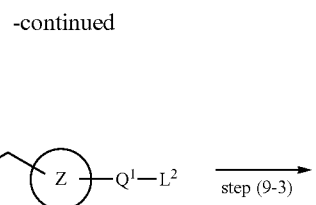

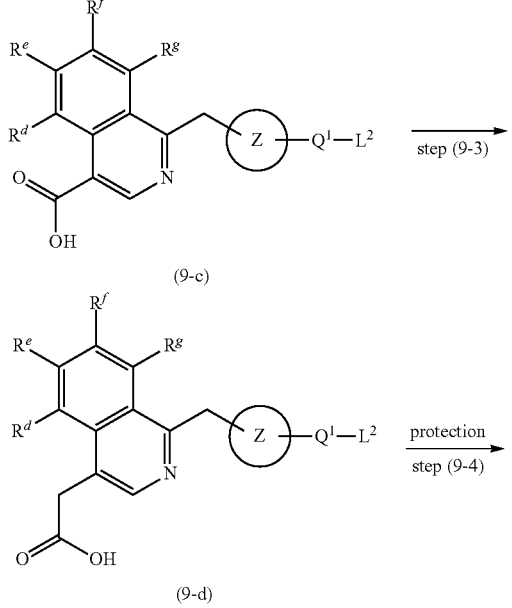

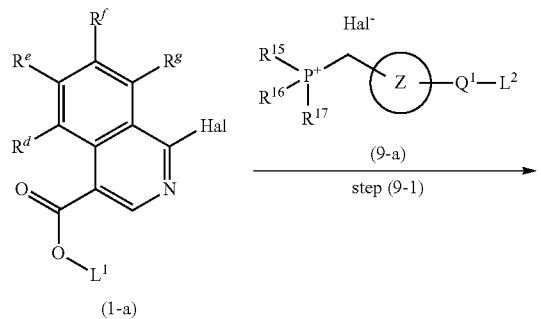

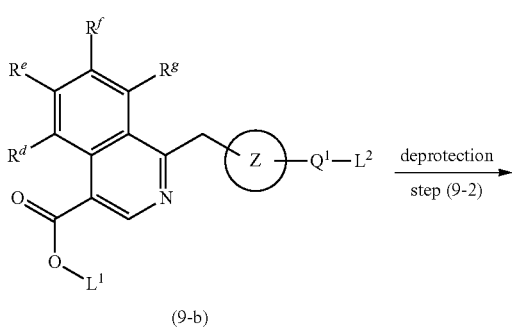

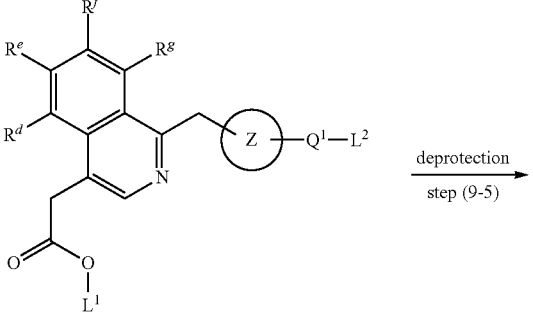

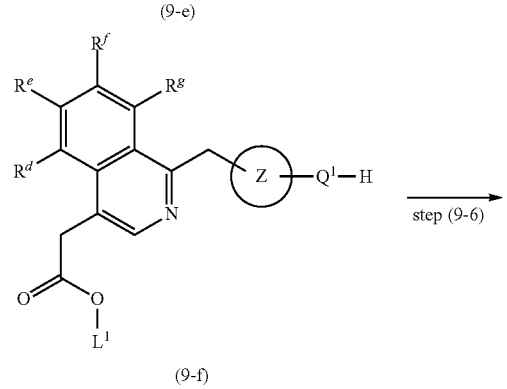

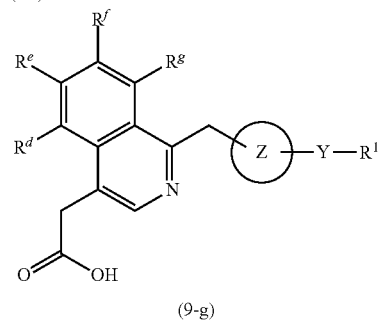

In the scheme, Z, $R^d$, $R^e$, $R^f$, $R^g$, $R^{15}$, $R^{16}$, $R^{17}$, $Q^1$, $L^1$, $L^2$, and Hal are the same as defined above.

Step (9-1): Compound 9-b can be produced by using compound 9-a by the same procedure as used in step (8-1).

Step (9-2): Compound 9-c can be produced by using compound 9-b by the same procedure as used in step (1-2).

Step (9-3): Compound 9-d can be produced by using compound 9-c by the same procedure as used in step (1-3).

Step (9-4): Compound 9-e can be produced by using compound 9-d by the same procedure as used in step (2-4).

Step (9-5): Compound 9-f can be produced by using compound 9-e by the same procedure as used in step (2-5).

Step (9-6): Compound 9-g can be produced by using compound 9-f by the same procedure as in the schemes 3 to 6. In this case, however, Y represents the formula: —$NR^3CO$—W—, the formula: —$NR^3CO$—W—O—, the formula: —$NR^3CO_2$—W—, the formula: —$NR^3$—W—, the formula: —$NR^3SO_2$—W—, the formula: —$NR^3CONR^4$—W—, the formula: —$NR^3CO$—W—$NR^4SO_2$—, the formula: —$CONR^3$—W—, the formula: —$CONR^3$—W—O—, the formula: —$CH_2$—O—W—, the formula: —$CH_2NR^3$—W—, the formula: —$CONR^3$—W—$NR^4CO$—, the formula: —O—W—, or the formula: —O—W—O— (W, $R^3$, and $R^4$ are the same as defined above).

Scheme 10

[Ka 14]

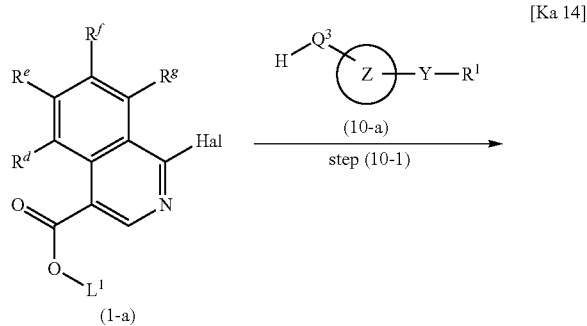

(10-b)

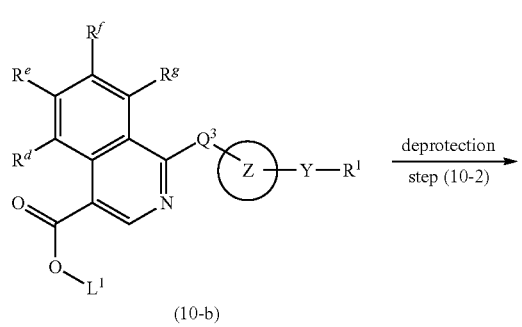

(10-c)

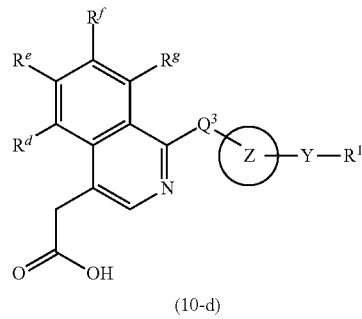

(10-d)

In the scheme, Z, Y, $R^1$, $R^d$, $R^e$, $R^f$, $R^g$, $L^1$, and Hal are the same as defined above, and $Q^3$ represents an oxygen atom, a sulfur atom, or the formula: —$NR^2$— ($R^2$ is the same as defined above).

Step (10-1): Compound 10-b can be produced by allowing compound 10-a to react with compound 1-a in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or absence of a base such as triethylamine, pyridine, and potassium carbonate.

Step (10-2): Compound 10-c can be produced by using compound 10-b by the same procedure as used in step (1-2).

Step (10-3): Compound 10-d can be produced by using compound 10-c by the same procedure as used in step (1-3).

Scheme 11

[Ka 15]

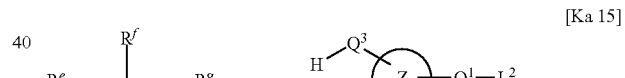

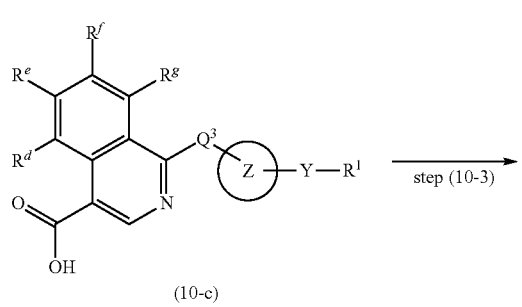

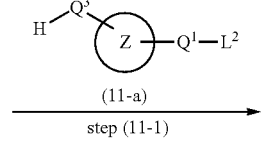

(11-b)

-continued

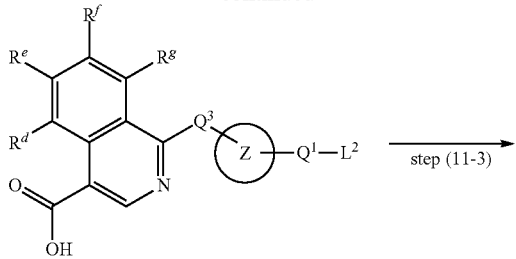

(11-c)

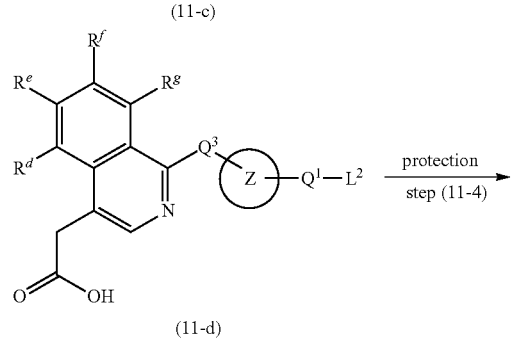

(11-d)

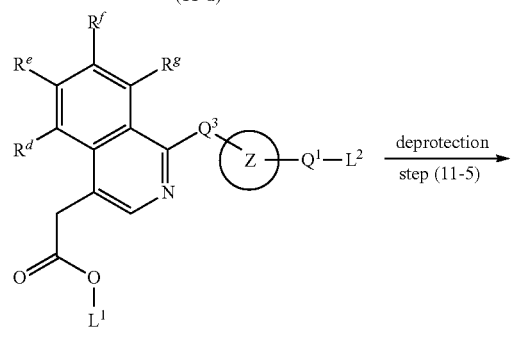

(11-e)

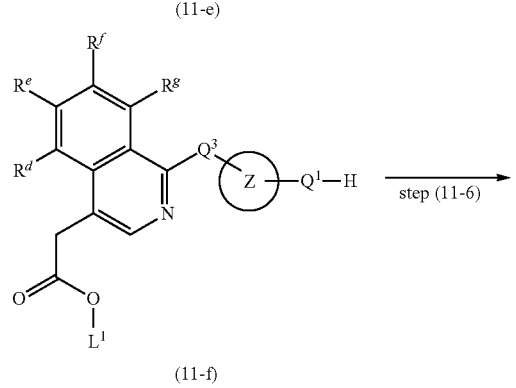

(11-f)

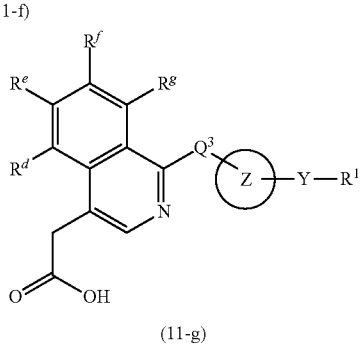

(11-g)

In the scheme, Z, Y, $R^1$, $R^d$, $R^e$, $R^f$, $R^g$, $Q^1$, $Q^3$, $L^1$, $L^2$, and Hal are the same as defined above.

Step (11-1): Compound 11-b can be produced by using compound 11-a by the same procedure as used in step (10-1).

Step (11-2): Compound 11-c can be produced by using compound 11-b by the same procedure as used in step (1-2).

Step (11-3): Compound 11-d can be produced by using compound 11-c by the same procedure as used in step (1-3).

Step (11-4): Compound 11-e can be produced by using compound 11-d by the same procedure as used in step (2-4).

Step (11-5): Compound 11-f can be produced by using compound 11-e by the same procedure as used in step (2-5).

Step (11-6): Compound 11-g can be produced by using compound 11-f by the same procedure as in the schemes 3 to 6. In this case, however, Y represents the formula: —$NR^3CO$—W—, the formula: —$NR^3CO$—W—O—, the formula: —$NR^3CO_2$—W—, the formula: —$NR^3$—W—, the formula: —$NR^3SO_2$—W—, the formula: —$NR^3CONR^4$—W—, the formula: —$NR^3CO$—W—$NR^4SO_2$—, the formula: —$CONR^3$—W—, the formula: —$CONR^3$—W—O—, the formula: —$CH_2$—O—W—, the formula: —$CH_2NR^3$—W—, the formula: —$CONR^3$—W—$NR^4CO$—, the formula: —O—W—, or the formula: —O—W—O—(W, $R^3$, and $R^4$ are the same as defined above).

Scheme 12

[Ka 16]

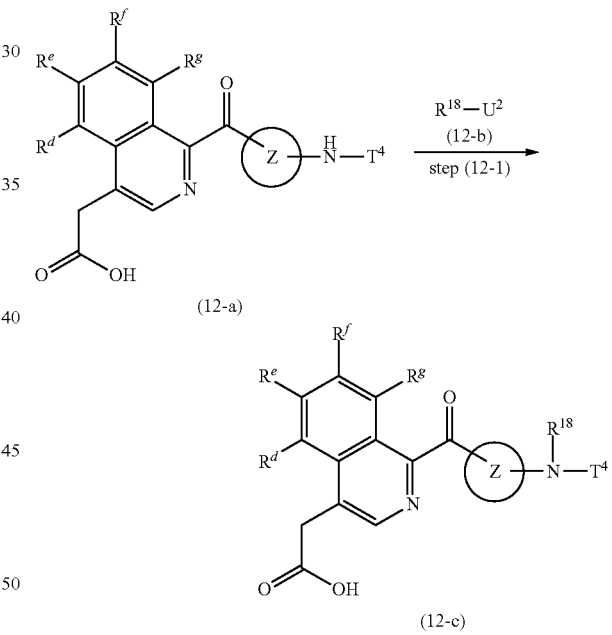

In the scheme, Z, $R^d$, $R^e$, $R^f$, $R^g$, and $U^2$ are the same as defined above; $T^4$ represents the formula: —W—$R^1$, the formula: —CO—W—$R^1$, the formula: —$CO_2$—W—$R^1$, the formula: —CO—W—O—$R^1$, or the formula: —$SO_2$—W—$R^1$ (W, and $R^1$ are the same as defined above); and $R^{18}$ is a $C_{1-6}$ alkyl group.

Step (12-1): Compound 12-c of the present invention can be produced by allowing compound 12-b to react with compound 12-a in an ether solvent such as tetrahydrofuran and dioxane, a halogen solvent such as methylene chloride and chloroform, an aromatic hydrocarbon solvent such as toluene and xylene, and an aprotic polar solvent such as N,N-dimethylformamide, in the presence of a base such as sodium hydride. Furthermore, a compound of the present invention in which a nitrogen atom is $C_{1-6}$ alkylated can be produced by carrying out the same reaction using compound 4-c, compound 6-c, compound 5-c in which $Q^2$ is the formula: —$CH^2NH$—.

Step (13-1): Compound 13-b can be produced by allowing compound 12-b to react with compound 13-a in an ether solvent such as tetrahydrofuran and dioxane, a halogen solvent such as methylene chloride and chloroform, an aromatic hydrocarbon solvent such as toluene and xylene, and an aprotic polar solvent such as N,N-dimethylformamide, in the presence of a base such as sodium hydride and tert-butoxy potassium.

Step (13-2): Compound 13-c can be produced by using compound 13-b by the same procedure as used in step (2-5).

Step (13-3): A compound of the present invention 13-d can be produced by using compound 13-c by the same procedure as in the schemes 5 to 6. In this case, however, Y represents the formula: —O—W—, the formula: —O—W—O—, the formula: —$CH_2$—O—W—, the formula: —$CONR^3$—W—, the formula: —$CONR^3$—W—O—, or the formula: —$CONR^3$—W—$NR^4CO$—(W, $R^3$, and $R^4$ are the same as defined above).

Scheme 13

[Ka 17]

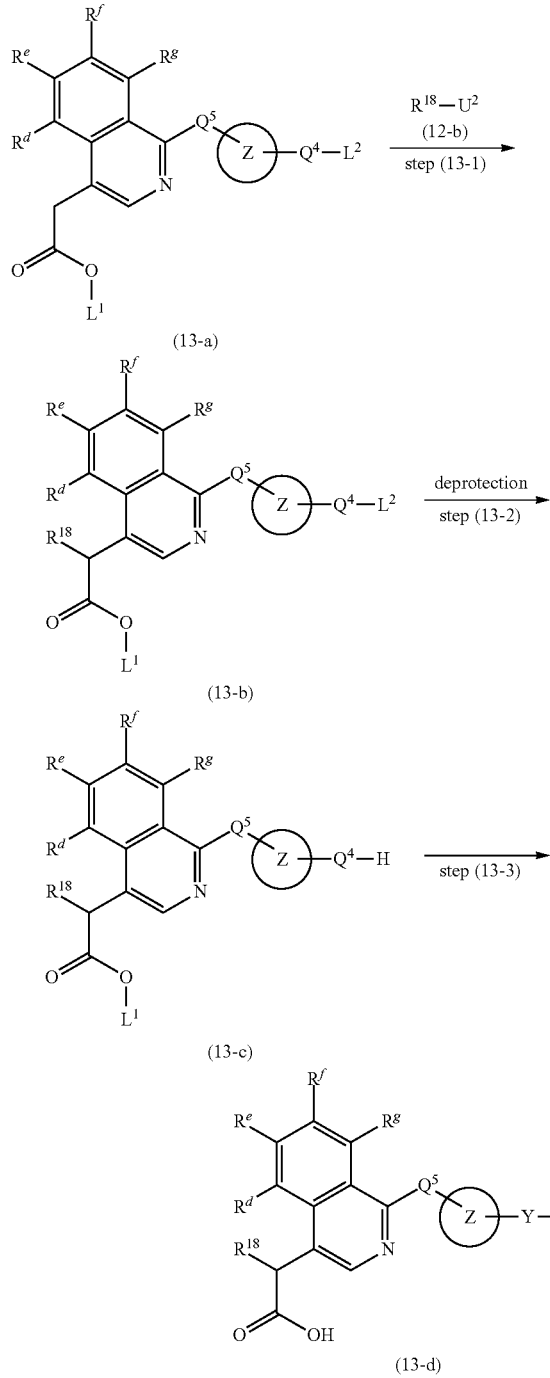

In the scheme, Z, Y, $R^1$, $R^d$, $R^e$, $R^f$, $R^g$, $R^{18}$, $L^1$, $L^2$, and $U^2$ are the same as defined above, $Q^4$ represents the formula: —O—, the formula: —$CO_2$—, or the formula: —$CH_2O$—; and $Q^5$ represents the formula: —$CH_2$— or the formula —CO—.

Scheme 14

[Ka 18]

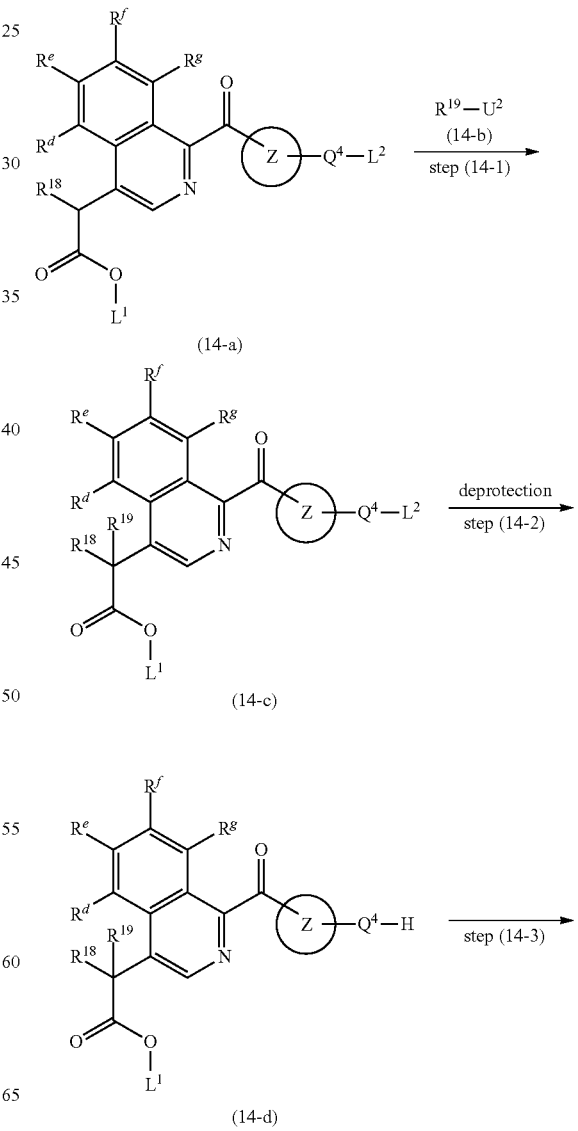

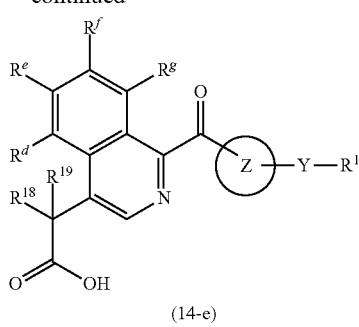

(14-e)

In the scheme, Z, Y, $R^1$, $R^d$, $R^e$, $R^f$, $R^g$, $R^{18}$, $L^1$, $L^2$, $U^2$ and $Q^4$ are the same as defined above, and $R^{19}$ represents a $C_{1-6}$ alkyl group.

Step (14-1): Compound 14-c can be produced by using compound 14-b by the same procedure as used in step (13-1).

Step (14-2): Compound 14-d can be produced by using compound 14-b by the same procedure as used in step (2-5).

Step (14-3): Compound 14-e can be produced by using compound 14-d by the same procedure as in the schemes 5 to 6. In this case, however, Y represents the formula: —O—W—, the formula: —O—W—O—, the formula: —CH$_2$—O—W—, the formula: —CONR$^3$—W—, the formula: —CONR$^3$—W—O—, or the formula: —CONR$^3$—W—NR$^4$CO—(W, $R^3$, and $R^4$ are the same as defined above).

Scheme 15

[Ka 19]

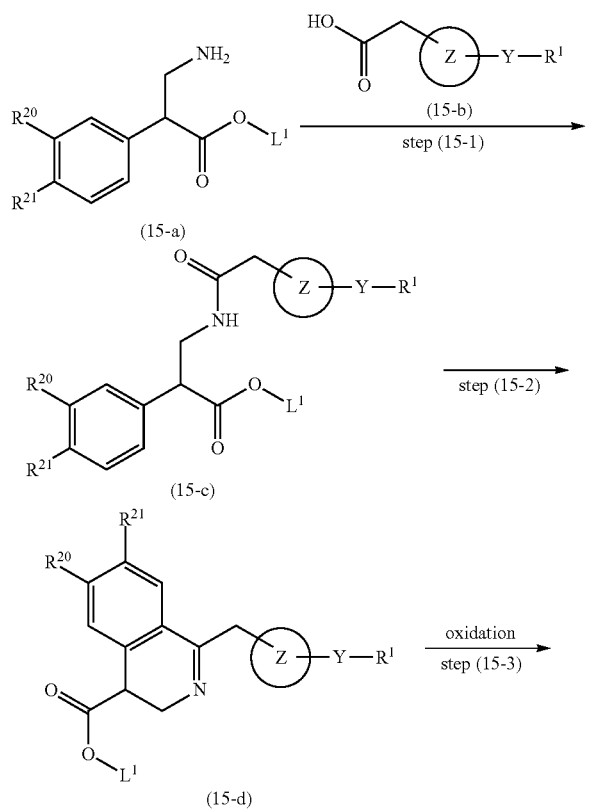

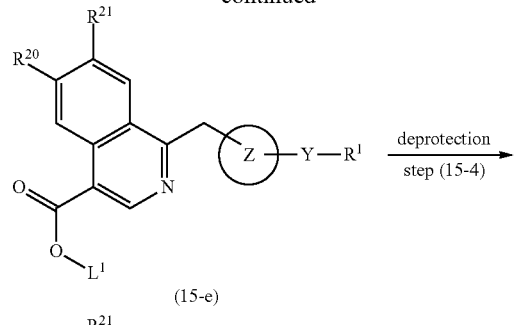

In the scheme, Z, Y, $R^1$, and $L^1$ are the same as defined above, and $R^{20}$ and $R^{21}$ represent a $C_{1-6}$ alkoxy group or a hydrogen atom.

Step (15-1): Compound 15-c can be produced by allowing compound 15-b to react with compound 15-a in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or absence of a base such as triethylamine and pyridine, and in the presence of a condensing agent such as dicyclohexyl carbodiimide (DCC), 1-ethyl-3-(dimethylaminopropyl)-carbodiimide hydrochloride (EDC), benzotriazol-1-yloxytripyrrolidinophosphonium hexafluorophosphate (PyBOP (registered trademark)), 1-hydroxybenzotriazole hydrate (HOBt), or the like. Alternatively, compound 15-c may be produced by allowing a carboxylic acid chloride obtained by treating compound 15-b with oxalyl chloride, thionyl chloride, or the like, in a halogen solvent such as methylene chloride and chloroform, or an aromatic hydrocarbon solvent such as toluene and xylene with compound 15-a in an ether solvent such as tetrahydrofuran and dioxane, a halogen solvent such as methylene chloride and chloroform, and an aromatic hydrocarbon solvent such as toluene and xylene.

Step (15-2): Compound 15-d can be produced by treating compound 15-c with phosphorus oxychloride, diphosphorus pentaoxide, polyphosphoric acid, trifluoroacetic anhydride, trifluoromethanesulfonic anhydride, or the like, in a halogen solvent such as methylene chloride and chloroform, or an aromatic hydrocarbon solvent such as toluene and xylene, in the presence or absence of additives such as 2-chloropyridine.

Step (15-3): Compound 15-e can be produced by treating compound 15-d with sulfur. Alternatively, compound 15-e may be produced by treating compound 15-d with palladium carbon or the like in an aromatic hydrocarbon solvent such as toluene and xylene, or an aliphatic hydrocarbon solvent such as decahydronaphthalene.

Step (15-4): Compound 15-f can be produced by using compound 15-e by the same procedure as used in step (1-2).

Step (15-5): Compound 15-g can be produced by using compound 15-f by the same procedure as used in step (1-3).

Scheme 16

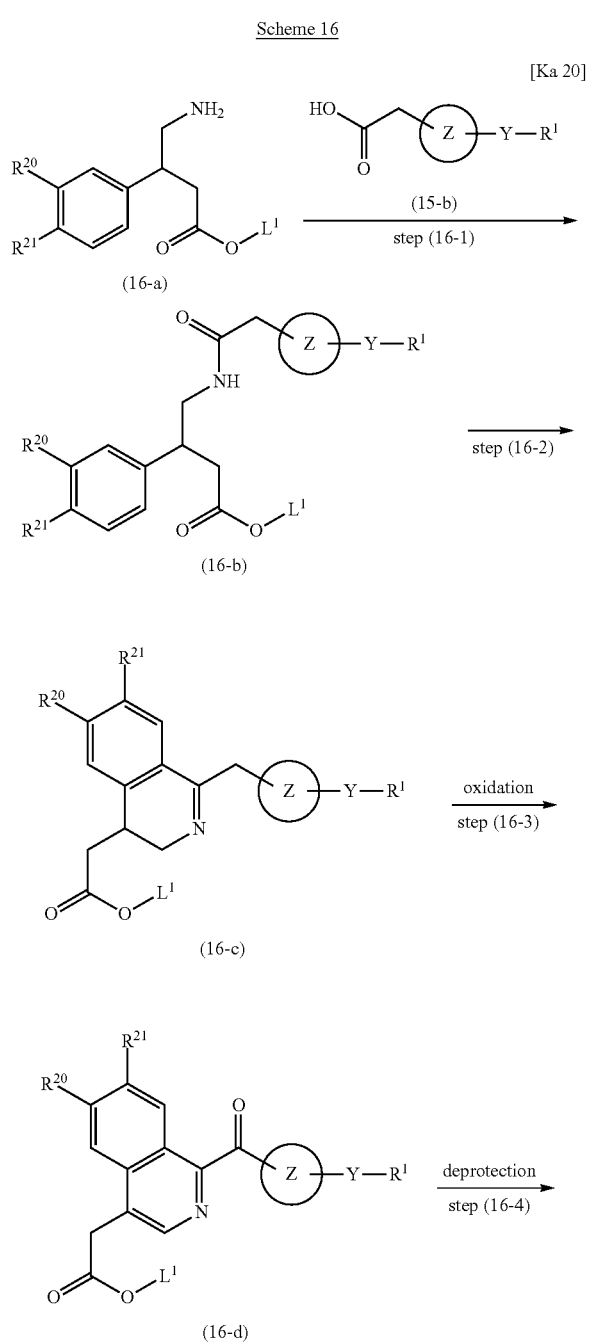

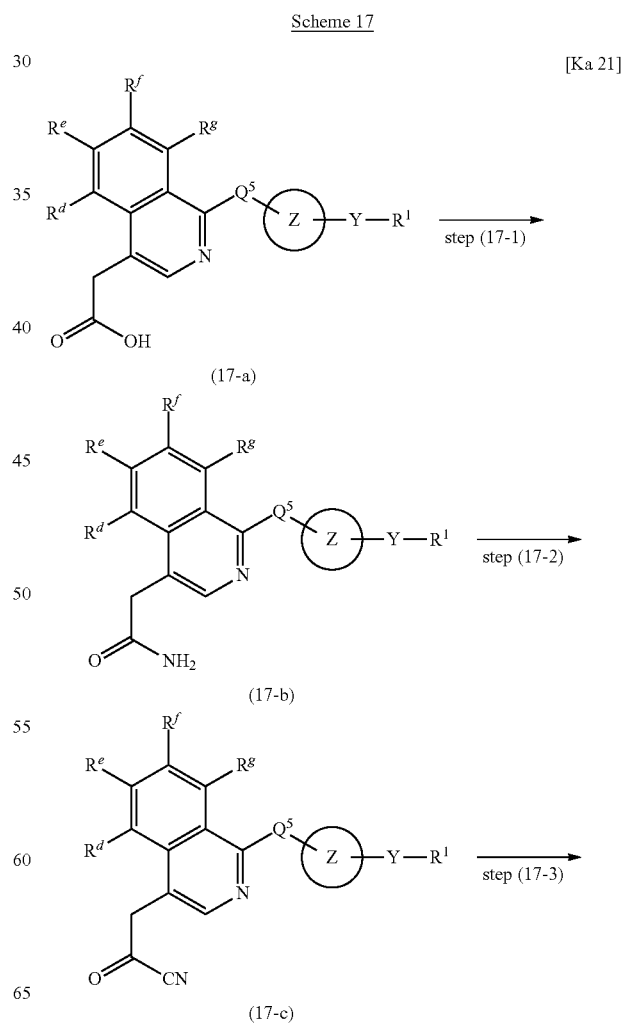

In the scheme, Z, Y, $R^1$, $R^{20}$, $R^{21}$, and $L^1$ are the same as defined above.

Step (16-1): Compound 16-b can be produced by using compound 16-a by the same procedure as used in step (15-1).

Step (16-2): Compound 16-c can be produced by using compound 16-b by the same procedure as used in step (15-2).

Step (16-3): Compound 16-d can be produced by using compound 16-c by the same procedure as used in step (15-3).

Step (16-4): Compound 16-e can be produced by using compound 16-d by the same procedure as used in step (1-2).

Scheme 17

Scheme 18

[Ka 22]

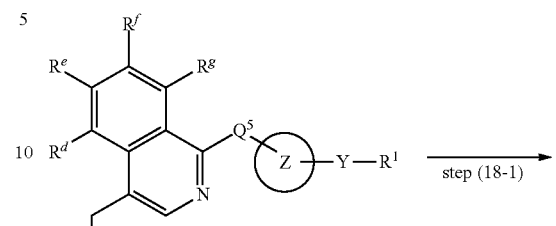

(17-a)

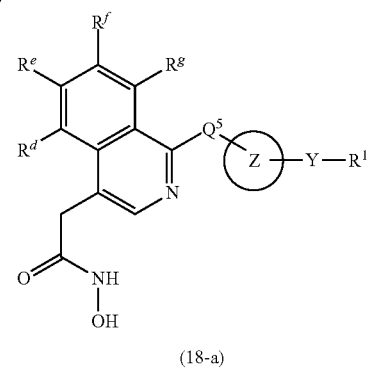

(18-a)

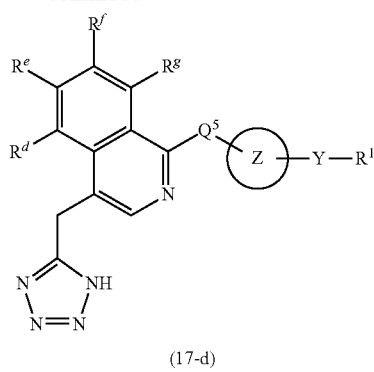

(17-d)

In the scheme, Z, Y, R¹, $R^d$, $R^e$, $R^f$, $R^g$, and $Q^5$ are the same as defined above.

Step (17-1): Compound 17-b can be produced by allowing compound 17-a with aqueous ammonia solution in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or absence of a base such as triethylamine and pyridine, and in the presence of a condensing agent such as dicyclohexyl carbodiimide (DCC), 1-ethyl-3-(dimethylaminopropyl)-carbodiimide hydrochloride (EDC), benzotriazol-1-yloxytripyrrolidinophosphonium hexafluorophosphate (PyBOP (registered trademark)), 1-hydroxybenzotriazole hydrate (HOBt), and 1,1'-carbonyl diimidazole (CDI). Alternatively, compound 17-b of the present invention may be produced by allowing a carboxylic acid chloride obtained by treating compound 17-a with oxalyl chloride, thionyl chloride, or the like, in a halogen solvent such as methylene chloride and chloroform, or an aromatic hydrocarbon solvent such as toluene and xylene with an aqueous ammonia solution in an ether solvent such as tetrahydrofuran and dioxane, a halogen solvent such as methylene chloride and chloroform, and an aromatic hydrocarbon solvent such as toluene and xylene.

Step (17-2): Compound 17-c can be obtained by treating compound 17-b with phosphoryl chloride, thionyl chloride, oxalyl chloride, or the like, in a halogen solvent such as methylene chloride and chloroform, or an aromatic hydrocarbon solvent such as toluene and xylene.

Step (17-3): A compound of the present invention 17-d can be produced by allowing compound 17-c to react with sodium azide in an ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or absence of triethylamine hydrochloride, ammonium chloride, or the like.

In the scheme, Z, Y, $R^d$, $R^e$, $R^f$, $R^g$, and $Q^5$ are the same as defined above.

Step (18-1): Compound 18-a of the present invention can be produced by allowing compound 17-a with hydroxylamine or hydroxylamine hydrochloride in ether solvent such as tetrahydrofuran and dioxane, a halogen solvent such as methylene chloride and chloroform, an aromatic hydrocarbon solvent such as toluene and xylene, or an aprotic polar solvent such as N,N-dimethylformamide, in the presence or the absence of a base such as triethylamine and pyridine, and in the presence of a condensing agent such as dicyclohexyl carbodiimide (DCC), 1-ethyl-3-(dimethylaminopropyl)-carbodiimide hydrochloride (EDC), benzotriazol-1-yloxytripyrrolidinophosphonium hexafluorophosphate (PyBOP (registered trademark)), 1-hydroxybenzotriazole hydrate (HOBt), 1,1'-carbonyl diimidazole (CDI). Compound 18-a of the present invention can be produced by the same procedure by using a reagent such as O-(tetrahydro-2H-pyran-2-yl)hydroxylamine, and O-benzyl hydroxylamine in which a hydroxyl group is protected, instead of using hydroxylamine. Then, the obtained compound is subjected to deprotection reaction by, for example, a method described in Protective Groups in Organic Synthesis (third edition 1999, P. G. M. Wuts and T. Green) etc., or methods similar to this method, and thus compound 18-a of the present invention can be produced. Specifically, when the protecting group is a tetrahydropyranyl group, compound 18-a of the present invention can be produced by deprotection reaction using mineral acid such as hydrochloric acid, acetic acid, trifluoroacetic acid, or the like, in an ether solvent such as tetrahydrofuran and dioxane, a halogen solvent such as methylene chloride and chloroform, or an aromatic hydrocarbon solvent such as toluene and xylene. When the protecting group is a benzyl group, compound 18-a of the present invention can be produced by hydrogenation in the presence of a catalyst such as palladium carbon in an alcohol solvent such as methanol and ethanol, an ether solvent such as tetrahydrofuran and dioxane, a halogen solvent such as methylene chloride and chloroform, or an aromatic hydrocarbon solvent such as toluene and xylene.

Herein, the reaction is carried out in an appropriate temperature selected from −78° C. to boiling points of the solvents to be used in the reaction, and can be used at room temperature, under pressure, under irradiation with microwave, or the like.

Hereinafter, Examples and Test Examples are shown for describing the present invention in detail.

EXAMPLES

Example 1

[1-({4-[(tert-butoxycarbonyl)amino]phenyl}carbonyl)isoquinolin-4-yl]acetic acid (1) To a solution of 4-aminophenyl acetonitrile (1.41 g) in ethanol (5 ml), a solution of di-tert-butyl dicarbonate (3.10 g) in ethanol (5 ml) was added, and the mixed solution was stirred at room temperature for two hours. The precipitate was filtered and dried to give [4-(cyanomethyl)phenyl]carbamic acid 1,1-dimethylethyl ester (984 mg) as a colorless solid.

$^1$H NMR (600 MHz, CHLOROFORM-d) d ppm 1.52 (s, 9H), 3.69 (s, 2H), 6.49 (br. s., 1H), 7.22-7.26 (m, 2H), 7.35-7.41 (m, 2H)

(2) To a solution of the compound (286 mg) obtained in Example 1-(1) in tetrahydrofuran (2 ml), sodium bis(trimethylsilyl)amide (2.6 ml, 1M solution) was added in an ice bath, and the mixed solution was stirred in an ice bath for 30 min. A solution of 1-chloro-isoquinoline-4-carboxylic acid methyl ester in tetrahydrofuran (3 ml) was added in an ice bath, and stirred at room temperature for 2.5 hours. Furthermore, the reaction solution was stirred in an oxygen atmosphere at room temperature for 17 hours. A saturated solution of ammonium chloride was added, followed by extraction with ethyl acetate, and the organic layer was washed with a saturated saline solution. The organic layer was dried over anhydrous magnesium sulfate and evaporated under reduced pressure to remove the solvent. The resulting crude product was purified by column chromatography (NH-type silica gel (NH-DM1020 manufactured by Fuji Silysia Chemical Ltd.) with ethyl acetate/n-hexane=10 to 30%) to give methyl 1-({4-[(tert-butoxycarbonyl)amino]phenyl}carbonyl)isoquinoline-4-carboxylate (289 mg) as a yellow amorphous substance.

$^1$H NMR (600 MHz, CHLOROFORM-d) d ppm 1.53 (s, 9H), 4.07 (s, 3H), 6.72 (br. s., 1H), 7.43-7.49 (m, 2H), 7.62-7.66 (m, 1H), 7.83-7.89 (m, 3H), 8.09-8.13 (m, 1H), 8.99-9.03 (m, 1H), 9.20 (s, 1H)

(3) To a suspension of the compound (1.33 g) obtained in Example 1-(2) in methanol (30 ml), 1N aqueous solution of sodium hydroxide (30 ml) was added, and the mixed solution was stirred at room temperature for 15 hours. The resulting solution was further stirred at 35° C. for three hours, and acetic acid and water were added thereto. The precipitate was filtered, washed with water, and dried to give 1-({4-[(tert-butoxycarbonyl)amino]phenyl}carbonyl)isoquinoline-4-carboxylic acid (1.08 g) as an orange-colored solid.

$^1$H NMR (600 MHz, CHLOROFORM-d) d ppm 1.53 (s, 9H), 6.90 (br. s., 1H), 7.45-7.50 (m, 2H), 7.65-7.69 (m, 1H), 7.86-7.93 (m, 3H), 8.12-8.15 (m, 1H), 9.11-9.15 (m, 1H), 9.39 (s, 1H)

(4) To a solution of the compound (1.08 g) obtained in Example 1-(3) in chloroform (20 ml), oxalyl chloride (0.709 ml) was added dropwise in an ice bath. The solution was stirred at room temperature for 3.5 hours and evaporated under reduced pressure to remove the solvent. To the resulting crude product, tetrahydrofuran (10 ml) and acetonitrile (10 ml) were added, and (trimethylsilyl)diazomethane (2.75 ml, 2 M solution) was added dropwise in an ice bath, and the resulting solution was stirred for two hours in an ice bath. The resulting solution was evaporated under reduced pressure to remove the solvent, and to the resulting crude product, water (10 ml), 1,4-dioxane (10 ml), and silver acetate (138 mg) were added and stirred at 60° C. for 30 min. The solution was returned to room temperature, and water was added to the solution, followed by extraction with ethyl acetate. The organic layer was washed with a saturated saline solution. The organic layer was dried over anhydrous magnesium sulfate, and evaporated under reduced pressure to remove the solvent. To the resulting crude product, methanol (20 ml) was added, (trimethylsilyl)diazomethane (4.54 ml, 2 M solution) was added dropwise, and the solution was stirred at room temperature for 30 min. Water was added thereto, followed by extraction with ethyl acetate. The organic layer was dried over anhydrous magnesium sulfate and evaporated under reduced pressure to remove the solvent. The resulting crude product was purified by column chromatography (neutral OH type silica gel, ethyl acetate/n-hexane=10 to 35%) to give methyl [1-({4-[(tert-butoxycarbonyl)amino]phenyl}carbonyl)isoquinolin-4-yl]acetate (578 mg) as a yellow solid.

$^1$H NMR (600 MHz, CHLOROFORM-d) d ppm 1.51 (s, 9H), 3.72 (s, 3H), 4.10 (s, 2H), 6.72 (br. s., 1H), 7.42-7.47 (m, 2H), 7.58-7.63 (m, 1H), 7.75-7.81 (m, 1H), 7.88-7.93 (m, 2H), 8.02-8.06 (m, 1H), 8.16-8.20 (m, 1H), 8.50 (s, 1H)

(5) To a solution of the compound (1.09 g) obtained in Example 1-(4) in methanol (10 ml), 1.3; N aqueous sodium hydroxide solution (10 ml) was added, and tetrahydrofuran (5 ml) was further added and stirred at room temperature for 1.5 hours. The solution was stirred at 50° C. for 1.5 hours, and then 2N aqueous hydrochloric acid solution was added to the solution, followed by extraction with ethyl acetate. The organic layer was washed with a saturated saline solution, dried over anhydrous magnesium sulfate, and evaporated under reduced pressure to remove the solvent. The resulting crude product was recrystallized (ethyl acetate) to give the titled compound (144 mg) as a colorless solid.

Example 2

{1-[(4-{[(3,4-dichlorophenyl)carbonyl]amino}phenyl)carbonyl]isoquinolin-4-yl}acetic acid (1) To a solution of the compound (100 mg) obtained in Example 1-(4) in chloroform (1 ml), trifluoroacetic acid (1 ml) was added in an ice bath, and the mixed solution was stirred at room temperature for 1.5 hours. A saturated aqueous solution of sodium hydrogencarbonate was added thereto, followed by extraction with chloroform. The organic layer was dried over anhydrous magnesium sulfate, and evaporated under reduced pressure to remove the solvent to give methyl{1-[(4-aminophenyl)carbonyl]isoquinolin-4-yl}acetate (91 mg) as a yellow oily substance.

$^1$H NMR (600 MHz, CHLOROFORM-d) d ppm 3.73 (s, 3H), 4.09 (s, 2H), 6.62-6.66 (m, 2H), 7.58-7.62 (m, 1H), 7.75-7.82 (m, 3H), 8.01-8.04 (m, 1H), 8.15-8.18 (m, 1H), 8.50 (s, 1H)

(2) To a solution of the compound (500 mg) obtained in Example 2-(1) in pyridine (8 ml), 3,4-dichlorobenzoyl chloride (490 mg) was added in an ice bath, and the mixed solution was stirred at room temperature for 13.5 hours. Ethyl acetate, chloroform, and water were added to the solution, followed by extraction with ethyl acetate. The organic layer was washed with diluted hydrochloric acid and a saturated saline solution, dried over anhydrous magnesium sulfate, and then evaporated under reduced pressure to remove the solvent. The resulting crude product was purified by column chromatography (neutral OH type silica gel, ethyl acetate/n-hexane=20 to 50%) to give methyl{1-[(4-{[(3,4-dichlorophenyl)carbonyl]amino}phenyl)carbonyl]isoquinolin-4-yl}acetate (685 mg) as a pale yellow solid.

$^1$H NMR (600 MHz, CHLOROFORM-d) d ppm 3.74 (s, 3H), 4.12 (s, 2H), 7.55-7.83 (m, 7H), 7.97-8.08 (m, 4H), 8.21-8.24 (m, 1H), 8.52 (s, 1H)

(3) To a suspension of the compound (650 mg) obtained in Example 2-(2) in methanol (10 ml), 1N aqueous sodium hydroxide solution (10 ml) was added in an ice bath. Furthermore, tetrahydrofuran (10 ml) was added thereto at room temperature, and the mixture was stirred at room temperature for 30 min. Water and hydrochloric acid were added in an ice bath, which was extracted with chloroform. The organic layer was dried over anhydrous magnesium sulfate, and then evaporated under reduced pressure to remove the solvent. The resulting crude product was recrystallized (ethanol-water) to give the titled compound (489 mg) as a colorless solid.

Compounds of Examples 3 to 126 were obtained by carrying out the same procedures as in Example 2. Structural formulae and NMR values of Examples 1 to 126 are shown in Tables 1-1 to 1-13.

[Ka 23]

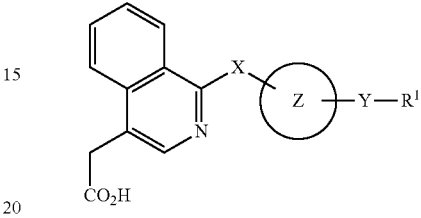

TABLE 1-1

| Example | X | Z | Y | R$^1$ | $^1$H NMR (d ppm) |
|---|---|---|---|---|---|
| 1 | ![C(=O)] | *-C6H4-* (para) | *-NH-C(=O)-O-* | *-C(Me)3 | $^1$H NMR (600 MHz, CHLOROFORM-d), 1.53 (s, 9 H), 4.10 (s, 2 H), 6.98 (br. s., 1 H), 7.36-7.46 (m, 2 H), 7.56-7.64 (m, 1 H), 7.74-7.81 (m, 1 H), 7.83-7.90 (m, 2 H), 7.98-8.06 (m, 1 H), 8.12-8.20 (m, 1 H), 8.50 (s, 1 H) |
| 2 | ![C(=O)] | *-C6H4-* (para) | *-NH-C(=O)-* | *-3,4-dichlorophenyl | $^1$H NMR (600 MHz, DMSO-d6) 4.17 (s, 2 H), 7.70-7.74 (m, 1 H), 7.83-7.93 (m, 4 H), 7.94-7.99 (m, 3 H), 8.02-8.06 (m, 1 H), 8.13-8.16 (m, 1 H), 8.24-8.26 (m, 1 H), 8.54 (s, 1 H), 10.78 (br. s., 1 H) |
| 3 | ![C(=O)] | *-C6H4-* (para) | *-NH-C(=O)-CH2-* | *-3,4-dichlorophenyl | $^1$H NMR (600 MHz, DMSO-d6) 3.76 (s, 2 H), 4.16 (s, 2 H), 7.31-7.34 (m, 1 H), 7.58-7.62 (m, 2 H), 7.68-7.72 (m, 1 H), 7.73-7.77 (m, 2 H), 7.80-7.83 (m, 2 H), 7.87-7.91 (m, 1 H), 7.99-8.02 (m, 1 H), 8.11-8.14 (m, 1 H), 8.52 (s, 1 H), 10.62 (br. s., 1 H), 12.67 (br. s., 1 H) |

TABLE 1-1-continued

| Example | X | Z | Y | R¹ | ¹H NMR (d ppm) |
|---|---|---|---|---|---|
| 4 |  | 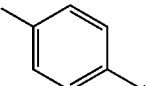 | 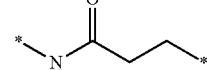 | 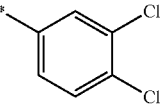 | ¹H NMR (600 MHz, DMSO-d6) 2.70 (t, J = 7.6 Hz, 2 H), 2.92 (t, J = 7.6 Hz, 2 H), 4.17 (s, 2 H), 7.24-7.27 (m, 1 H), 7.52-7.56 (m, 2 H), 7.68-7.75 (m, 3 H), 7.78-7.82 (m, 2 H), 7.87-7.91 (m, 1 H), 7.99-8.02 (m, 1 H), 8.11-8.15 (m, 1 H), 8.52 (s, 1 H), 10.36 (br. s., 1 H), 12.68 (br. s., 1 H) |
| 5 |  | 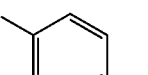 | 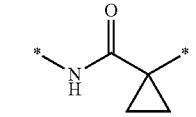 | 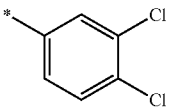 [SMILES: *c1ccc(Cl)c(Cl)c1] | ¹H NMR (600 MHz, DMSO-d6) 1.19-1.25 (m, 2 H), 1.49-1.54 (m, 2 H), 4.15 (s, 2 H), 7.37-7.40 (m, 1 H), 7.59-7.61 (m, 1 H), 7.62-7.64 (m, 1 H), 7.67-7.79 (m, 5 H), 7.86-7.91 (m, 1 H), 7.97-8.00 (m, 1 H), 8.11-8.14 (m, 1 H), 8.51 (s, 1 H), 9.59 (br. s., 1 H) |
| 6 |  | 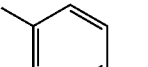 | 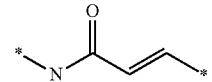 | 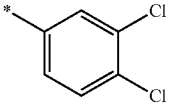 [SMILES: *c1ccc(Cl)c(Cl)c1] | ¹H NMR (600 MHz, DMSO-d6) 4.16 (s, 2 H), 6.92 (d, J = 15.1 Hz, 1 H), 7.58-8.17 (m, 12 H), 8.53 (s, 1 H), 10.68 (s, 1 H) |
| 7 |  | 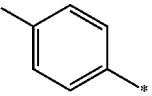 | 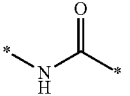 | 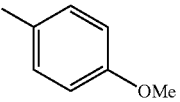 | ¹H NMR (600 MHz, DMSO-d6) 3.85 (s, 3 H), 4.18 (s, 2 H), 7.05-7.11 (m, 2 H), 7.68-8.17 (m, 10 H), 8.54 (s, 1 H), 10.49 (s, 1 H), 12.74 (br. s., 1 H) |
| 8 |  | 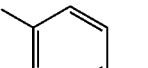 | 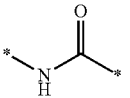 | 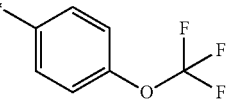 | ¹H NMR (600 MHz, DMSO-d6) 4.17 (s, 2 H), 7.51-8.17 (m, 12 H), 8.54 (s, 1 H), 10.75 (s, 1 H), 12.79 (br. s., 1 H) |

TABLE 1-2

| Example | X | Z | Y | R¹ | ¹H NMR (d ppm) |
|---|---|---|---|---|---|
| 9 |  | 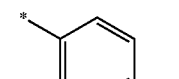 | 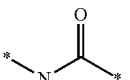 | 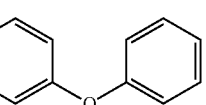 | ¹H NMR (600 MHz, DMSO-d6) 4.16 (s, 2 H), 7.09-7.14 (m, 4 H), 7.22-7.26 (m, 1 H), 7.44-7.49 (m, 2 H), 7.69-7.73 (m, 1 H), 7.83-7.92 (m, 3 H), 7.95-7.99 (m, 2 H), 8.00-8.05 (m, 3 H), 8.13-8.17 (m, 1 H), 8.53 (s, 1 H), 10.59 (br. s., 1 H) |
| 10 |  | 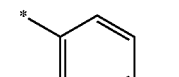 | 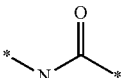 | 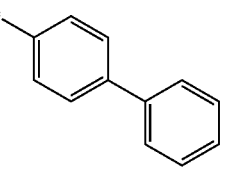 | ¹H NMR (600 MHz, DMSO-d6) 4.19 (s, 2 H), 7.42-7.46 (m, 1 H), 7.50-7.54 (m, 2 H), 7.70-7.74 (m, 1 H), 7.75-7.79 (m, 2 H), 7.84-7.93 (m, 5 H), 7.99-8.06 (m, 3 H), 8.07-8.11 (m, 2 H), 8.13-8.16 (m, 1 H), 8.55 (s, 1 H), 10.70 (br. s., 1 H), 12.65 (br. s., 1 H) |

TABLE 1-2-continued

| Example | X | Z | Y | R¹ | ¹H NMR (d ppm) |
|---|---|---|---|---|---|
| 11 |  | 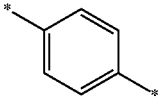 [SMILES: *c1ccc(*)cc1] | 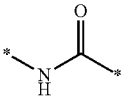 | 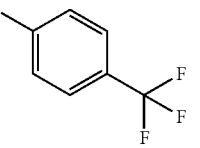 | ¹H NMR (600 MHz, DMSO-d6) 4.18 (s, 2 H), 7.70-7.74 (m, 1 H), 7.86-8.01 (m, 7 H), 8.02-8.06 (m, 1 H), 8.11-8.20 (m, 3 H), 8.54 (s, 1 H), 10.86 (br. s., 1 H), 12.70 (br. s., 1 H) |
| 12 |  | 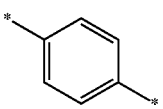 | 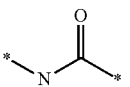 | 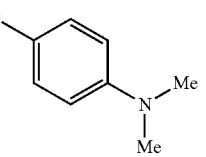 | ¹H NMR (600 MHz, DMSO-d6) 3.00 (s, 6 H), 4.18 (s, 2 H), 6.75-6.79 (m, 2 H), 7.69-7.73 (m, 1 H), 7.80-7.84 (m, 2 H), 7.87-7.92 (m, 3 H), 7.95-7.99 (m, 2 H), 8.00-8.04 (m, 1 H), 8.12-8.15 (m, 1 H), 8.53 (s, 1 H), 10.27 (br. s., 1 H), 12.69 (br. s., 1 H) |
| 13 |  | 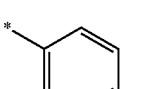 | 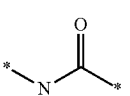 | 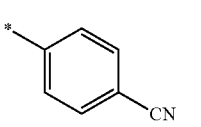 | ¹H NMR (600 MHz, DMSO-d6) 4.17 (s, 2 H), 7.70-7.74 (m, 1 H), 7.86-7.92 (m, 3 H), 7.96-8.00 (m, 2 H), 8.02-8.07 (m, 3 H), 8.11-8.16 (m, 3 H), 8.54 (s, 1 H), 10.88 (br. s., 1 H) |
| 14 |  | 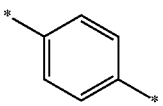 | 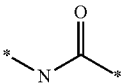 | 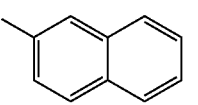 | ¹H NMR (600 MHz, DMSO-d6) 4.19 (s, 2 H), 7.61-8.17 (m, 14 H), 8.55 (s, 1 H), 8.63 (s, 1 H), 10.84 (s, 1 H), 12.72 (br. s., 1 H) |
| 15 |  | 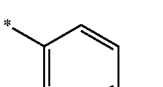 | 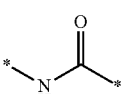 | 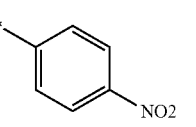 | ¹H NMR (600 MHz, DMSO-d6) 4.19 (s, 2 H), 7.70-7.74 (m, 1 H), 7.87-7.93 (m, 3 H), 7.96-8.01 (m, 2 H), 8.03-8.06 (m, 1 H), 8.13-8.16 (m, 1 H), 8.19-8.23 (m, 2 H), 8.37-8.41 (m, 2 H), 8.55 (s, 1 H), 10.96 (br. s., 1 H), 12.70 (br. s., 1 H) |
| 16 |  | 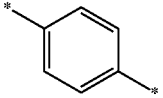 | 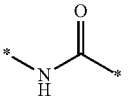 | 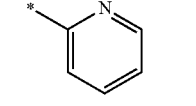 | ¹H NMR (600 MHz, DMSO-d6) 4.18 (s, 2 H), 7.68-8.21 (m, 11 H), 8.54 (s, 1 H), 8.75-8.78 (m, 1 H), 11.04 (s, 1 H), 12.71 (br. s., 1 H) |

TABLE 1-3

| Example | X | Z | Y | R¹ | ¹H NMR (d ppm) |
|---|---|---|---|---|---|
| 17 |  | 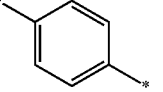 | 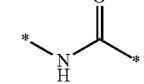 | 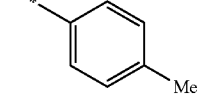 | ¹H NMR (600 MHz, DMSO-d6) 2.40 (s, 3 H), 4.18 (s, 2 H), 7.34-7.38 (m, 2 H), 7.70-7.74 (m, 1 H), 7.83-7.92 (m, 5 H), 7.97-8.00 (m, 2 H), 8.02-8.05 (m, 1 H), 8.12-8.15 (m, 1 H), 8.54 (s, 1 H), 10.56 (br. s., 1 H), 12.69 (br. s., 1 H) |
| 18 |  | 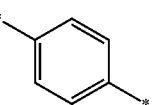 | 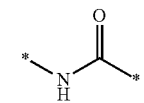 | 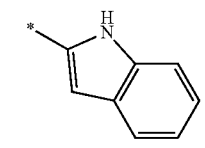 | ¹H NMR (600 MHz, DMSO-d6) 4.18 (s, 2 H), 7.05-8.17 (m, 13 H), 8.54 (s, 1 H), 10.60 (s, 1 H), 11.83 (br. s., 1 H), 12.73 (br. s., 1 H) |
| 19 |  | 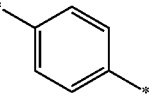 | 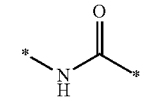 | 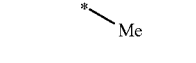 | ¹H NMR (600 MHz, DMSO-d6) 2.09 (s, 3 H), 4.16 (s, 2 H), 7.67-8.15 (m, 8 H), 8.52 (s, 1 H), 10.37 (s, 1 H), 12.73 (br. s., 1 H) |
| 20 |  | 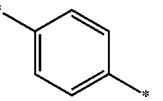 | 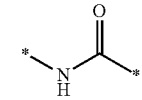 | 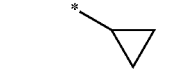 | ¹H NMR (600 MHz, DMSO-d6) 0.79-0.87 (m, 4 H), 1.80-1.87 (m, 1 H), 4.15 (s, 2 H), 7.67-8.16 (m, 8 H), 8.51 (s, 1 H), 10.65 (s, 1 H), 12.70 (br. s., 1 H) |

TABLE 1-3-continued

| Example | X | Z | Y | R¹ | ¹H NMR (d ppm) |
|---|---|---|---|---|---|
| 21 | C(=O) | *-C6H4-* (para) | *-NH-C(=O)-CH2-* | cyclohexyl | ¹H NMR (600 MHz, DMSO-d6) 0.80-1.33 (m, 5 H), 1.55-1.83 (m, 6 H), 2.24 (d, J = 7.3 Hz, 2 H), 4.16 (s, 2 H), 7.65-8.16 (m, 8 H), 8.52 (s, 1 H), 10.29 (s, 1 H), 12.73 (br. s., 1 H) |
| 22 | C(=O) | *-C6H4-* (para) | *-NH-C(=O)-CH2-* | 4-biphenyl | ¹H NMR (600 MHz, DMSO-d6) 3.75 (s, 2 H), 4.15 (s, 2 H), 7.34-7.37 (m, 1 H), 7.41-7.47 (m, 4 H), 7.61-7.66 (m, 4 H), 7.68-7.71 (m, 1 H), 7.76-7.83 (m, 4 H), 7.87-7.90 (m, 1 H), 7.99-8.01 (m, 1 H), 8.12-8.15 (m, 1 H), 8.52 (s, 1 H), 10.65 (br. s., 1 H) |
| 23 | C(=O) | *-C6H4-* (para) | *-NH-C(=O)-CH2-O-* | 3,4-dichlorophenyl | ¹H NMR (600 MHz, DMSO-d6) 4.18 (s, 2 H), 4.84 (s, 2 H), 7.02-7.06 (m, 1 H), 7.31-7.34 (m, 1 H), 7.55-7.57 (m, 1 H), 7.69-7.73 (m, 1 H), 7.79-7.86 (m, 4 H), 7.88-7.92 (m, 1 H), 8.01-8.04 (m, 1 H), 8.12-8.15 (m, 1 H), 8.53 (s, 1 H), 10.53 (br. s., 1 H), 12.68 (br. s., 1 H) |
| 24 | C(=O) | *-C6H4-* (para) | *-NH-C(=O)-* | 2-chlorophenyl | ¹H NMR (600 MHz, DMSO-d6) 4.18 (s, 2 H), 7.44-8.16 (m, 12 H), 8.54 (s, 1 H), 10.95 (br. s., 1 H), 12.67 (br. s, 1 H) |

TABLE 1-4

| Example | X | Z | Y | R¹ | ¹H NMR (d ppm) |
|---|---|---|---|---|---|
| 25 | C(=O) | *-C6H4-* (para) | *-NH-C(=O)-* | 2-bromophenyl | ¹H NMR (600 MHz, DMSO-d6) 4.18 (s, 2 H), 7.42-8.16 (m, 12 H), 8.54 (s, 1 H), 10.93 (br. s, 1 H), 12.68 (br. s., 1 H) |
| 26 | C(=O) | *-C6H4-* (para) | *-NH-C(=O)-* | 2-methylphenyl | ¹H NMR (600 MHz, DMSO-d6) 2.39 (s, 3 H), 4.17 (s, 2 H), 7.28-8.16 (m, 12 H), 8.53 (s, 1 H), 10.73 (br. s, 1 H), 12.69 (br. s, 1 H) |
| 27 | C(=O) | *-C6H4-* (para) | *-NH-C(=O)-* | 3-chlorophenyl | ¹H NMR (600 MHz, DMSO-d6) 4.18 (s, 2 H), 7.57-8.16 (m, 12 H), 8.54 (s, 1 H), 10.73 (s, 1 H), 12.72 (br. s., 1 H) |
| 28 | C(=O) | *-C6H4-* (para) | *-NH-C(=O)-* | 4-fluorophenyl | ¹H NMR (600 MHz, DMSO-d6) 4.18 (s, 2 H), 7.35-8.17 (m, 12 H), 8.54 (s, 1 H), 10.66 (s, 1 H), 12.72 (br. s., 1 H) |
| 29 | C(=O) | *-C6H4-* (para) | *-NH-C(=O)-* | 4-chlorophenyl | ¹H NMR (600 MHz, DMSO-d6) 4.17 (s, 2 H), 7.61-8.16 (m, 12 H), 8.54 (s, 1 H), 10.71 (s, 1 H) |

TABLE 1-4-continued

| Example | X | Z | Y | R¹ | ¹H NMR (d ppm) |
|---|---|---|---|---|---|
| 30 |  | 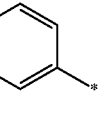 | 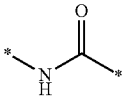 | 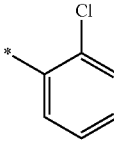 | ¹H NMR (600 MHz, DMSO-d6) 4.17 (s, 2 H), 7.48-8.16 (m, 11 H), 8.53 (s, 1 H), 11.03 (s, 1 H) |
| 31 |  | 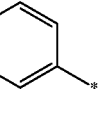 | 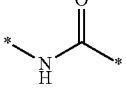 | 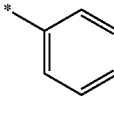 | ¹H NMR (600 MHz, DMSO-d6) 4.17 (s, 2 H), 7.70-8.16 (m, 11 H), 8.54 (s, 1 H), 10.74 (s, 1 H) |
| 32 |  | 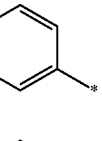 | 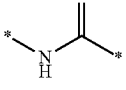 | 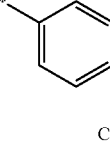 | ¹H NMR (600 MHz, DMSO-d6) 4.18 (br. s., 2 H), 7.69-8.16 (m, 12 H), 8.53 (s, 1 H), 10.71 (br. s, 1 H), 12.70 (br. s, 1 H) |
| 33 |  | 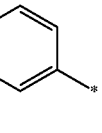 | 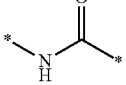 | 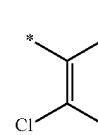 | ¹H NMR (600 MHz, DMSO-d6) 4.18 (s, 2 H), 7.51-8.16 (m, 11 H), 8.54 (s, 1 H), 11.20 (br. s, 1 H), 12.67 (br. s., 1 H) |
| 34 |  | 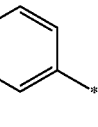 | 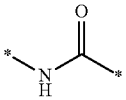 | 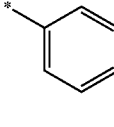 | ¹H NMR (600 MHz, DMSO-d6) 4.18 (s, 2 H), 7.58-8.25 (m, 11 H), 8.54 (s, 1 H), 10.72 (br. s, 1 H), 12.68 (br. s., 1 H) |
| 35 |  | 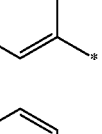 | 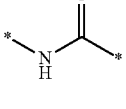 | 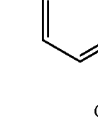 | ¹H NMR (600 MHz, DMSO-d6) 4.18 (s, 2 H), 7.61-8.16 (m, 11 H), 8.54 (s, 1 H), 10.69 (br. s, 1 H), 12.68 (br. s., 1 H) |
| 36 |  | 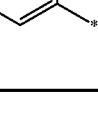 | 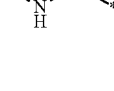 | 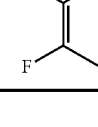 | ¹H NMR (600 MHz, DMSO-d6) 4.18 (s, 2 H), 7.38-8.17 (m, 11 H), 8.54 (s, 1 H), 11.23 (s, 1 H), 12.71 (br. s., 1 H) |

TABLE 1-5

| Example | X | Z | Y | R¹ | ¹H NMR (d ppm) |
|---|---|---|---|---|---|
| 37 |  | 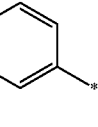 | 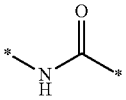 | 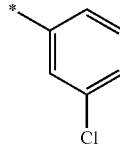 | ¹H NMR (600 MHz, DMSO-d6) 4.18 (s, 2 H), 7.70-8.16 (m, 11 H), 8.54 (s, 1 H), 10.79 (s, 1 H), 12.72 (br. s., 1 H) |
| 38 |  | 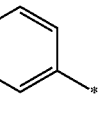 | 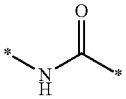 | 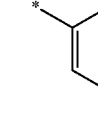 | ¹H NMR (600 MHz, DMSO-d6) 4.18 (s, 2 H), 7.52-8.16 (m, 13 H), 8.54 (s, 1 H), 10.65 (s, 1 H), 12.72 (br. s., 1 H) |
| 39 |  | 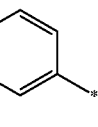 | 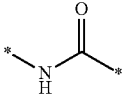 | 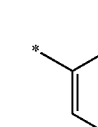 | ¹H NMR (600 MHz, DMSO-d6) 4.17 (s, 2 H), 7.32-8.16 (m, 12 H), 8.54 (s, 1 H), 10.86 (s, 1 H) |

TABLE 1-5-continued

| Example | X | Z | Y | R¹ | ¹H NMR (d ppm) |
|---|---|---|---|---|---|
| 40 | C(=O) | *-p-C₆H₄-* | *-NH-C(=O)-* | 2-OMe-C₆H₄- | ¹H NMR (600 MHz, DMSO-d6) 3.89 (s, 3 H), 4.17 (s, 2 H), 7.05-7.21 (m, 2 H), 7.50-8.16 (m, 10 H), 8.53 (s, 1 H), 10.53 (s, 1 H) |
| 41 | C(=O) | *-p-C₆H₄-* | *-NH-C(=O)-* | 2,4-diCl-C₆H₃- | ¹H NMR (600 MHz, DMSO-d6) 4.17 (s, 2 H), 7.56-8.17 (m, 11 H), 8.53 (s, 1 H), 10.97 (s, 1 H) |
| 42 | C(=O) | *-p-C₆H₄-* | *-NH-C(=O)-* | 2-Cl-5-F-C₆H₃- | ¹H NMR (600 MHz, DMSO-d6) 4.18 (s, 2 H), 7.38-8.16 (m, 11 H), 8.54 (s, 1 H), 11.00 (s, 1 H), 12.70 (br. s., 1 H) |
| 43 | C(=O) | *-p-C₆H₄-* | *-NH-C(=O)-* | 2,5-diCl-C₆H₃- | ¹H NMR (600 MHz, DMSO-d6) 4.18 (s, 2 H), 7.59-8.16 (m, 11 H), 8.54 (s, 1 H), 11.00 (br. s, 1 H), 12.66 (br. s, 1 H) |
| 44 | C(=O) | *-p-C₆H₄-* | *-NH-C(=O)-* | 2,5-diMe-C₆H₃- | ¹H NMR (600 MHz, DMSO-d6) 2.33 (s, 3 H), 2.33 (s, 3 H), 4.18 (s, 2 H), 7.18-8.16 (m, 11 H), 8.53 (s, 1 H), 10.69 (br. s, 1 H), 12.66 (br. s., 1 H) |
| 45 | C(=O) | *-p-C₆H₄-* | *-NH-C(=O)-* | 2,3,5-triCl-C₆H₂- | ¹H NMR (600 MHz, DMSO-d6) 4.18 (s, 2 H), 7.70-8.16 (m, 10 H), 8.54 (s, 1 H), 11.07 (br. s, 1 H), 12.67 (br. s., 1 H) |
| 46 | C(=O) | *-p-C₆H₄-* | *-NH-C(=O)-* | 1-naphthyl | ¹H NMR (600 MHz, DMSO-d6) 4.19 (s, 2 H), 7.58-8.21 (m, 15 H), 8.55 (s, 1 H), 11.00 (br. s, 1 H), 12.67 (br. s., 1 H) |
| 47 | C(=O) | *-p-C₆H₄-* | *-NH-C(=O)-* | 2-Cl-4-F-C₆H₃- | ¹H NMR (600 MHz, DMSO-d6) 4.17 (s, 2 H), 7.34-8.16 (m, 11 H), 8.53 (s, 1 H), 10.94 (s, 1 H) |
| 48 | C(=O) | *-p-C₆H₄-* | *-NH-C(=O)-* | 2,3,5-triCl-C₆H₂- | ¹H NMR (600 MHz, DMSO-d6) 4.17 (s, 2 H), 7.68-8.16 (m, 10 H), 8.53 (s, 1 H), 11.21 (s, 1 H), 12.71 (br. s., 1 H) |

TABLE 1-6

| Example | X | Z | Y | R[1] | $^1$H NMR (d ppm) |
|---|---|---|---|---|---|
| 49 | C(=O) | 1,4-phenylene | NHC(=O)CH2 | 4-chloro-2-fluoro-3-methylphenyl (Me, F, Cl substituents) | $^1$H NMR (600 MHz, DMSO-d6) 2.28 (s, 3 H), 4.15 (s, 2 H), 7.33-8.17 (m, 10 H), 8.52 (s, 1 H), 11.18 (s, 1 H) |
| 50 | C(=O) | 1,4-phenylene | NHC(=O)CH2 | benzofuran-2-yl | $^1$H NMR (600 MHz, DMSO-d6) 4.18 (s, 2 H), 7.36-8.16 (m, 13 H), 8.55 (s, 1 H), 10.91 (s, 1 H), 12.71 (br. s., 1 H) |
| 51 | C(=O) | 1,4-phenylene | NHC(=O)CH2 | pyridin-4-yl | $^1$H NMR (600 MHz, DMSO-d6) 4.17 (s, 2 H), 7.69-8.16 (m, 10 H), 8.54 (s, 1 H), 8.79-8.82 (m, 2 H), 10.88 (s, 1 H) |
| 52 | C(=O) | 1,4-phenylene | NHC(=O)CH2 | 2,3,4-trifluorophenyl | $^1$H NMR (600 MHz, DMSO-d6) 4.17 (s, 2 H), 7.46-8.16 (m, 10 H), 8.54 (s, 1 H), 10.95 (s, 1 H), 12.69 (br. s., 1 H) |
| 53 | C(=O) | 1,4-phenylene | NHC(=O)CH2 | 1-adamantyl | $^1$H NMR (600 MHz, DMSO-d6) 1.56-1.69 (m, 12 H), 1.90-1.96 (m, 3 H), 2.11 (s, 2 H), 4.16 (s, 2 H), 7.67-8.15 (m, 8 H), 8.52 (s, 1 H), 10.19 (br. s., 1 H), 12.67 (br. s., 1 H) |
| 54 | C(=O) | 1,4-phenylene | NHC(=O)CH2 | 5,6,7,8-tetrahydronaphthalen-2-yl | $^1$H NMR (600 MHz, DMSO-d6) 1.73-1.81 (m, 4 H), 2.76-2.85 (m, 4 H), 4.18 (s, 2 H), 7.19-8.16 (m, 1 H), 8.54 (s, 1 H), 10.51 (br. s, 1 H), 12.67 (br. s., 1 H) |
| 55 | C(=O) | 1,4-phenylene | NHC(=O)CH2 | pyrimidin-2-yl | $^1$H NMR (600 MHz, DMSO-d6) 4.14 (s, 2 H), 7.66-8.13 (m, 9 H), 8.51 (s, 1 H), 9.01-9.05 (m, 2 H), 11.10 (br. s, 1 H), 12.64 (br. s., 1 H) |
| 56 | C(=O) | 1,4-phenylene | NHC(=O)CH2 | 2,4-dichloro-5-fluorophenyl | $^1$H NMR (600 MHz, DMSO-d6) 4.17 (s, 2 H), 7.70-8.16 (m, 10 H), 8.53 (s, 1 H), 11.02 (s, 1 H) |
| 57 | C(=O) | 1,4-phenylene | NHC(=O)CH2 | 4-pentylphenyl | $^1$H NMR (600 MHz, DMSO-d6) 0.86 (t, J = 7.1 Hz, 3 H), 1.24-1.35 (m, 4 H), 1.57-1.64 (m, 2 H), 2.66 (t, J = 7.6 Hz, 2 H), 4.17 (s, 2 H), 7.34-8.16 (m, 12 H), 8.53 (s, 1 H), 10.56 (s, 1 H) |
| 58 | C(=O) | 1,4-phenylene | NHC(=O)CH2 | thiazol-4-yl | $^1$H NMR (600 MHz, DMSO-d6) 4.17 (s, 2 H), 7.69-8.59 (m, 10 H), 9.28-9.30 (m, 1 H), 10.74 (s, 1 H), 12.69 (br. s., 1 H) |

TABLE 1-7

| Example | X | Z | Y | R¹ | ¹H NMR (d ppm) |
|---|---|---|---|---|---|
| 59 |  | 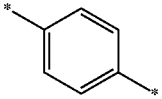 | 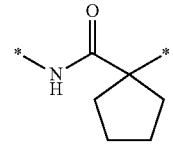 | 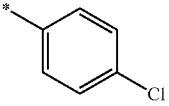 | ¹H NMR (600 MHz, DMSO-d6) 1.60-1.72 (m, 4 H), 1.89-1.97 (m, 2 H), 2.56-2.64 (m, 2 H), 4.16 (s, 2 H), 7.38-8.14 (m, 12 H), 8.51 (s, 1 H), 9.61 (s, 1 H), 12.69 (br. s., 1 H) |
| 60 |  | 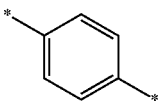 | 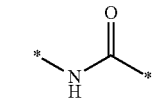 | 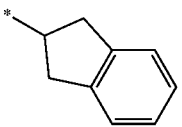 | ¹H NMR (600 MHz, DMSO-d6) 3.12-3.24 (m, 4 H), 3.42-3.49 (m, 1 H), 4.17 (s, 2 H), 7.12-8.15 (m, 12 H), 8.53 (s, 1 H), 10.48 (br. s, 1 H), 12.65 (br. s., 1 H) |
| 61 |  | 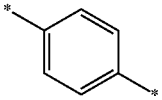 | 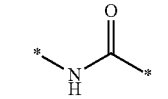 | 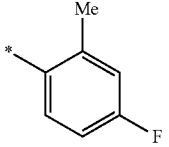 | ¹H NMR (600 MHz, DMSO-d6) 2.41 (s, 3 H), 4.18 (s, 2 H), 7.12-8.16 (m, 11 H), 8.53 (s, 1 H), 10.73 (br. s, 1 H), 12.66 (br. s., 1 H) |
| 62 |  | 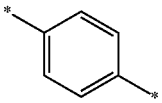 | 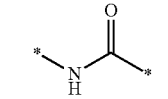 | 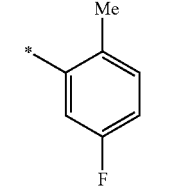 | ¹H NMR (600 MHz, DMSO-d6) 2.35 (s, 3 H), 4.18 (s, 2 H), 7.23-8.16 (m, 11 H), 8.54 (s, 1 H), 10.78 (br. s, 1 H), 12.65 (br. s., 1 H) |
| 63 |  | 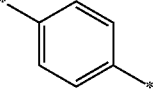 | 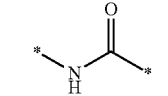 | 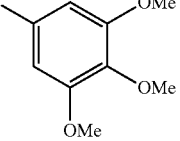 | ¹H NMR (600 MHz, DMSO-d6) 3.74 (s, 3 H), 3.88 (s, 6 H), 4.18 (s, 2 H), 7.28-8.16 (m, 10 H), 8.54 (s, 1 H), 10.50 (s, 1 H), 12.70 (br. s., 1 H) |
| 64 |  | 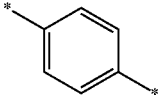 | 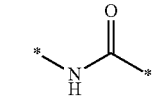 | 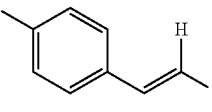 | ¹H NMR (600 MHz, DMSO-d6) 4.17 (s, 2 H), 5.42 (d, J = 11.0 Hz, 1 H), 6.01 (d, J = 17.7 Hz, 1 H), 6.83 (dd, J = 17.7, 11.0 Hz, 1 H), 7.63-8.16 (m, 12 H), 8.54 (s, 1 H), 10.62 (s, 1 H), 12.70 (br. s., 1 H) |
| 65 |  | 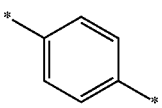 [SMILES: *c1ccc(*)cc1] | 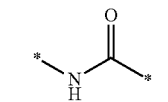 | 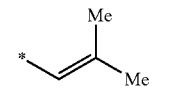 | ¹H NMR (600 MHz, DMSO-d6) 1.87-1.89 (m, 3 H), 2.16 (m, 3 H), 4.16 (s, 2 H), 5.90-5.92 (m, 1 H), 7.68-8.15 (m, 8 H), 8.52 (s, 1 H), 10.26 (s, 1 H), 12.68 (br. s., 1 H) |
| 66 |  | 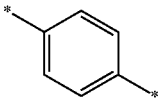 [SMILES: *c1ccc(*)cc1] | 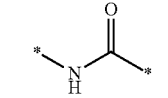 | 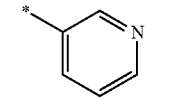 | ¹H NMR (600 MHz, DMSO-d6) 4.17 (s, 2 H), 7.57-8.34 (m, 10 H), 8.54 (s, 1 H), 8.77-8.80 (m, 1 H), 9.11-9.14 (m, 1 H), 10.83 (s, 1 H) |
| 67 |  | 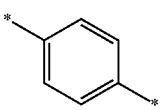 | 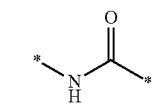 | 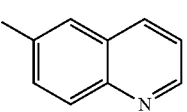 | ¹H NMR (600 MHz, DMSO-d6) 4.18 (s, 2 H), 7.63-9.05 (m, 15 H), 10.91 (br. s, 1 H), 12.67 (br. s., 1 H) |

TABLE 1-7-continued

| Example | X | Z | Y | R¹ | ¹H NMR (d ppm) |
|---|---|---|---|---|---|
| 68 | *-C(=O)-* | *-C6H4-* (para) | *-NH-C(=O)-CH2-NH-S(=O)2-* | *-C6H4-Me (para) | ¹H NMR (600 MHz, DMSO-d6) 2.34 (s, 3 H), 3.67-3.71 (m, 2 H), 4.17 (s, 2 H), 7.33-8.15 (m, 13 H), 8.52 (s, 1 H), 10.31 (br. s, 1 H), 12.62 (br. s., 1 H) |

TABLE 1-8

| Example | X | Z | Y | R¹ | ¹H NMR (d ppm) |
|---|---|---|---|---|---|
| 69 | *-C(=O)-* | *-C6H4-* (para) | *-NH-C(=O)-* | *-pyrazinyl | ¹H NMR (600 MHz, DMSO-d6) 4.18 (s, 2 H), 7.69-9.34 (m, 12 H), 11.12 (br. s, 1 H), 12.67 (br. s, 1 H) |
| 70 | *-C(=O)-* | *-C6H4-* (para) | *-NH-C(=O)-* | *-C6H3(F)(Cl) | ¹H NMR (600 MHz, DMSO-d6) 4.18 (s, 2 H), 7.35-8.16 (m, 11 H), 8.54 (s, 1 H), 10.97 (br. s, 1 H), 12.66 (br. s., 1 H) |
| 71 | *-C(=O)-* | *-C6H4-* (para) | *-NH-C(=O)-* | *-C6H4-F (meta) | ¹H NMR (600 MHz, DMSO-d6) 4.18 (s, 2 H), 7.45-8.16 (m, 12 H), 8.54 (s, 1 H), 10.70 (s, 1 H), 12.70 (br. s., 1 H) |
| 72 | *-C(=O)-* | *-C6H4-* (para) | *-NH-C(=O)-* | *-C6H4-OMe (meta) | ¹H NMR (600 MHz, DMSO-d6) 3.85 (s, 3 H), 4.18 (s, 2 H), 7.44-8.16 (m, 12 H), 8.54 (s, 1 H), 10.61 (s, 1 H), 12.68 (br. s, 1 H) |
| 73 | *-C(=O)-* | *-C6H4-* (para) | *-NH-C(=O)-* | *-C6H4-Me (meta) | ¹H NMR (600 MHz, DMSO-d6) 2.41 (s, 3 H), 4.17 (s, 2 H), 7.41-8.16 (m, 12 H), 8.54 (s, 1 H), 10.60 (s, 1 H), 12.70 (br. s, 1 H) |
| 74 | *-C(=O)-* | *-C6H4-* (para) | *-NH-C(=O)-* | *-C6H4-S(=O)2-Me (para) | ¹H NMR (600 MHz, DMSO-d6) 3.31 (s, 3 H), 4.18 (s, 2 H), 7.70-8.22 (m, 12 H), 8.54 (s, 1 H), 10.88 (br. s, 1 H), 12.67 (br. s, 1 H) |
| 75 | *-C(=O)-* | *-C6H4-* (para) | *-NH-C(=O)-* | *-C6H4-Br (meta) | ¹H NMR (600 MHz, DMSO-d6) 4.18 (s, 2 H), 7.50-8.18 (m, 12 H), 8.54 (s, 1 H), 10.72 (br. s, 1 H), 12.66 (br. s., 1 H) |
| 76 | *-C(=O)-* | *-C6H4-* (para) | *-NH-C(=O)-* | *-cyclohexyl | ¹H NMR (600 MHz, DMSO-d6) 1.14-1.84 (m, 10 H), 2.34-2.40 (m, 1 H), 4.16 (s, 2 H), 7.67-8.15 (m, 8 H), 8.52 (s, 1 H), 10.24 (br. s, 1 H), 12.67 (br. s., 1 H) |
| 77 | *-C(=O)-* | *-C6H4-* (para) | *-NH-C(=O)-CH2-CH2-* | *-cyclohexyl | ¹H NMR (600 MHz, DMSO-d6) 0.84-1.27 (m, 6 H), 1.47-1.53 (m, 2 H), 1.57-1.73 (m, 5 H), 2.34-2.39 (m, 2 H), 4.17 (s, 2 H), 7.68-8.15 (m, 8 H), 8.52 (s, 1 H), 10.30 (br. s, 1 H), 12.66 (br. s, 1 H) |

TABLE 1-8-continued

| Example | X | Z | Y | R¹ | ¹H NMR (d ppm) |
|---|---|---|---|---|---|
| 78 | C(=O) | 1,4-phenylene | -NH-C(=O)-C(Me)=CH- | phenyl | ¹H NMR (600 MHz, DMSO-d6) 2.12 (s, 3 H), 4.17 (s, 2 H), 7.34-8.16 (m, 14 H), 8.53 (s, 1 H), 10.36 (s, 1 H), 12.71 (br. s., 1 H) |
| 79 | C(=O) | 1,4-phenylene | -NH-C(=O)- | 4-carboxyphenyl | ¹H NMR (600 MHz, DMSO-d6) 4.18 (s, 2 H), 7.70-8.16 (m, 12 H), 8.54 (s, 1 H), 10.80 (s, 1 H) |

TABLE 1-9

| Example | X | Z | Y | R¹ | ¹H NMR (d ppm) |
|---|---|---|---|---|---|
| 80 | C(=O) | 1,4-phenylene | -NH-C(=O)-(CH2)3- | Me | ¹H NMR (600 MHz, DMSO-d6) 0.90 (t, J = 7.6 Hz, 3 H), 1.28-1.37 (m, 2 H), 1.54-1.61 (m, 2 H), 2.36 (t, J = 7.6 Hz, 2 H), 4.16 (s, 2 H), 7.67-8.15 (m, 8 H), 8.52 (s, 1 H), 10.30 (s, 1 H), 12.69 (br. s., 1 H) |
| 81 | C(=O) | 1,4-phenylene | -NH-C(=O)- | tetrahydropyran-4-yl | ¹H NMR (600 MHz, DMSO-d6) 1.61-1.75 (m, 4 H), 2.60-2.67 (m, 1 H), 3.32-3.37 (m, 2 H), 3.88-3.94 (m, 2 H), 4.16 (s, 2 H), 7.67-8.16 (m, 8 H), 8.52 (s, 1 H), 10.33 (s, 1 H), 12.69 (br. s., 1 H) |
| 82 | C(=O) | 1,4-phenylene | -NH-C(=O)-cyclohexylene- | 4-chlorophenyl | ¹H NMR (600 MHz, DMSO-d6) 1.40-1.65 (m, 4 H), 1.83-2.02 (m, 4 H), 2.42-2.49 (m, 1 H), 2.53-2.60 (m, 1 H), 4.16 (s, 2 H), 7.26-7.36 (m, 4 H), 7.68-8.15 (m, 8 H), 8.52 (s, 1 H), 10.34 (s, 1 H), 12.69 (br. s., 1 H) |
| 83 | C(=O) | 1,4-phenylene | -NH-C(=O)-CH=CH- | 4-fluorophenyl | ¹H NMR (600 MHz, DMSO-d6) 4.17 (s, 2 H), 6.78-8.16 (m, 14 H), 8.53 (s, 1 H), 10.63 (s, 1 H), 12.69 (br. s., 1 H) |
| 84 | C(=O) | 1,4-phenylene | -NH-C(=O)-CH=CH- | 4-methoxyphenyl | ¹H NMR (600 MHz, DMSO-d6) 3.81 (s, 3 H), 4.17 (s, 2 H), 6.72 (d, J = 15.6 Hz, 1 H), 7.00-7.04 (m, 2 H), 7.57-8.15 (m, 9 H), 8.53 (s, 1 H), 10.55 (s, 1 H), 12.62 (br. s., 1 H) |
| 85 | C(=O) | 1,4-phenylene | -NH-C(=O)- | 1H-indol-3-yl | ¹H NMR (600 MHz, DMSO-d6) 4.17 (s, 2 H), 7.14-8.39 (m, 13 H), 8.54 (s, 1 H), 10.12 (s, 1 H), 11.79-11.88 (m, 1 H), 12.70 (br. s., 1 H) |
| 86 | C(=O) | 1,4-phenylene | -NH-C(=O)- | quinoxalin-2-yl | ¹H NMR (600 MHz, DMSO-d6) 4.12 (s, 2 H), 7.69-8.35 (m, 12 H), 8.53 (s, 1 H), 9.57 (s, 1 H), 11.22 (s, 1 H) |

TABLE 1-9-continued

| Example | X | Z | Y | R¹ | ¹H NMR (d ppm) |
|---|---|---|---|---|---|
| 87 | C(=O) | *-C₆H₄-* (para) | *-NH-C(=O)-CH₂-O-* | *-C₆H₄-Cl (para) | ¹H NMR (600 MHz, DMSO-d6) 4.07 (s, 2 H), 4.77 (s, 2 H), 7.00-8.20 (m, 12 H), 8.49 (s, 1 H), 10.55 (s, 1 H) |
| 88 | C(=O) | *-C₆H₄-* (para) | *-NH-C(=O)-* | *-benzo[b]thiophen-3-yl | ¹H NMR (600 MHz, DMSO-d6) 4.18 (s, 2 H), 7.44-8.45 (m, 12 H), 8.55 (s, 1 H), 8.67 (s, 1 H), 10.74 (s, 1 H), 12.70 (br. s., 1 H) |
| 89 | C(=O) | *-C₆H₄-* (para) | *-NH-C(=O)-* | *-C₆H₄-OH (para) | ¹H NMR (600 MHz, DMSO-d6) 4.17 (s, 2 H), 6.85-6.90 (m, 2 H), 7.68-8.16 (m, 10 H), 8.53 (s, 1 H), 10.19 (br. s., 1 H), 10.38 (s, 1 H), 12.69 (br. s., 1 H) |

TABLE 1-10

| Example | X | Z | Y | R¹ | ¹H NMR (d ppm) |
|---|---|---|---|---|---|
| 90 | C(=O) | *-C₆H₄-* (para) | *-NH-C(=O)-* | *-cyclohex-1-enyl | ¹H NMR (600 MHz, DMSO-d6) 1.54-1.66 (m, 4 H), 2.17-2.29 (m, 4 H), 4.17 (s, 2 H), 6.71-6.75 (m, 1 H), 7.68-8.15 (m, 8 H), 8.52 (s, 1 H), 10.01 (br. s., 1 H), 12.66 (br. s., 1 H) |
| 91 | C(=O) | *-C₆H₄-* (para) | *-NH-C(=O)-* | *-C₆H₄-C(=O)-C₆H₅ (para) | ¹H NMR (600 MHz, DMSO-d6) 4.18 (s, 2 H), 7.57-8.16 (m, 17 H), 8.55 (s, 1 H), 10.84 (br. s., 1 H), 12.67 (br. s., 1 H) |
| 92 | C(=O) | *-C₆H₄-* (para) | *-NH-C(=O)-* | *-5-chloro-1H-indol-2-yl | ¹H NMR (600 MHz, DMSO-d6) 4.18 (s, 2 H), 7.23-8.17 (m, 12 H), 8.55 (s, 1 H), 10.67 (br. s., 1 H), 12.02 (br. s, 1 H), 12.67 (br. s., 1 H) |
| 93 | C(=O) | *-C₆H₄-* (para) | *-NH-C(=O)-* | *-quinolin-2-yl | ¹H NMR (600 MHz, DMSO-d6) 4.19 (s, 2 H), 7.71-8.68 (m, 15 H), 11.13 (br. s, 1 H), 12.68 (br. s., 1 H) |
| 94 | C(=O) | *-C₆H₄-* (para) | *-NH-C(=O)-* | *-4,5,6,7-tetrahydro-1H-indol-2-yl | ¹H NMR (600 MHz, DMSO-d6) 1.65-1.75 (m, 4 H), 2.43-2.47 (m, 2 H), 2.53-2.57 (m, 2 H), 4.16 (s, 2 H), 6.87-6.89 (m, 1 H), 7.67-8.15 (m, 8 H), 8.52 (s, 1 H), 9.92 (s, 1 H), 11.25 (s, 1 H) |
| 95 | C(=O) | *-C₆H₄-* (para) | *-NH-C(=O)-* | *-1H-pyrrolo[2,3-b]pyridin-3-yl | ¹H NMR (600 MHz, DMSO-d6) 4.16 (s, 2 H), 7.22-7.25 (m, 1 H), 7.69-8.54 (m, 12 H), 10.22 (s, 1 H), 12.34-12.37 (m, 1 H), 12.71 (br. s., 1 H) |

TABLE 1-10-continued

| Example | X | Z | Y | R¹ | ¹H NMR (d ppm) |
|---|---|---|---|---|---|
| 96 | C(=O) | 1,4-phenylene | NHC(=O) | 5-methoxy-1H-indol-2-yl | ¹H NMR (600 MHz, DMSO-d6) 3.78 (s, 3 H), 4.15 (s, 2 H), 6.88-8.18 (m, 12 H), 8.53 (s, 1 H), 10.55 (s, 1 H), 11.68 (s, 1 H), 12.72 (br. s., 1 H) |
| 97 | C(=O) | 1,4-phenylene | NHC(=O) | 1H-imidazol-4-yl | ¹H NMR (600 MHz, DMSO-d6) 4.17 (s, 2 H), 7.68-8.15 (m, 10 H), 8.53 (s, 1 H), 10.24 (br. s., 1 H), 12.66 (br. s., 1 H), 12.71 (br. s., 1 H) |
| 98 | C(=O) | 1,4-phenylene | NHC(=O) | pyridazin-3-yl | ¹H NMR (600 MHz, DMSO-d6) 4.18 (s, 2 H), 7.70-8.36 (m, 10 H), 8.55 (s, 1 H), 9.48-9.51 (m, 1 H), 11.46 (br. s, 1 H), 12.67 (br. s., 1 H) |
| 99 | C(=O) | 1,4-phenylene | NHC(=O) | 3-chloro-4-methylphenyl | ¹H NMR (600 MHz, DMSO-d6) 2.42 (s, 3 H), 4.18 (s, 2 H), 7.52-8.16 (m, 11 H), 8.54 (s, 1 H), 10.65 (br. s, H), 12.67 (br. s., 1 H) |

TABLE 1-11

| Example | X | Z | Y | R¹ | ¹H NMR (d ppm) |
|---|---|---|---|---|---|
| 100 | C(=O) | 1,4-phenylene | NHC(=O) | 2-methoxy-4-methylphenyl | ¹H NMR (600 MHz, DMSO-d6) 2.23 (s, 3 H), 3.89 (s, 3 H), 4.18 (s, 2 H), 7.29-8.16 (m, 11 H), 8.54 (s, 1 H), 10.53 (br. s, 1 H), 12.68 (br. s., 1 H) |
| 101 | C(=O) | 1,4-phenylene | NHC(=O) | 3,4-dimethylphenyl | ¹H NMR (600 MHz, DMSO-d6) 2.30 (s, 3 H), 2.32 (s, 3 H), 4.18 (s, 2 H), 7.29-8.16 (m, 11 H), 8.54 (s, 1 H), 10.52 (br. s., 1 H), 12.67 (br. s., 1 H) |
| 102 | C(=O) | 1,4-phenylene | NHC(=O) | 5-methylbenzothiophen-2-yl | ¹H NMR (600 MHz, DMSO-d6) 2.46 (s, 3 H), 4.18 (s, 2 H), 7.33-8.56 (m, 13 H), 10.86 (br. s, 1 H), 12.68 (br. s., 1 H) |
| 103 | C(=O) | 1,4-phenylene | NHC(=O) | 3,5-dimethylphenyl | ¹H NMR (600 MHz, DMSO-d6) 2.34-2.39 (m, 6 H), 4.17 (s, 2 H), 7.23-8.16 (m, 11 H), 8.54 (s, 1 H), 10.56 (br. s, 1 H), 12.71 (br. s., 1 H) |
| 104 | C(=O) | 1,4-phenylene | NHC(=O) | quinolin-8-yl | ¹H NMR (600 MHz, DMSO-d6) 4.18 (s, 2 H), 7.70-9.19 (m, 15 H), 12.71 (br. s., 1 H), 13.53 (s, 1 H) |
| 105 | C(=O) | 1,4-phenylene | NHC(=O) | 1,8-naphthyridin-2-yl | ¹H NMR (600 MHz, DMSO-d6) 4.15 (s, 2 H), 7.69-9.28 (m, 14 H), 11.22 (br. s, 1 H) |

TABLE 1-11-continued

| Example | X | Z | Y | R¹ | ¹H NMR (d ppm) |
|---|---|---|---|---|---|
| 106 |  | 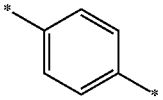 | 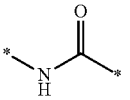 | 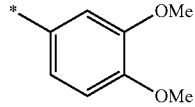 | ¹H NMR (600 MHz, DMSO-d6) 3.85 (s, 3 H), 3.85 (s, 3 H), 4.15 (s, 2 H), 7.08-8.17 (m, 11 H), 8.53 (s, 1 H), 10.46 (br. s, 1 H), 12.74 (br. s., 1 H) |
| 107 |  | 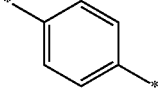 | 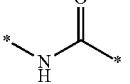 | 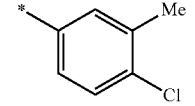 | ¹H NMR (600 MHz, DMSO-d6) 2.43 (s, 3 H), 4.17 (s, 2 H), 7.58-8.16 (m, 11 H), 8.53 (s, 1 H), 10.66 (br. s, 1 H), 12.71 (br. s., 1 H) |
| 108 |  | 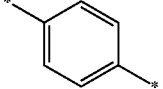 | 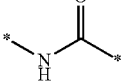 | 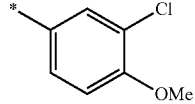 | ¹H NMR (600 MHz, DMSO-d6) 3.95 (s, 3 H), 4.16 (s, 2 H), 7.29-8.17 (m, 11 H), 8.53 (s, 1 H), 10.56 (br. s, 1 H) |
| 109 |  | 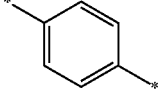 | 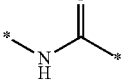 | 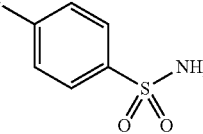 | ¹H NMR (600 MHz, DMSO-d6) 4.18 (s, 2 H), 7.53 (br. s, 2 H), 7.70-8.16 (m, 12 H), 8.54 (s, 1 H), 10.81 (br. s, 1 H), 12.67 (br. s., 1 H) |
| 110 |  | 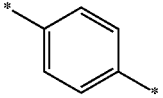 | 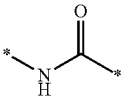 | 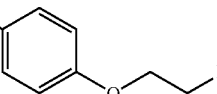 | ¹H NMR (600 MHz, DMSO-d6) 0.99 (t, J = 7.3 Hz, 3 H), 1.72-1.80 (m, 2 H), 4.03 (t, J = 6.4 Hz, 2 H), 4.16 (s, 2 H), 7.05-8.17 (m, 12 H), 8.53 (s, 1 H), 10.47 (br. s, 1 H) |

TABLE 1-12

| Example | X | Z | Y | R¹ | ¹H NMR (d ppm) |
|---|---|---|---|---|---|
| 111 |  | 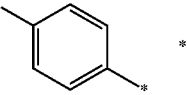 | 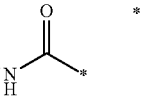 | 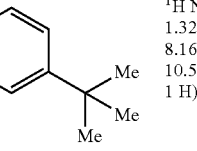 | ¹H NMR (600 MHz, DMSO-d6) 1.32 (s, 9 H), 4.17 (s, 2 H), 7.54-8.16 (m, 12 H), 8.54 (s, 1 H), 10.57 (br. s, 1 H), 12.70 (br. s., 1 H) |
| 112 |  | 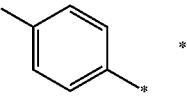 | 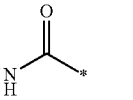 | 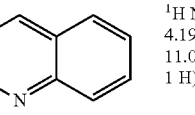 | ¹H NMR (600 MHz, DMSO-d6) 4.19 (s, 2 H), 7.70-9.39 (m, 15 H), 11.00 (br. s, 1 H), 12.68 (br. s., 1 H) |
| 113 |  | 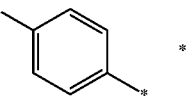 | 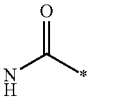 | 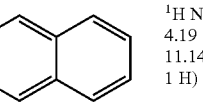 | ¹H NMR (600 MHz, DMSO-d6) 4.19 (s, 2 H), 7.70-9.51 (m, 15 H), 11.14 (br. s, 1 H), 12.69 (br. s., 1 H) |
| 114 |  | 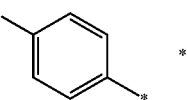 | 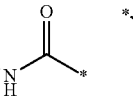 | 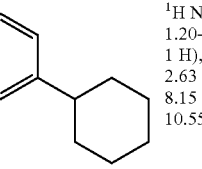 | ¹H NMR (600 MHz, DMSO-d6) 1.20-1.49 (m, 5 H), 1.68-1.74 (m, 1 H), 1.77-1.83 (m, 4 H), 2.58-2.63 (m, 1 H), 4.16 (s, 2 H), 7.36-8.15 (m, 12 H), 8.53 (s, 1 H), 10.55 (br. s, 1 H) |
| 115 |  | 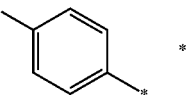 | 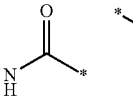 | 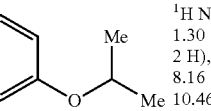 | ¹H NMR (600 MHz, DMSO-d6) 1.30 (d, J = 6.0 Hz, 6 H), 4.16 (s, 2 H), 4.71-4.79 (m, 1 H), 7.02-8.16 (m, 12 H), 8.53 (s, 1 H), 10.46 (br. s, 1 H) |

TABLE 1-12-continued

| Example | X | Z | Y | R¹ | ¹H NMR (d ppm) |
|---|---|---|---|---|---|
| 116 |  | 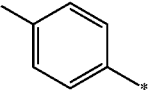 | 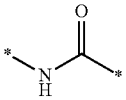 | 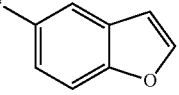 | ¹H NMR (600 MHz, DMSO-d6) 4.17 (s, 2 H), 7.12-7.14 (m, 1 H), 7.70-8.16 (m, 11 H), 8.34-8.35 (m, 1 H), 8.54 (s, 1 H), 10.69 (s, 1 H), 12.72 (br. s., 1 H) |
| 117 |  | 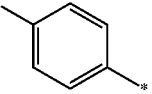 | 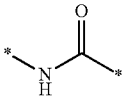 | 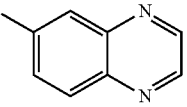 | ¹H NMR (600 MHz, DMSO-d6) 4.18 (s, 2 H), 7.70-9.10 (m, 14 H), 11.02 (s, 1 H), 12.70 (br. s., 1 H) |
| 118 |  | 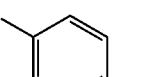 | 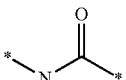 | 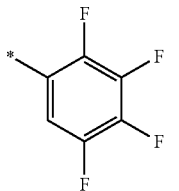 | ¹H NMR (600 MHz, DMSO-d6) 3.95 (s, 2 H), 7.64-8.26 (m, 9 H), 8.47 (s, 1 H), 11.06 (br. s., 1 H) |
| 119 |  | 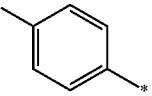 | 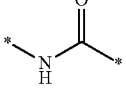 | 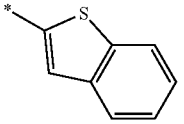 | ¹H NMR (600 MHz, DMSO-d6) 4.18 (s, 2 H), 7.46-8.56 (m, 14 H), 10.90 (br. s, 1 H), 12.71 (br. s., 1 H) |
| 120 |  | 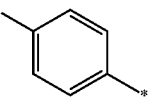 | 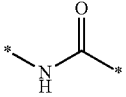 | 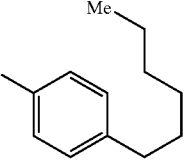 | ¹H NMR (600 MHz, DMSO-d6) 0.82-0.88 (m, 3 H), 1.24-1.33 (m, 6 H), 1.57-1.63 (m, 2 H), 2.63-2.69 (m, 2 H), 4.17 (s, 2 H), 7.34-8.16 (m, 12 H), 8.53 (s, 1 H), 10.56 (s, 1 H) |
| 121 |  | 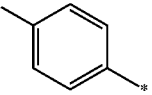 | 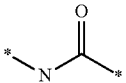 | 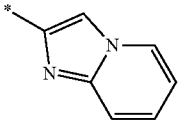 | ¹H NMR (600 MHz, DMSO-d6) 4.18 (s, 2 H), 7.02-8.66 (m, 14 H), 10.71 (br. s., 1 H), 12.67 (br. s., 1 H) |

TABLE 1-13

| Example | X | Z | Y | R¹ | ¹H NMR (d ppm) |
|---|---|---|---|---|---|
| 122 |  | 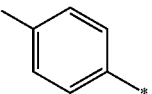 | 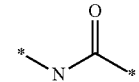 | 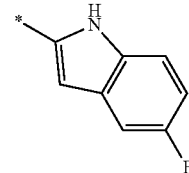 | ¹H NMR (600 MHz, DMSO-d6) 4.18 (s, 2 H), 7.08-8.17 (m, 12 H), 8.54 (s, 1 H), 10.63 (br. s., 1 H), 11.92 (br. s, 1 H), 12.67 (br. s., 1 H) |
| 123 |  | 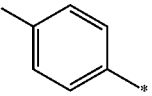 | 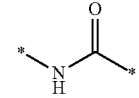 | 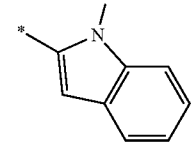 | ¹H NMR (600 MHz, DMSO-d6) 4.03 (s, 3 H), 4.18 (s, 2 H), 7.12-8.16 (m, 13 H), 8.55 (s, 1 H), 10.69 (br. s, 1 H), 12.68 (br. s., 1 H) |
| 124 |  | 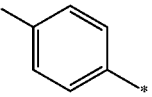 | 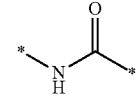 | 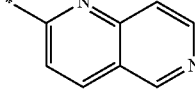 | ¹H NMR (600 MHz, DMSO-d6) 4.18 (s, 2 H), 7.69-9.60 (m, 14 H), 11.22 (br. s., 1 H), 12.68 (br. s., 1 H) |

TABLE 1-13-continued

| Example | X | Z | Y | R[1] | $^1$H NMR (d ppm) |
|---|---|---|---|---|---|
| 125 | 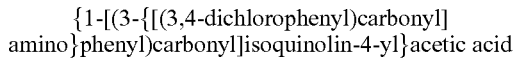 | | | | $^1$H NMR (600 MHz, DMSO-d6) 2.33 (s, 3 H), 4.17 (s, 2 H), 7.69-8.16 (m, 8 H), 8.54 (s, 1 H), 11.34 (br. s, 1 H), 12.71 (br. s., 1 H) |
| 126 | 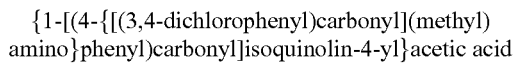 | | | 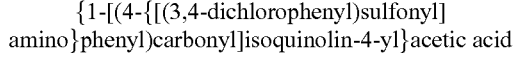 | $^1$H NMR (600 MHz, DMSO-d6) 3.74-3.85 (m, 4 H), 7.56-8.43 (m, 14 H), 10.56 (s, 1 H), 10.93 (s, 1 H) |

Example 127

{1-[(3-{[(3,4-dichlorophenyl)carbonyl]amino}phenyl)carbonyl]isoquinolin-4-yl}acetic acid (1) The same procedure as used in Example 1-(2) was carried out using [3-(cyanomethyl)phenyl]carbamic acid 1,1-dimethylethyl ester (2.32 g) to give methyl 1-({3-[(tert-butoxycarbonyl)amino]phenyl}carbonyl)isoquinoline-4-carboxylate (3.59 g) as a pale yellow amorphous substance.

$^1$H NMR (600 MHz, CHLOROFORM-d) d ppm 1.49 (s, 9H), 4.07 (s, 3H), 6.58 (br. s., 1H), 7.36-8.16 (m, 7H), 8.99-9.04 (m, 1H), 9.19 (s, 1H)

(2) The same procedure as used in Example 1-(3) was carried out using the compound (3.59 g) obtained in Example 127-(1) to give 1-({3-[(tert-butoxycarbonyl)amino]phenyl}carbonyl)isoquinoline-4-carboxylic acid (3.46 g) as a pale yellow amorphous substance.

$^1$H NMR (600 MHz, CHLOROFORM-d) d ppm 1.49 (s, 9H), 6.79 (br. s., 1H), 7.39-8.18 (m, 7H), 9.09-9.13 (m, 1H), 9.35 (s, 1H)

(3) The same procedure as used in Example 1-(4) was carried out using the compound (3.46 g) obtained in Example 127-(2) to give methyl[1-({3-[(tert-butoxycarbonyl)amino]phenyl}carbonyl)isoquinolin-4-yl]acetate (1.03 g) as a pale yellow solid.

$^1$H NMR (600 MHz, CHLOROFORM-d) d ppm 1.50 (s, 9H), 3.73 (s, 3H), 4.11 (s, 2H), 6.56 (br. s., 1H), 7.40 (s, 8H), 8.51 (s, 1H)

(4) The same procedure as used in Example 2-(1) was carried out using the compound (1.03 g) obtained in Example 127-(3) to give methyl{1-[(3-aminophenyl)carbonyl]isoquinolin-4-yl}acetate (534 mg) as a yellow solid.

$^1$H NMR (600 MHz, CHLOROFORM-d) d ppm 3.73 (s, 3H), 3.79 (br. s., 2H), 4.10 (s, 2H), 6.84-8.21 (m, 8H), 8.51 (s, 1H)

(5) The same procedure as used in Example 2-(2) was carried out using the compound (320 mg) obtained in Example 127-(4) and 3,4-dichlorobenzoyl chloride to give methyl{1-[(3-{[(3,4-dichlorophenyl)carbonyl]amino}phenyl)carbonyl]isoquinolin-4-yl}acetate (438 mg) as a pale yellow amorphous substance.

$^1$H NMR (600 MHz, CHLOROFORM-d) d ppm 3.75 (s, 3H), 4.08 (s, 2H), 7.33-8.43 (m, 12H), 8.45 (s, 1H)

(6) The same procedure as used in Example 2-(3) was carried out using the compound (438 mg) obtained in Example 127-(5) to give the titled compound (178 mg) as a pale yellow solid.

Example 128

{1-[(4-{[(3,4-dichlorophenyl)carbonyl](methyl)amino}phenyl)carbonyl]isoquinolin-4-yl}acetic acid To a suspension of sodium hydride (48 mg, oiliness: 60%) in tetrahydrofuran (4 ml), the compound (190 mg) obtained in Example 2-(3) was added in an ice bath, and the mixture was stirred at room temperature for one hour. To the reaction solution, iodomethane (0.5 ml) was added, and the mixed solution was stirred at room temperature for three hours. To the solution, 2N aqueous hydrochloric acid solution was added, followed by extraction with ethyl acetate. The organic layer was washed with a saturated saline solution, dried over anhydrous magnesium sulfate, and then evaporated under reduced pressure to remove the solvent. To the resulting crude product, diethyl ether was added, and the mixture was stirred. The precipitate was filtered and dried to give the titled compound (60 mg) as a colorless solid.

Example 129

{1-[(4-{[(3,4-dichlorophenyl)sulfonyl]amino}phenyl)carbonyl]isoquinolin-4-yl}acetic acid (1) To a solution of the compound (320 mg) obtained in Example 2-(1) in pyridine (5 ml), 3,4-dichlorobenzenesulfonyl chloride (368 mg) was added in an ice bath, and the mixed solution was stirred at room temperature for one hour. Furthermore, 3,4-dichlorobenzenesulfonyl chloride (368 mg) was added thereto, and the resulting solution was stirred at room temperature for one hour. Ethyl acetate was added, the resulting solution was washed with water, and then washed with a saturated saline solution. The organic layer was dried over anhydrous magnesium sulfate, and evaporated under reduced pressure to remove the solvent. The resulting crude product was purified by column chromatography (neutral OH type silica gel, ethyl acetate/chloroform=0 to 40%) to give methyl {1-[(4-{[(3,4-dichlorophenyl)sulfonyl]amino}phenyl)carbonyl]isoquinolin-4-yl}acetate (207 mg) as a pale yellow amorphous substance.

$^1$H NMR (600 MHz, CHLOROFORM-d) d ppm 3.73 (s, 3H), 4.11 (s, 2H), 7.11-8.24 (m, 12H), 8.49 (s, 1H)

(2) The same procedure as used in Example 2-(3) was carried out using the compound (207 mg) obtained in Example 129-(1) to give the titled compound (24 mg) as a colorless solid.

Example 130

{1-[(4-{[(3,4-dichlorophenyl)carbamoyl]amino}phenyl)carbonyl]isoquinolin-4-yl}acetic acid

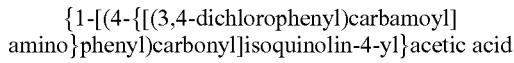

(1) To a solution of the compound (320 mg) obtained in Example 2-(1) in N,N-dimethylformamide (3 ml), a solution of 3,4-dichlorophenyl isocyanate (282 mg) in N,N-dimethylformamide (2 ml) was added in an ice bath. The mixed solution was stirred at room temperature for one hour. To the resulting solution, ethyl acetate was added, and the resulting solution was washed with water, and then washed with a saturated saline solution. The organic layer was dried over anhydrous magnesium sulfate, and evaporated under reduced pressure to remove the solvent. The resulting crude product was purified by column chromatography (neutral OH type silica gel, ethyl acetate/chloroform=0 to 70%) to give methyl {1-[(4-{[(3,4-dichlorophenyl)carbamoyl]amino}phenyl)carbonyl]isoquinolin-4-yl}acetate (287 mg) as a colorless solid.

$^1$H NMR (600 MHz, DMSO-$d_6$) d ppm 3.67 (s, 3H), 4.29 (s, 2H), 7.33-8.15 (m, 11H), 8.54 (s, 1H), 9.19 (br. s., 1H), 9.42 (br. s., 1H)

(2) The same procedure as used in Example 2-(3) was carried out using the compound (287 mg) obtained in Example 130-(1) to give the titled compound (248 mg) as a yellow solid.

Example 131

(1-{[4-({[(3,4-dichlorobenzyl)oxy]carbonyl}amino)phenyl]carbonyl}isoquinolin-4-yl)acetic acid

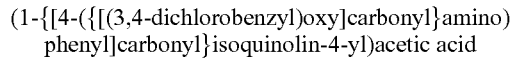

(1) To a solution of the compound (320 mg) obtained in Example 2-(1) in chloroform (5 ml), pyridine (0.324 ml) and phenyl chloroformate (0.189 ml) were added in an ice bath, and the mixed solution was stirred at room temperature for one hour. The resulting solution was evaporated under reduced pressure to remove the solvent to give methyl [1-({4-[(phenoxycarbonyl)amino]phenyl}carbonyl)isoquinolin-4-yl]acetate (440 mg) as a brownish-colored oily substance.

$^1$H NMR (600 MHz, CHLOROFORM-d) d ppm 3.73 (s, 3H), 4.11 (s, 2H), 7.13-8.23 (m, 14H), 8.52 (s, 1H)

(2) To a solution of the compound (440 mg) obtained in Example 131-(1) in tetrahydrofuran (10 ml), 3,4-dichlorobenzyl alcohol (354 mg) and N,N-diisopropyl ethyl amine (0.680 ml) were added, and the mixed solution was refluxed for eight hours. Furthermore, 3,4-dichlorobenzyl alcohol (354 mg) was added thereto, and the resulting solution was refluxed for eight hours. The solution was returned to room temperature, and ethyl acetate was added thereto. The resulting solution was washed with water, and then washed with a saturated saline solution. The organic layer was dried over anhydrous magnesium sulfate and evaporated under reduced pressure to remove the solvent. The resulting crude product was purified by column chromatography (neutral OH type silica gel, ethyl acetate/n-hexane=0 to 50%) to give methyl (1-{[4-({[(3,4-dichlorobenzyl)oxy]carbonyl}amino)phenyl]carbonyl}isoquinolin-4-yl)acetate (280 mg) as a pale yellow amorphous substance.

$^1$H NMR (600 MHz, CHLOROFORM-d) d ppm 3.73 (s, 3H), 4.11 (s, 2H), 5.15 (s, 2H), 6.99 (br. s., 1H), 7.20-8.25 (m, 11H), 8.51 (s, 1H)

(3) The same procedure as used in Example 2-(3) was carried out using the compound (280 mg) obtained in Example 131-(2) to give the titled compound (235 mg) as a pale yellow solid.

Example 132

{1-[(4-{[(3,4-dichlorobenzyl)carbamoyl]amino}phenyl)carbonyl]isoquinolin-4-yl}acetic acid

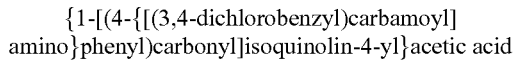

(1) To a solution of the compound (440 mg) obtained in Example 131-(1) in tetrahydrofuran (5 ml), 3,4-dichlorobenzylamine (0.397 ml) was added, and the mixed solution was stirred at 80° C. for five hours. The solution was returned to room temperature, and ethyl acetate was added thereto. The resulting solution was washed with water and then washed with a saturated saline solution. The organic layer was dried over anhydrous magnesium sulfate, and evaporated under reduced pressure to remove the solvent. The resulting crude product was purified by column chromatography (neutral OH type silica gel, methanol/chloroform=0 to 5%) to give methyl {1-[(4-{[(3,4-dichlorobenzyl)carbamoyl]amino}phenyl)carbonyl]isoquinolin-4-yl}acetate (233 mg) as a pale yellow solid.

$^1$H NMR (600 MHz, DMSO-$d_6$) d ppm 3.66 (s, 3H), 4.23-4.34 (m, 4H), 7.08 (br. s., 1H), 7.27-8.15 (m, 11H), 8.53 (s, 1H), 9.40 (br. s., 1H)

(2) The same procedure as used in Example 2-(3) was carried out using the compound (233 mg) obtained in Example 132-(1) to give the titled compound (60 mg) as a yellow solid.

Example 133

[1-({4-[(3,4-dichlorobenzyl)amino]phenyl}carbonyl)isoquinolin-4-yl]acetic acid

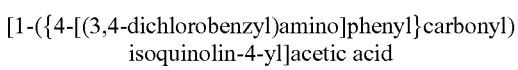

(1) To a solution of the compound (180 mg) obtained in Example 2-(1) in N,N-dimethylformamide (6 ml), 3,4-dichlorobenzyl bromide (162 mg) and potassium carbonate (93 mg) were added, and the mixed solution was refluxed for five hours. Furthermore, 3,4-dichlorobenzyl bromide (162 mg) was added thereto, and the resulting solution was refluxed for one hour. The resulting solution was returned to room temperature, and the ethyl acetate was added to the solution. The resulting solution was washed with water and then washed with a saturated saline solution. The organic layer was dried over anhydrous magnesium sulfate, and evaporated under reduced pressure to remove the solvent. The resulting crude product was purified by column chromatography (neutral OH type silica gel, ethyl acetate/n-hexane=0 to 50%) to give methyl [1-({4-[(3,4-dichlorobenzyl)amino]phenyl}carbonyl)isoquinolin-4-yl]acetate (94 mg) as a yellow amorphous substance.

$^1$H NMR (600 MHz, DMSO-$d_6$) d ppm 3.65 (s, 3H), 4.25 (s, 2H), 4.38-4.41 (m, 2H), 6.62-6.66 (m, 2H), 7.29-8.09 (m, 10H), 8.47 (s, 1H)

(2) The same procedure as used in Example 2-(3) was carried out using the compound (94 mg) obtained in Example 133-(1) to give the titled compound (53 mg) as a yellow solid.

Example 134

[1-({4-[(3,4-dichlorobenzyl)oxy]phenyl}carbonyl)isoquinolin-4-yl]acetic acid

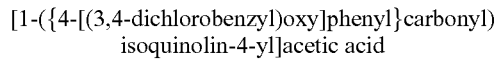

(1) The same procedure as used in Example 1-(2) was carried out using 4-methoxybenzyl cyanide (2.94 g) to give methyl 1-[(4-methoxyphenyl)carbonyl]isoquinoline-4-carboxylate (5.42 g).

¹H NMR (600 MHz, CHLOROFORM-d) d ppm 3.88 (s, 3H), 4.07 (s, 3H), 6.91-6.98 (m, 2H), 7.62-8.16 (m, 5H), 8.99-9.03 (m, 1H), 9.20 (s, 1H)

(2) The same procedure as used in Example 1-(3) was carried out using the compound (3.00 g) obtained in Example 134-(1) to give 1-[(4-methoxyphenyl)carbonyl]isoquinoline-4-carboxylic acid (1.97 g) as a brownish-colored solid.

¹H NMR (600 MHz, DMSO-d₆) d ppm 3.86 (s, 3H), 7.05-7.10 (m, 2H), 7.72-8.01 (m, 5H), 8.97-9.01 (m, 1H), 9.10 (s, 1H), 13.79 (br. s., 1H)

(3) The same procedure as used in Example 1-(4) was carried out using the compound (1.97 g) obtained in Example 134-(2) to give methyl {1-[(4-methoxyphenyl)carbonyl]isoquinolin-4-yl}acetate (1.03 g) as a pale brownish-colored solid.

¹H NMR (600 MHz, CHLOROFORM-d) d ppm 3.73 (s, 3H), 3.88 (s, 3H), 4.11 (s, 2H), 6.92-6.97 (m, 2H), 7.59-8.23 (m, 6H), 8.51 (s, 1H)

(4) To a solution of the compound (1.03 g) obtained in Example 134-(3) in chloroform (30 ml), a solution of boron tribromide (3.70 ml) in chloroform (30 ml) was added dropwise in an ice bath, and the mixed solution was stirred at room temperature for two hours. Methanol was added dropwise thereto in an ice bath, and the reaction solution was washed with water and then washed with a saturated saline solution. The organic layer was dried over anhydrous magnesium sulfate, and evaporated under reduced pressure to remove the solvent. The resulting crude product was purified by column chromatography (neutral OH type silica gel, methanol/chloroform=0 to 5%) to give methyl {1-[(4-hydroxyphenyl)carbonyl]isoquinolin-4-yl}acetate (463 mg) as a yellow solid.

¹H NMR (600 MHz, CHLOROFORM-d) d ppm 3.74 (s, 3H), 4.12 (s, 2H), 6.71-6.76 (m, 2H), 7.31-8.19 (m, 7H), 8.49 (s, 1H)

(5) To a solution of the compound (200 mg) obtained in Example 134-(4) in N,N-dimethylformamide (5 ml), 3,4-dichlorobenzyl bromide (0.111 ml) and potassium carbonate (103 mg) were added, and the mixed solution was stirred at 80° C. for four hours. Ethyl acetate was added thereto, and the resulting solution washed with water and then washed with a saturated saline solution. The organic layer was dried over anhydrous magnesium sulfate, and evaporated under reduced pressure to remove the solvent. The resulting crude product was purified by column chromatography (neutral OH type silica gel, ethyl acetate/n-hexane=0 to 50%) to give methyl [1-({4-[(3,4-dichlorobenzyl)oxy]phenyl}carbonyl)isoquinolin-4-yl]acetate (70 mg) as a yellow amorphous substance.

¹H NMR (600 MHz, CHLOROFORM-d) d ppm 3.73 (s, 3H), 4.11 (s, 2H), 5.09 (s, 2H), 6.97-7.02 (m, 2H), 7.23-8.23 (m, 9H), 8.50 (s, 1H)

(6) The same procedure as used in Example 2-(3) was carried out using the compound (70 mg) obtained in Example 134-(5) to give the titled compound (33 mg) as a colorless amorphous substance.

Structural formulae and NMR values of Examples 127 to 134 are shown in Table 2.

[Ka 24]

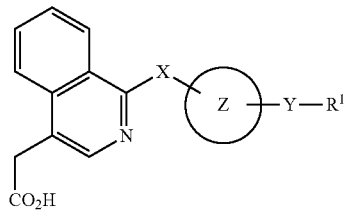

TABLE 2

| Example | X | Z | Y | R¹ | ¹H NMR (d ppm) |
|---|---|---|---|---|---|
| 127 | *–C(O)–* | *–(m-C₆H₄)–* | *–NH–C(O)–* | *–(3,4-Cl₂C₆H₃) | ¹H NMR (600 MHz, DMSO-d6) 4.18 (s, 2 H), 7.82 (s, 11 H), 8.55 (s, 1 H), 10.60 (s, 1 H), 12.75 (br. s., 1 H) |
| 128 | *–C(O)–* | *–(p-C₆H₄)–* | *–N(Me)–C(O)–* | *–(3,4-Cl₂C₆H₃) | ¹H NMR (600 MHz, DMSO-d6) 3.42 (s, 3 H), 4.17 (s, 2 H), 7.22-7.26 (m, 1 H), 7.37-7.41 (m, 2 H), 7.54-7.57 (m, 1 H), 7.62-7.64 (m, 1 H), 7.69-7.74 (m, 1 H), 7.76-7.80 (m, 2 H), 7.88-7.92 (m, 1 H), 8.04-8.07 (m, 1 H), 8.12-8.15 (m, 1 H), 8.52 (s, 1 H), 12.68 (br. s., 1 H) |
| 129 | *–C(O)–* | *–(p-C₆H₄)–* | *–NH–S(O)₂–* | *–(3,4-Cl₂C₆H₃) | ¹H NMR (600 MHz, DMSO-d6) 4.16 (s, 2 H), 7.23-7.27 (m, 2 H), 7.66-8.14 (m, 9 H), 8.49 (s, 1 H), 11.16 (br. s., 1 H), 12.67 (br. s., 1 H) |
| 130 | *–C(O)–* | *–(p-C₆H₄)–* | *–NH–C(O)–NH–* | *–(3,4-Cl₂C₆H₃) | ¹H NMR (600 MHz, DMSO-d6) 4.17 (s, 2 H), 7.33-8.17 (m, 11 H), 8.53 (s, 1 H), 9.19 (br. s., 1 H), 9.42 (br. s., 1 H), 12.67 (br. s., 1 H) |
| 131 | *–C(O)–* | *–(p-C₆H₄)–* | *–NH–C(O)–O–CH₂–* | *–(3,4-Cl₂C₆H₃) | ¹H NMR (600 MHz, DMSO-d6) 4.16 (s, 2 H), 5.19 (s, 2 H), 7.41-8.17 (m, 11 H), 8.52 (s, 1 H), 10.35 (s, 1 H), 12.73 (br. s., 1 H) |

TABLE 2-continued

| Example | X | Z | Y | R¹ | ¹H NMR (d ppm) |
|---|---|---|---|---|---|
| 132 | ketone C(=O) | 1,4-phenylene | urea -NH-C(=O)-NH- | 3,4-dichlorophenyl | ¹H NMR (600 MHz, DMSO-d6) 4.13 (s, 2 H), 4.27-4.34 (m, 2 H), 7.12 (br. s., 1 H), 7.25-8.16 (m, 11 H), 8.50 (s, 1 H), 9.42 (br. s., 1 H) |
| 133 | ketone C(=O) | 1,4-phenylene | -NH-CH2- | 3,4-dichlorophenyl | ¹H NMR (600 MHz, DMSO-d6) 4.11 (s, 2 H), 4.37-4.41 (m, 2 H), 6.61-6.66 (m, 2 H), 7.29-8.12 (m, 10 H), 8.44-8.47 (m, 1 H), 12.72 (br. s., 1 H) |
| 134 | ketone C(=O) | 1,4-phenylene | -O-CH2- | 3,4-dichlorophenyl | ¹H NMR (600 MHz, DMSO-d6) 4.12-4.15 (m, 2 H), 5.24 (s, 2 H), 7.14-8.16 (m, 11 H), 8.50 (s, 1 H) |

Example 135

{1-[(4-{[2-(4-chlorophenyl)ethyl]carbamoyl}phenyl)carbonyl]isoquinolin-4-yl}acetic acid (1) The same procedure as used in Example 1-(2) was carried out using tert-butyl 4-(cyanomethyl)benzoate (10.3 g) to give methyl 1-{[4-(tert-butoxycarbonyl)phenyl]carbonyl}isoquinoline-4-carboxylate (11.6 g) as a yellow oily substance.

¹H NMR (600 MHz, CHLOROFORM-d) d ppm 1.61 (s, 9H), 4.08 (s, 3H), 7.65-9.04 (m, 8H), 9.20 (s, 1H)

(2) The same procedure as used in Example 1-(3) was carried out using the compound (11.5 g) obtained in Example 135-(1) to give 1-{[4-(tert-butoxycarbonyl)phenyl]carbonyl}isoquinoline-4-carboxylic acid (9.47 g) as a colorless solid.

¹H NMR (600 MHz, DMSO-d₆) d ppm 1.56 (s, 9H), 7.45-9.01 (m, 8H), 9.11 (s, 1H), 13.83 (br. s., 1H)

(3) The same procedure as used in Example 1-(4) was carried out using the compound (9.47 g) obtained in Example 135-(2) to give tert-butyl 4-{[4-(2-methoxy-2-oxoethyl)isoquinolin-1-yl]carbonyl}benzoate (4.09 g) as an orange-colored amorphous substance.

¹H NMR (600 MHz, CHLOROFORM-d) d ppm 1.61 (s, 9H), 3.73 (s, 3H), 4.12 (s, 2H), 7.64-8.33 (m, 8H), 8.52 (s, 1H)

(4) To a solution of the compound (4.09 g) obtained in Example 135-(3) in chloroform (200 ml), trifluoroacetic acid (33 ml) was added, and the mixed solution was stirred at 50° C. for one hour. The solution was returned to room temperature, and water was added to the solution, followed by extraction with chloroform. The organic layer was dried over anhydrous magnesium sulfate, and evaporated under reduced pressure to remove the solvent to give 4-{[4-(2-methoxy-2-oxoethyl)isoquinolin-1-yl]carbonyl}benzoic acid (3.39 g) as a yellow solid.

¹H NMR (600 MHz, CHLOROFORM-d) d ppm 3.74 (s, 3H), 4.14 (s, 2H), 7.66-8.39 (m, 8H), 8.54 (s, 1H)

(5) To a solution of the compound (1.20 g) obtained in Example 135-(4) in chloroform (23 ml), oxalyl chloride (0.457 ml) and N,N-dimethylformamide (1 drop) were added, and the mixed solution was stirred at room temperature for one hour. The reacting solution was removed by evaporation under reduced pressure. To the resulting crude product (316 mg), chloroform (3 ml), 2-(4-chlorophenyl)ethyl amine (267 mg) and pyridine (0.139 ml) were added, and the mixed solution was stirred at room temperature for 14 hours. The reaction solution was washed with a saturated solution of ammonium chloride. The organic layer was dried over anhydrous magnesium sulfate, and evaporated under reduced pressure to remove the solvent. The resulting crude product was purified by column chromatography (NH type silica gel, ethyl acetate/n-hexane=0 to 50%, chloroform), and recrystallized (n-hexane/ethyl acetate) to give methyl {1-[(4-{[2-(4-chlorophenyl)ethyl]carbamoyl}phenyl)carbonyl]isoquinolin-4-yl}acetate (188 mg) as a colorless solid.

¹H NMR (600 MHz, CHLOROFORM-d) d ppm 2.90-2.95 (m, 2H), 3.68-3.76 (m, 5H), 4.12 (s, 2H), 6.13-6.20 (m, 1H), 7.13-8.35 (m, 12H), 8.51 (s, 1H)

(6) To a solution of the compound (188 mg) obtained in Example 135-(5) in tetrahydrofuran (3 ml), 1N aqueous sodium hydroxide solution (1.5 ml) was added in an ice bath, and the mixed solution was stirred at room temperature for one hour. Water and 1N aqueous hydrochloric acid solution were added in an ice bath, followed by extraction with ethyl acetate. The organic layer was washed with a saturated saline solution, was dried over anhydrous magnesium sulfate, and evaporated under reduced pressure to remove the solvent. The resulting crude product was recrystallized (ethanol-water) to give the titled compound (143 mg) as a colorless solid.

Compounds of Examples 136 to 140 were obtained by carrying out the same procedures as in Example 135. Structural formulae and NMR values of Examples 135 to 140 are shown in Table 3.

[Ka 25]

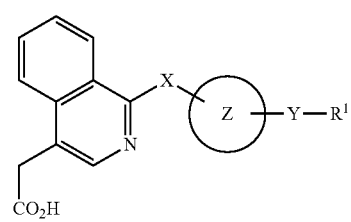

TABLE 3

| Example | X | Z | Y | R¹ | ¹H NMR (d ppm) |
|---|---|---|---|---|---|
| 135 | C(=O) | *-C₆H₄-* | *-C(=O)NH-CH₂CH₂-* | *-C₆H₄-Cl (4-Cl) | ¹H NMR (600 MHz, DMSO-d6) 2.83-2.88 (m, 2 H), 3.47-3.53 (m, 2 H), 4.18 (s, 2 H), 7.24-8.77 (m, 14 H), 12.74 (br. s., 1 H) |
| 136 | C(=O) | *-C₆H₄-* | *-C(=O)NH-* | *-C₆H₃-(Cl)₂ (3,4-diCl) | ¹H NMR (600 MHz, DMSO-d6) 4.17 (br. s., 2 H), 7.62-8.56 (m, 12 H), 10.72 (br. s, 1 H) |
| 137 | C(=O) | *-C₆H₄-* | *-C(=O)NH-CH₂CH₂-* | *-C₆H₃-(Cl)₂ (3,4-diCl) | ¹H NMR (600 MHz, DMSO-d6) 2.85-2.90 (m, 2 H), 3.50-3.55 (m, 2 H), 4.18 (br. s., 2 H), 7.21-8.77 (m, 13 H), 12.69 (br. s, 1 H) |
| 138 | C(=O) | *-C₆H₄-* | *-C(=O)NH-CH₂CH₂-* | *-C₆H₄-OMe (4-OMe) | ¹H NMR (600 MHz, DMSO-d6) 2.76-2.82 (m, 2 H), 3.43-3.49 (m, 2 H), 3.71 (s, 3 H), 4.18 (s, 2 H), 6.82-8.76 (m, 14 H) |
| 139 | C(=O) | *-C₆H₄-* | *-C(=O)NH-CH₂CH₂-* | *-C₆H₄-Cl (3-Cl) | ¹H NMR (600 MHz, DMSO-d6) 2.85-2.90 (m, 2 H), 3.49-3.55 (m, 2 H), 4.18 (s, 2 H), 7.18-8.78 (m, 14 H), 12.72 (br s, 1 H) |
| 140 | C(=O) | *-C₆H₄-* | *-C(=O)NH-* | *-C₆H₄-Cl (4-Cl) | ¹H NMR (600 MHz, DMSO-d6) 4.19 (s, 2 H), 7.41-8.24 (m, 12 H), 8.56 (s, 1 H), 10.58 (s, 1 H), 12.75 (br. s., 1 H) |

Example 141

[1-({4-[2-(4-chlorophenyl)ethoxy]phenyl}carbonyl)isoquinolin-4-yl]acetic acid (1) To a solution of the compound (100 mg) obtained in Example 134-(4) in tetrahydrofuran (2 ml), 2-(4-chlorophenyl)ethanol, tri-n-butyl phosphine (0.116 ml) and tetramethyl azodicarboxyamide (80 mg) were added. The mixed solution was stirred at room temperature for 18 hours. To the reaction solution, water was added, followed by extraction with ethyl acetate. The organic layer was dried over anhydrous magnesium sulfate, and evaporated under reduced pressure to remove the solvent. The resulting crude product was purified by column chromatography (neutral OH type silica gel, ethyl acetate/n-hexane=10 to 50%) to give methyl [1-({4-[2-(4-chlorophenyl)ethoxy]phenyl}carbonyl)isoquinolin-4-yl]acetate (41 mg) as a colorless oily substance.

¹H NMR (600 MHz, CHLOROFORM-d) d ppm 3.09 (t, J=6.8 Hz, 2H), 3.73 (s, 3H), 4.10 (s, 2H), 4.22 (t, J=6.8 Hz, 2H), 6.89-8.52 (m, 13H)

(2) The same procedure as used in Example 135-(6) was carried out using the compound (38 mg) obtained in Example 141-(1) to give the titled compound (35 mg) as a colorless amorphous substance.

By carrying out the same procedure as in Example 141, compounds of Examples 142 and Example 143 were obtained.

Example 144

{1-[(4-benzyl phenyl)carbonyl]isoquinolin-4-yl}acetic acid (1) The same procedure as used in Example 1-(2) was carried out using 4-benzyl phenyl acetonitrile (2.06 g) to give methyl 1-[(4-benzyl phenyl)carbonyl]isoquinoline-4-carboxylate (1.82 g).

¹H NMR (600 MHz, CHLOROFORM-d) d ppm 4.05 (s, 2H), 4.07 (s, 3H), 7.13-9.05 (m, 13H), 9.19 (s, 1H)

(2) The same procedure as used in Example 1-(3) was carried out using the compound (1.81 g) obtained in Example 144-(1) to give 1-[(4-benzyl phenyl)carbonyl]isoquinoline-4-carboxylic acid (1.10 g).

¹H NMR (600 MHz, CHLOROFORM-d) d ppm 4.03 (s, 2H), 7.07-9.14 (m, 13H), 9.34 (s, 1H)

(3) The same procedure as used in Example 1-(4) was carried out using the compound (1.10 g) obtained in Example 144-(2) to give methyl {1-[(4-benzyl phenyl)carbonyl]isoquinolin-4-yl}acetate (550 mg).

¹H NMR (600 MHz, CHLOROFORM-d) d ppm 3.72 (s, 3H), 4.05 (s, 2H), 4.10 (s, 2H), 7.15-8.26 (m, 13H), 8.50 (s, 1H)

(4) The same procedure as used in Example 135-(6) was carried out using the compound (538 mg) obtained in Example 144-(3) to give the titled compound (35 mg) as a pale yellow amorphous substance.

By carrying out the same procedure as in Example 144, a compound of Example 145 was obtained.

Example 146

{1-[(4-{[2-(4-chlorophenyl)ethoxy]methyl}phenyl)carbonyl]isoquinolin-4-yl}acetic acid (1) To a solution of 4-chlorobenzyl alcohol (4.10 g) in N,N-dimethylformamide (110 ml), sodium hydride (60 to 72%, 952 mg) was added in an ice bath, and the mixed solution was stirred for 30 min. Then, to the resulting solution, 4-(bromomethyl)benzoic acid methyl ester (5.00 g) was added, and the mixed solution was stirred at room temperature for three hours. To the resulting solution, ethyl acetate was added. The resulting solution was washed with water and with a saturated saline solution, sequentially, dried over anhydrous sodium sulfate, and evaporated under reduced pressure to remove the solvent. The resulting crude product was purified by column chromatography (neutral OH type silica gel, ethyl acetate/n-hexane=5 to 9%) to give methyl 4-{[2-(4-chlorophenyl)ethoxy]methyl}benzoate (5.25 g).

$^1$H NMR (600 MHz, CHLOROFORM-d) d ppm 2.90 (t, J=6.6 Hz, 2H), 3.68 (t, J=6.6 Hz, 2H), 3.91 (s, 3H), 4.56 (s, 2H), 7.11-7.37 (m, 6H), 7.92-8.05 (m, 2H)

(2) To a solution of the compound (2.50 g) obtained in Example 146-(1) in tetrahydrofuran (40 ml), lithium aluminum hydride (467 mg) was added in an ice bath, and the mixed solution was stirred for 15 min, and then stirred at room temperature for two hours. Water was added to the solution in an ice bath, and then 2.5; N aqueous sodium hydroxide solution was added. The solution was stirred for 30 min, and then stirred at room temperature for 1.5 hours. The reaction solution was filtered through celite, and the filtrate was removed by evaporation under reduced pressure. The resulting crude product was purified by column chromatography (neutral OH type silica gel, ethyl acetate/n-hexane=9 to 15%) to give (4-{[2-(4-chlorophenyl)ethoxy]methyl}phenyl)methanol (2.24 g).

$^1$H NMR (600 MHz, CHLOROFORM-d) d ppm 1.62 (t, J=6.0 Hz, 1H), 2.88 (t, J=6.9 Hz, 2H), 3.66 (t, J=6.9 Hz, 2H), 4.50 (s, 2H), 4.69 (d, J=6.0 Hz, 2H), 7.02-7.44 (m, 8H)

(3) To a solution of the compound (2.24 g) obtained in Example 146-(2) in chloroform (40 ml), triethylamine (1.12 ml) was added, and thionyl chloride (0.646 ml) was added in an ice bath. Then, the mixed solution was stirred at room temperature for one hour. Water was added thereto, followed by extraction with chloroform. The organic layer was washed with a saturated saline solution, dried over anhydrous sodium sulfate, and evaporated under reduced pressure to remove the solvent. To a solution of the resulting crude product in DMSO (27 ml), sodium cyanide (436 mg) was added, and the mixed solution was stirred at room temperature for one hour, and then stirred at 60° C. for 30 min. Water was added to the solution, and the solution as extracted with ethyl acetate. The organic layer was dried over anhydrous sodium sulfate, was evaporated under reduced pressure to remove the solvent. The resulting crude product was purified by column chromatography (neutral OH type silica gel, ethyl acetate/n-hexane=15 to 25%) to give (4-{[2-(4-chlorophenyl)ethoxy]methyl}phenyl)acetonitrile (1.62 g).

$^1$H NMR (600 MHz, CHLOROFORM-d) d ppm 2.89 (t, J=6.9 Hz, 2H), 3.66 (t, J=6.9 Hz, 2H), 3.74 (s, 2H), 4.50 (s, 2H), 7.04-7.34 (m, 8H)

(4) The same procedure as used in Example 1-(2) was carried out using the compound (1.42 g) obtained in Example 146-(3) to give methyl 1-[(4-{[2-(4-chlorophenyl)ethoxy]methyl}phenyl)carbonyl]isoquinoline-4-carboxylate (950 mg).

$^1$H NMR (600 MHz, CHLOROFORM-d) d ppm 2.84-2.94 (m, 2H), 3.64-3.71 (m, 2H), 4.08 (s, 3H), 4.56 (s, 2H), 7.11-8.17 (m, 11H), 9.02 (d, J=8.7 Hz, 1H), 9.20 (s, 1H)

(5) The same procedure as used in Example 135-(6) was carried out using the compound (951 mg) obtained in Example 146-(4) to give 1-[(4-{[2-(4-chlorophenyl)ethoxy]methyl}phenyl)carbonyl]isoquinoline-4-carboxylic acid (950 mg).

$^1$H NMR (600 MHz, CHLOROFORM-d) d ppm 2.82-2.95 (m, 2H), 3.59-3.77 (m, 2H), 4.59 (s, 2H), 7.00-9.19 (m, 12H), 9.38 (s, 1H)

(6) The same procedure as used in Example 1-(4) was carried out using the compound (674 mg) obtained in Example 146-(5) to give methyl {1-[(4-{[2-(4-chlorophenyl)ethoxy]methyl}phenyl)carbonyl]isoquinolin-4-yl}acetate (260 mg).

$^1$H NMR (600 MHz, CHLOROFORM-d) d ppm 2.89 (t, J=6.6 Hz, 2H), 3.68 (t, J=6.6 Hz, 2H), 3.73 (s, 3H), 4.11 (s, 2H), 4.58 (s, 2H), 7.12-8.27 (m, 12H), 8.52 (s, 1H)

(7) The same procedure as used in Example 135-(6) was carried out using the compound (253 mg) obtained in Example 146-(6) to give the titled compound (140 mg) as a pale yellow amorphous substance.

Example 147

{1-[(4-{[(4-chlorobenzyl)amino]methyl}phenyl)carbonyl]isoquinolin-4-yl}acetic acid hydrochloride (1) To a solution of 4-formyl benzoic acid methyl (10.0 g) in chloroform (300 ml), 4-chlorobenzylamine (11.2 g) was added, and the mixed solution was stirred for 15 min. Then, to the resulting solution, sodium triacetoxyborohydride (16.8 g) was added, and the mixed solution was stirred at room temperature for two hours. To the resulting solution, acetic acid (10.5 ml) was added, and the solution was stirred for four hours. Saturated sodium bicarbonate water was added, followed by extraction with chloroform. The organic layer was dried over anhydrous sodium sulfate, evaporated under reduced pressure to remove the solvent, and the resulting crude product was purified by column chromatography (neutral OH type silica gel, ethyl acetate/n-hexane=15 to 50%) to give methyl 4-{[(4-chlorobenzyl)amino]methyl}benzoate (13.8 g).

$^1$H NMR (600 MHz, CHLOROFORM-d) d ppm 3.77 (s, 2H), 3.84 (s, 2H), 3.91 (s, 3H), 7.24-7.33 (m, 4H), 7.41 (d, J=8.7 Hz, 2H), 7.97-8.04 (m, 2H)

(2) To a solution of the compound (13.8 g) obtained in Example 147-(1) in chloroform (239 ml), di-tert-butyl dicarbonate (12.5 g) was added, and 4-dimethyl amino pyridine (5.80 g) was added in an ice bath. The mixed solution was stirred at room temperature for three hours, and the reaction solution was removed by evaporation under reduced pressure. The resulting crude product was purified by column chromatography (neutral OH type silica gel, ethyl acetate/n-hexane=3 to 7%) to give methyl 4-{[(tert-butoxycarbonyl)(4-chlorobenzyl)amino]methyl}benzoate (12.9 g).

$^1$H NMR (600 MHz, CHLOROFORM-d) d ppm 1.47 (s, 9H), 3.92 (s, 3H), 4.23-4.55 (m, 4H), 7.05-7.33 (m, 6H), 7.96-8.03 (m, 2H)

(3) The same procedure as used in Example 146-(2) was carried out using the compound (2.00 g) obtained in Example 147-(2) to give tert-butyl (4-chlorobenzyl)[4-(hydroxymethyl)benzyl]carbamate (1.79 g).

$^1$H NMR (600 MHz, CHLOROFORM-d) d ppm 1.49 (s, 9H), 1.63-1.67 (m, 1H), 4.25-4.45 (m, 4H), 4.66-4.73 (m, 2H), 7.07-7.35 (m, 8H)

(4) The same procedure as used in Example 146-(3) was carried out using the compound (1.70 g) obtained in Example 147-(3) to give tert-butyl (4-chlorobenzyl)[4-(cyanomethyl)benzyl]carbamate (1.30 g).

¹H NMR (600 MHz, CHLOROFORM-d) d ppm 1.49 (s, 9H), 3.74 (s, 2H), 4.22-4.48 (m, 4H), 7.06-7.32 (m, 8H)

(5) The same procedure as used in Example 1-(2) was carried out using the compound (1.30 g) obtained in Example 147-(4) to give methyl 1-[(4-{[(tert-butoxycarbonyl)(4-chlorobenzyl)amino]methyl}phenyl)carbonyl]isoquinoline-4-carboxylate (750 mg).

¹H NMR (600 MHz, CHLOROFORM-d) d ppm 1.48 (s, 9H), 4.08 (s, 3H), 4.26-4.53 (m, 4H), 7.04-8.22 (m, 11H), 8.98-9.05 (m, 1H), 9.20 (s, 1H)

(6) The same procedure as used in Example 135-(6) was carried out using the compound (749 mg) obtained in Example 147-(5) to give 1-[(4-{[(tert-butoxycarbonyl)(4-chlorobenzyl)amino]methyl}phenyl)carbonyl]isoquinoline-4-carboxylic acid (684 mg).

¹H NMR (600 MHz, CHLOROFORM-d) d ppm 1.47 (br. s., 9H), 4.21-4.58 (m, 4H), 7.05-8.22 (m, 11H), 9.09-9.17 (m, 1H), 9.37 (s, 1H)

(7) The same procedure as used in Example 1-(4) was carried out using the compound (681 mg) obtained in Example 147-(6) to give methyl {1-[(4-{[(tert-butoxycarbonyl) (4-chlorobenzyl)amino]methyl}phenyl)carbonyl]isoquinolin-4-yl}acetate (230 mg).

¹H NMR (600 MHz, CHLOROFORM-d) d ppm 1.48 (s, 9H), 4.12 (s, 2H), 4.25-4.51 (m, 4H), 7.06-8.30 (m, 12H), 8.52 (s, 1H)

(8) The same procedure as used in Example 135-(6) was carried out using the compound (223 mg) obtained in Example 147-(7) to give {1-[(4-{[(tert-butoxycarbonyl)(4-chlorobenzyl)amino]methyl}phenyl)carbonyl]isoquinolin-4-yl}acetic acid (170 mg).

¹H NMR (600 MHz, CHLOROFORM-d) d ppm 1.47 (s, 9H), 4.12 (s, 2H), 4.23-4.54 (m, 4H), 6.99-8.32 (m, 12H), 8.52 (s, 1H)

(9) To a solution of the compound (168 mg) obtained in Example 147-(8) in ethyl acetate (1 ml), 4 N hydrochloric acid-ethyl acetate (1 ml) was added, and the mixed solution was stirred at room temperature for 15 hours. The produced solid was filtered out to give the titled compound (120 mg) as a colorless solid.

Structural formulae and NMR values of Examples 141 to 147 are shown in Table 4.

[Ka 26]

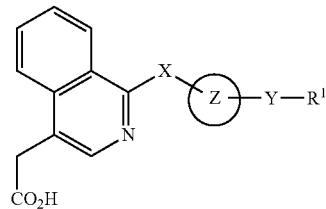

TABLE 4

| Example | X | Z | Y | R¹ | ¹H NMR (d ppm) |
|---|---|---|---|---|---|
| 141 | C(=O) | 1,4-phenylene | *—O—CH₂CH₂—* | 4-Cl-phenyl | ¹H NMR (600 MHz, DMSO-d6) 3.06 (t, J = 6.6 Hz, 2 H), 4.16 (s, 2 H), 4.30 (t, J = 6.6 Hz, 2 H), 7.04-8.14 (m, 12 H), 8.51 (s, 1 H), 12.69 (br. s., 1 H) |
| 142 | C(=O) | 1,4-phenylene | *—O—CH₂CH₂CH₂—* | 4-Cl-phenyl | ¹H NMR (600 MHz, DMSO-d6) 2.00-2.07 (m, 2 H), 2.72-2.76 (m, 2 H), 4.07 (t, J = 6.4 Hz, 2 H), 4.15 (s, 2 H), 7.03-8.15 (m, 12 H), 8.51 (s, 1 H) |
| 143 | C(=O) | 1,4-phenylene | *—O—CH₂CH₂—O—* | 4-Cl-phenyl | ¹H NMR (600 MHz, DMSO-d6) 4.16 (s, 2 H), 4.32-4.37 (m, 2 H), 4.40-4.46 (m, 2 H), 6.99-8.16 (m, 12 H), 8.52 (s, 1 H), 12.69 (br. s., 1 H) |
| 144 | C(=O) | 1,4-phenylene | *—CH₂CH₂—* | phenyl | ¹H NMR (600 MHz, DMSO-d6) 4.03-4.06 (m, 2 H), 4.14 (s, 2 H), 7.18-8.16 (m, 13 H), 8.50 (s, 1 H) |
| 145 | C(=O) | 1,4-phenylene | *—O—* | phenyl | ¹H NMR (600 MHz, DMSO-d6) 4.17 (s, 2 H), 7.05-8.15 (m, 13 H), 8.52 (s, 1 H), 12.68 (br. s., 1 H) |
| 146 | C(=O) | 1,4-phenylene | *—CH₂—O—CH₂CH₂—* | 4-Cl-phenyl | ¹H NMR (600 MHz, DMSO-d6) 2.84-2.90 (m, 2 H), 3.65-3.70 (m, 2 H), 4.14 (s, 2 H), 4.59 (s, 2 H), 7.26-8.18 (m, 12 H), 8.51 (s, 1 H) |
| 147 | C(=O) | 1,4-phenylene | *—CH₂—NH—CH₂—* | 4-Cl-phenyl | ¹H NMR (600 MHz, DMSO-d6) 4.15-4.28 (m, 6 H), 7.47-8.18 (m, 12 H), 8.54 (s, 1 H), 9.90-9.97 (m, 2 H) |

Example 148

[1-(4-{[(3,4-dichlorophenyl)carbonyl]amino}benzyl)isoquinolin-4-yl]acetic acid (1) To a solution of the compound (500 mg) obtained in Example 2-(1) in tetrahydrofuran (10 ml)-methanol (3 ml), sodium borohydride (173 mg) was added in an ice bath, and the mixed solution was stirred for 15 min. Furthermore, sodium borohydride (177 mg) was added to the solution, and the mixed solution was stirred for 30 min in an ice bath. In addition, sodium borohydride (354 mg) was added three times every 30 min in an ice bath. A saturated aqueous solution of ammonium chloride was added, followed by extraction with chloroform. The organic layer was dried over anhydrous magnesium sulfate, and evaporated under reduced pressure to remove the solvent. To a solution of the resulting crude product in chloroform (7 ml), triethylsilane (1.5 ml) and trifluoroacetic acid (1.5 ml) were added, and the mixed solution was stirred at 60° C. for 14 hours. A saturated aqueous solution of sodium hydrogencarbonate was added to the solution, followed by extraction with chloroform. The organic layer was dried over anhydrous magnesium sulfate, and evaporated under reduced pressure to remove the solvent. The resulting crude product was purified by column chromatography (NH type silica gel, ethyl acetate/n-hexane=40 to 60%) to give methyl [1-(4-amino benzyl)isoquinolin-4-yl]acetate (165 mg) as a colorless solid.

$^1$H NMR (600 MHz, CHLOROFORM-d) d ppm 3.53 (br. s., 2H), 3.69 (s, 3H), 3.99 (s, 2H), 4.54 (s, 2H), 6.56-6.61 (m, 2H), 7.05-7.09 (m, 2H), 7.51-7.56 (m, 1H), 7.66-7.70 (m, 1H), 7.92-7.95 (m, 1H), 8.18-8.22 (m, 1H), 8.39 (s, 1H)

(2) To a solution of the compound (190 mg) obtained in Example 148-(1) in pyridine (3 ml), 3,4-dichlorobenzoyl chloride (195 mg) was added in an ice bath, and the mixed solution was stirred at room temperature for 14 hours. A saturated aqueous sodium hydrogencarbonate solution was added, followed by extraction with ethyl acetate. The organic layer was washed with diluted hydrochloric acid, to which a saturated aqueous solution of sodium hydrogencarbonate was added, followed by extraction with ethyl acetate. The organic layer was dried over anhydrous magnesium sulfate, and then evaporated under reduced pressure to remove the solvent. The resulting crude product was purified by column chromatography (acidic OH type silica gel, ethyl acetate/n-hexane=30 to 60%) to give methyl [1-(4-{[(3,4-dichlorophenyl)carbonyl]amino}benzyl)isoquinolin-4-yl]acetate (210 mg) as a pale brown solid.

$^1$H NMR (600 MHz, CHLOROFORM-d) d ppm 3.69 (s, 3H), 4.00 (s, 2H), 4.64 (s, 2H), 7.26-7.28 (m, 2H), 7.45-7.72 (m, 7H), 7.90-7.97 (m, 2H), 8.13-8.17 (m, 1H), 8.40 (s, 1H)

(3) To a solution of the compound (200 mg) obtained in Example 148-(2) in tetrahydrofuran (4 ml)-methanol (4 ml), 1N aqueous sodium hydroxide solution (6 ml) was added in an ice bath, and the mixed solution was stirred in an ice bath for 20 min. Water and acetic acid were added thereto, and a precipitate was filtered, washed with water, and then dried. The resulting crude product was recrystallized (ethanol-water) to give the titled compound (165 mg) as a colorless solid.

Example 149

(1-{4-[2-(4-chlorophenyl)ethoxy]benzyl}isoquinolin-4-yl)acetic acid (1) The same procedure as used in Example 148-(1) was carried out using the compound (1.00 g) obtained in Example 134-(3) to give methyl [1-(4-methoxybenzyl)isoquinolin-4-yl]acetate (621 mg) as a pale yellow solid.

$^1$H NMR (600 MHz, CHLOROFORM-d) d ppm 3.69 (s, 3H), 3.74 (s, 3H), 4.00 (s, 2H), 4.60 (s, 2H), 6.76-8.42 (m, 9H)

(2) To a solution of the compound (678 mg) obtained in Example 149-(1) in chloroform (20 ml), a solution of boron tribromide (1.09 ml) in chloroform (10 ml) was added dropwise at −50° C., and the mixed solution was stirred in an ice bath for one hour. Methanol was added dropwise thereto in an ice bath, and saturated sodium bicarbonate water was added, followed by extraction with chloroform. The solution as washed with a saturated saline solution, dried over anhydrous magnesium sulfate, and evaporated under reduced pressure to remove the solvent. The resulting crude product was purified by column chromatography (neutral OH type silica gel, ethyl acetate/n-hexane=20 to 60%) to give methyl [1-(4-hydroxybenzyl)isoquinolin-4-yl]acetate (418 mg) as a colorless solid.

$^1$H NMR (600 MHz, CHLOROFORM-d) d ppm 3.69 (s, 3H), 4.00 (s, 2H), 4.58 (s, 2H), 6.66-8.40 (m, 9H)

(3) The same procedure as used in Example 141-(1) was carried out using the compound (120 mg) obtained in Example 149-(2) to give methyl (1-{4-[2-(4-chlorophenyl)ethoxy]benzyl}isoquinolin-4-yl)acetate (95 mg) as a colorless solid.

$^1$H NMR (600 MHz, CHLOROFORM-d) d ppm 3.00 (t, J=6.9 Hz, 2H), 3.69 (s, 3H), 3.99 (s, 2H), 4.08 (t, J=6.9 Hz, 2H), 4.58 (s, 2H), 6.73-8.41 (m, 13H)

(4) To a solution of the compound (83 mg) obtained in Example 149-(3) in tetrahydrofuran (2 ml), 1N sodium hydroxide aqueous solution (1 ml) was added, and the mixed solution was stirred at room temperature for 23 hours. A saturated aqueous ammonium chloride solution was added thereto, and acetic acid was added thereto, followed by extraction with ethyl acetate. The organic layer was washed with a saturated saline solution, dried over anhydrous magnesium sulfate, and evaporated under reduced pressure to remove the solvent. To the resulting crude product, diethyl ether was added, and the mixture was stirred at room temperature for 14 hours. The produced solid was filtered out to give the titled compound (58 mg) as a colorless solid.

By the same procedure as in Example 149, compounds of Examples 150 and 151 were obtained.

Example 152

[1-(4-{[2-(4-chlorophenyl)ethyl]sulfamoyl}benzyl)isoquinolin-4-yl]acetic acid (1) To a solution of 2-(4-chlorophenyl)ethylamine (2.83 g) and triethylamine (1.46 ml) in tetrahydrofuran (50 ml), 4-(bromomethyl)benzenesulphonyl chloride (1.63 g) was added, and the mixed solution was stirred at room temperature for one hour. Ethyl acetate was added thereto, and the solution was washed with a saturated solution of ammonium chloride and then washed with water. The organic layer was dried over anhydrous magnesium sulfate, and evaporated under reduced pressure to remove the solvent. The resulting crude product was purified by column chromatography (neutral OH type silica gel, ethyl acetate/n-hexane=10 to 30%) to give 4-(bromomethyl)-N-[2-(4-chlorophenyl)ethyl]benzene sulfonamide (2.04 g) as a colorless solid.

$^1$H NMR (600 MHz, CHLOROFORM-d) d ppm 2.67-2.82 (m, 2H), 3.12-3.33 (m, 2H), 4.38 (t, 1=6.2 Hz, 1H), 4.50 (s, 2H), 6.93-7.80 (m, 8H)

(2) To a solution of the compound (927 mg) obtained in Example 152-(1) in toluene (12 ml), tri-n-butyl phosphine (0.883 ml) was added, and the mixed solution was stirred at 60° C. for 30 min. The reaction solution was removed by evaporation under reduced pressure, and to a solution of the resulting crude product in chloroform (10 ml), n-hexane (200 ml) was added dropwise. The solution was stirred at room temperature for one hour. After decantation, tributyl(4-{[2-(4-chlorophenyl)ethyl]sulfamoyl}benzyl)phosphonium bromide (1.37 g) was obtained as a colorless amorphous substance.

$^1$H NMR (600 MHz, CHLOROFORM-d) d ppm 0.88-0.96 (m, 9H), 1.40-1.52 (m, 12H), 2.31-2.40 (m, 6H), 2.85 (t, J=7.3 Hz, 2H), 3.14-3.20 (m, 2H), 4.46-4.58 (m, 2H), 5.90-5.97 (m, 1H), 7.07-7.24 (m, 4H), 7.57-7.85 (m, 4H)

(3) To a solution of the compound (1.02 g) obtained in Example 152-(2) and 1-chloro-isoquinoline-4-carboxylic acid methyl ester (381 mg) in tetrahydrofuran (9 ml), sodium bis(trimethylsilyl)amide (2.72 ml, 1.9 M solution) was added dropwise at −30° C., and the solution was stirred at room temperature for two hours. Furthermore, the solution was stirred at 50° C. for one hour, and then 1M aqueous sodium carbonate solution (3.44 ml) was added thereto, and the solution was stirred at 50° C. for two hours. Ethyl acetate was added thereto, and the solution was washed with a saturated aqueous ammonium chloride solution, and then washed with a saturated saline solution. The organic layer was dried over anhydrous magnesium sulfate, and then evaporated under reduced pressure to remove the solvent. The resulting crude product was purified by column chromatography (neutral OH type silica gel, ethyl acetate/n-hexane=10 to 50%) to give methyl 1-(4-{[2-(4-chlorophenyl)ethyl]sulfamoyl}benzyl)isoquinoline-4-carboxylate (124 mg) as a pale yellow solid.

$^1$H NMR (600 MHz, DMSO-d$_6$) d ppm 2.57-2.63 (m, 2H), 2.88-2.95 (m, 2H), 3.96 (s, 3H), 4.83 (s, 2H), 7.07-8.83 (m, 13H), 9.00 (s, 1H)

(4) To a solution of the compound (169 mg) obtained in Example 152-(3) in tetrahydrofuran (4 ml), 1N aqueous sodium hydroxide solution (2 ml) was added. The mixed solution was stirred at room temperature for three hours. Water and 1N aqueous hydrochloric acid solution were added in an ice bath, followed by extraction with ethyl acetate. The organic layer was washed with a saturated saline solution, dried over anhydrous magnesium sulfate, and evaporated under reduced pressure to remove the solvent to give 1-(4-{[2-(4-chlorophenyl)ethyl]sulfamoyl}benzyl)isoquinoline-4-carboxylic acid (164 mg) as a pale yellow solid.

$^1$H NMR (600 MHz, DMSO-d$_6$) d ppm 2.58-2.65 (m, 2H), 2.87-2.96 (m, 2H), 4.82 (s, 2H), 7.05-9.03 (m, 14H), 13.45 (br. s., 1H)

(5) To a solution of the compound (164 mg) obtained in Example 152-(4) in chloroform (4 ml), oxalyl chloride (0.058 ml) and N,N-dimethylformamide (0.004 ml) were added in an ice bath, and the mixed solution was stirred at room temperature for one hour, and evaporated under reduced pressure to remove the solvent. To the resulting crude product, tetrahydrofuran (2 ml) and acetonitrile (2 ml) were added, and (trimethylsilyl)diazomethane (0.341 ml, 2 M solution) was added dropwise in an ice bath. The mixed solution was stirred in an ice bath for one hour. The solution was evaporated under reduced pressure to remove the solvent. To the resulting crude product, water (2 ml), 1,4-dioxane (2 ml) and silver acetate (17 mg) were added, and the solution was stirred at 60° C. for 30 min. The reaction solution was filtered through celite, and water was added to the filtrate, followed by extraction with ethyl acetate. The organic layer was washed with a saturated saline solution, dried over anhydrous magnesium sulfate, and evaporated under reduced pressure to remove the solvent. The resulting crude product was purified by column chromatography (acidic OH type silica gel, methanol/chloroform=0 to 15%), and diethyl ether was added thereto, and the purified product was stirred at room temperature for 15 hours. The resultant solid was filtered out and dried to give the titled compound (50 mg) as a pale yellow solid.

Structural formulae and NMR values of Examples 148 to 152 are shown in Table 5.

[Ka 27]

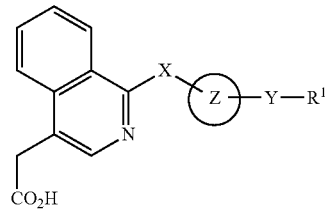

TABLE 5

| Example | X | Z | Y | R$^1$ | $^1$H NMR (d ppm) |
|---|---|---|---|---|---|
| 148 | *∼∼* | *–C$_6$H$_4$–* | *–NH–C(=O)–* | 2,4-diCl-C$_6$H$_3$ | $^1$H NMR (600 MHz, DMSO-d6) 4.00 (s, 2 H), 4.60 (s, 2 H), 7.24-7.32 (m, 2 H), 7.58-7.67 (m, 3 H), 7.73-7.83 (m, 2 H), 7.87-7.92 (m, 1 H), 7.94-8.00 (m, 1 H), 8.14-8.19 (m, 1 H), 8.29-8.37 (m, 2 H), 10.31 (br. s., 1 H), 12.59 (br, s., 1 H) |
| 149 | *∼∼* | *–C$_6$H$_4$–* | *–O–CH$_2$CH$_2$–* | 4-Cl-C$_6$H$_4$ | $^1$H NMR (600 MHz, DMSO-d6) 2.97 (t, J = 6.6 Hz, 2 H), 3.99 (s, 2 H), 4.09 (t, J = 6.6 Hz, 2 H), 4.53 (s, 2 H), 6.77-8.35 (m, 13 H), 12.55 (br. s., 1 H) |
| 150 | *∼∼* | *–C$_6$H$_4$–* | *–O–CH$_2$CH$_2$CH$_2$–* | 4-Cl-C$_6$H$_4$ | $^1$H NMR (600 MHz, DMSO-d6) 1.91-1.98 (m, 2 H), 2.66-2.71 (m, 2 H), 3.86 (t, J = 6.4 Hz, 2 H), 3.98 (s, 2 H), 4.53 (s, 2 H), 6.77-8.36 (m, 13 H) |

TABLE 5-continued

| Example | X | Z | Y | R¹ | ¹H NMR (d ppm) |
|---|---|---|---|---|---|
| 151 | ethyl | 1,4-phenylene | *-O-CH₂CH₂-O-* | 4-chlorophenyl | ¹H NMR (600 MHz, DMSO-d6) 4.00 (s, 2 H), 4.20-4.27 (m, 4 H), 4.55 (s, 2 H), 6.80-8.38 (m, 13 H), 12.50 (br. s., 1 H) |
| 152 | ethyl | 1,4-phenylene | *-S(O)₂-NH-CH₂CH₂-* | 4-chlorophenyl | ¹H NMR (600 MHz, DMSO-d6) 2.60-2.65 (m, 2 H), 2.89-2.95 (m, 2 H), 4.01 (s, 2 H), 4.72 (s, 2 H), 7.09-8.37 (m, 14 H), 12.57 (br. s., 1 H) |

Example 153

[1-(4-{[2-(4-chlorophenyl)ethyl]carbamoyl}benzyl)isoquinolin-4-yl]acetic acid (1) To a solution of 4-(bromomethyl)benzoic acid tert-butyl ester (22.1 g) in toluene (440 ml), tri-n-butylphosphine (30.5 ml) was added, and the mixed solution was stirred at 60° C. for 70 min. The reaction solution was removed by evaporation under reduced pressure, and to the resulting crude product, n-hexane was added and stirred. The resulting solid was filtered out to give [4-(tert-butoxycarbonyl)benzyl](tributyl)phosphonium bromide (36.0 g) as a colorless solid.

¹H NMR (600 MHz, CHLOROFORM-d) d ppm 0.93-0.98 (m, 9H), 1.44-1.52 (m, 12H), 1.60 (s, 9H), 2.37-2.46 (m, 6H), 4.34-4.40 (m, 2H), 7.50-8.02 (m, 4H)

(2) To a solution of the compound (33.8 g) obtained in Example 153-(1) and 1-chloro-isoquinoline-4-carboxylic acid methyl ester (11.3 g) in tetrahydrofuran (235 ml), sodium bis(trimethylsilyl)amide (64 ml, 1.9M solution) was added dropwise at −30° C., and the resulting solution was stirred at room temperature for 45 min. Furthermore, the resulting solution was stirred at 50° C. for 75 min, and then a solution of sodium carbonate (10.2 g) in water (120 ml) was added, the resulting solution was stirred 60° C. for two hours. 1N aqueous hydrochloric acid solution was added so as to adjust the solution to pH5, followed by extraction with ethyl acetate. The organic layer was dried over anhydrous magnesium sulfate, and evaporated under reduced pressure to remove the solvent. The resulting crude product was purified by column chromatography (neutral OH type silica gel, ethyl acetate/n-hexane=10 to 30%) to give methyl 1-[4-(tert-butoxycarbonyl)benzyl]isoquinoline-4-carboxylate (12.0 g) as an orange-colored oily substance.

¹H NMR (600 MHz, CHLOROFORM-d) d ppm 1.55 (s, 9H), 4.02 (s, 3H), 4.76 (s, 2H), 7.27-8.98 (m, 8H), 9.14 (s, 1H)

(3) To a solution of the compound (11.8 g) obtained in Example 153-(2) in tetrahydrofuran (150 ml), 1N aqueous sodium hydroxide solution (150 ml) was added, and the mixed solution was stirred at 50° C. for 2.5 hours. The resulting solution was returned to room temperature, 1N aqueous hydrochloric acid solution was added to adjust the solution to pH5, followed by extraction with ethyl acetate. The organic layer was washed with a saturated saline solution, dried over anhydrous magnesium sulfate, and then evaporated under reduced pressure to remove the solvent to give 1-[4-(tert-butoxycarbonyl)benzyl]isoquinoline-4-carboxylic acid (11.1 g) as a pale orange-colored solid.

¹H NMR (600 MHz, DMSO-d₆) d ppm 1.50 (s, 9H), 4.76 (s, 2H), 7.38-8.99 (m, 9H)

(4) To a solution of the compound (11.1 g) obtained in Example 153-(3) in chloroform (265 ml), oxalyl chloride (5.1 ml) and N,N-dimethylformamide (0.1 ml) were added in an ice bath, and the mixed solution was stirred in an ice bath for 70 min, and evaporated under reduced pressure to remove the solvent. To the resulting crude product, tetrahydrofuran (133 ml) and acetonitrile (133 ml) were added, and (trimethylsilyl)diazomethane (29.5 ml, 2 M solution) was added dropwise in an ice bath. The mixed solution was stirred in an ice bath for three hours. The solvent was removed by evaporation under reduced pressure, and to the resulting crude product, water (133 ml) and 1,4-dioxane (133 ml) and silver acetate (2.95 g) were added, and the mixed solution was stirred at 60° C. for 45 min. The solution was returned to room temperature, and water was added to the solution, followed by extraction with ethyl acetate. The organic layer was washed with a saturated saline solution, dried over anhydrous magnesium sulfate, and evaporated under reduced pressure to remove the solvent. To the resulting crude product, methanol (265 ml) was added, and (trimethylsilyl)diazomethane (44.2 ml, 2 M solution) was added dropwise at room temperature, and the solution was stirred for 20 min. The solvent was removed by evaporation under reduced pressure, and resulting crude product was purified by column chromatography (neutral OH type silica gel, ethyl acetate/n-hexane=10 to 40%) to give tert-butyl 4-{[4-(2-methoxy-2-oxoethyl)isoquinolin-1-yl]methyl}benzoate (4.07 g) as a brown oily substance.

¹H NMR (600 MHz, CHLOROFORM-d) d ppm 1.55 (s, 9H), 3.69 (s, 3H), 4.01 (s, 2H), 4.70 (s, 2H), 7.29-8.13 (m, 8H), 8.41 (s, 1H)

(5) To a solution of the compound (4.07 g) obtained in Example 153-(4) in chloroform (40 ml), trifluoroacetic acid (20 ml) was added in an ice bath, and the mixed solution was stirred in an ice bath for 30 min. Furthermore, the solution was stirred at room temperature for 3.5 hours, and then 1N sodium hydroxide aqueous solution was added to the solution in an ice bath to adjust the solution to pH5, followed by extraction with ethyl acetate. The organic layer washed with a saturated saline solution, then dried over anhydrous magnesium sulfate, and then evaporated under reduced pressure to remove the solvent to give 4-{[4-(2-methoxy-2-oxoethyl)isoquinolin-1-yl]methyl}benzoic acid (3.42 g) as a pale brown solid.

¹H NMR (600 MHz, DMSO-d₆) d ppm 3.62 (s, 3H), 4.13 (s, 2H), 4.71 (s, 2H), 7.39-8.36 (m, 8H), 8.37 (s, 1H), 12.79 (br. s., 1H)

(6) To a solution of the compound (2.69 g) obtained in Example 153-(5) in chloroform (40 ml), oxalyl chloride (1.07 ml) and N,N-dimethylformamide (3 drops) were added in an ice bath, and the mixed solution was stirred for one hour. The reaction solution was removed by evaporation under reduced pressure. To the resulting crude product, chloroform (40 ml) was added, and 2-(4-chlorophenyl)ethylamine (1.68 ml) and pyridine (0.973 ml) were added in an ice bath, and the resulting solution was stirred for one hour. The reaction solution was washed with a saturated solution of ammonium chloride, and the organic layer was dried over anhydrous magnesium sulfate, and evaporated under reduced pressure to remove the solvent. The resulting crude product was purified by column chromatography (NH type silica gel, ethyl acetate/n-hexane=10 to 100%) to give methyl [1-(4-{[2-(4-chlorophenyl)ethyl]carbamoyl}benzyl)isoquinolin-4-yl]acetate (1.31 g) as a pale yellow solid.

$^1$H NMR (600 MHz, CHLOROFORM-d) d ppm 2.87 (t, J=6.9 Hz, 2H), 3.61-3.67 (m, 2H), 3.70 (s, 3H), 4.01 (s, 2H), 4.68 (s, 2H), 6.04 (t, J=5.3 Hz, 1H), 7.11-8.13 (m, 12H), 8.40 (s, 1H)

(7) To a solution of the compound (1.31 g) obtained in Example 153-(6) in tetrahydrofuran (55 ml), 1N sodium hydroxide aqueous solution (14 ml) was added in an ice bath, and the mixed solution was stirred at room temperature for 2.5 hours. 1N aqueous hydrochloric acid solution was added to the solution in an ice bath to adjust the solution to pH5, followed by extraction with ethyl acetate. The organic layer was washed with a saturated saline solution, dried over anhydrous magnesium sulfate, and evaporated under reduced pressure to remove the solvent. The resulting crude product was purified by column chromatography (acidic OH type silica gel, methanol/chloroform=0 to 15%). To the obtained solid, diethyl ether was added, and the mixture was stirred at room temperature for 17 hours to be filtered out to give a pale yellow solid (1.05 g). The obtained solid was dissolved in ethanol (250 ml) at 40° C., and water (2500 ml) was added dropwise thereto, and the resulting solution was stirred at room temperature for 17 hours. The precipitated solid was filtered out and dried to give the titled compound (944 mg) as a pale yellow solid.

Compounds of Examples 154 to 160 were obtained by carrying out the same procedures as in Example 153. Structural formulae and NMR values of Examples 153 to 160 are shown in Table 6.

[Ka 28]

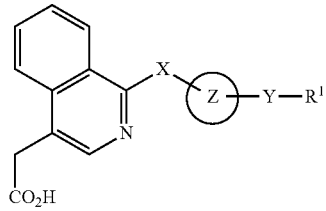

TABLE 6

| Example | X | Z | Y | R$^1$ | $^1$H NMR (d ppm) |
|---|---|---|---|---|---|
| 153 | -CH$_2$- | 1,4-phenylene | -C(=O)NH-CH$_2$CH$_2$- | 4-Cl-phenyl | $^1$H NMR (600 MHz, DMSO-d6) 2.79 (t, J = 7.3 Hz, 2 H), 3.39-3.46 (m, 2 H), 4.00 (s, 2 H), 4.67 (s, 2 H), 7.20-8.43 (m, 14 H) |
| 154 | -CH$_2$- | 1,4-phenylene | -C(=O)NH-CH$_2$- | 4-Cl-phenyl | $^1$H NMR (600 MHz, DMSO-d6) 3.98 (s, 2 H), 4.37-4.41 (m, 2 H), 4.65 (s, 2 H), 7.24-8.94 (m, 14 H) |
| 155 | -CH$_2$- | 1,4-phenylene | -C(=O)NH-CH$_2$CH$_2$- | 3-Cl-phenyl | $^1$H NMR (600 MHz, DMSO-d6) 2.79-2.84 (m, 2 H), 3.42-3.47 (m, 2 H), 3.98 (s, 2 H), 4.67 (s, 2 H), 7.14-8.45 (m, 14 H) |
| 156 | -CH$_2$- | 1,4-phenylene | -C(=O)NH-CH$_2$CH$_2$- | 4-OMe-phenyl | $^1$H NMR (600 MHz, DMSO-d6) 2.70-2.76 (m, 2 H), 3.37-3.42 (m, 2 H), 3.70 (s, 3 H), 4.01 (s, 2 H), 4.67 (s, 2 H), 6.79-8.42 (m, 14 H), 12.53 (br. s, 1 H) |
| 157 | -CH$_2$- | 1,4-phenylene | -C(=O)NH-CH$_2$CH$_2$- | 3-Cl-4-OMe-phenyl | $^1$H NMR (600 MHz, DMSO-d6) 2.71-2.75 (m, 2 H), 3.35-3.42 (m, 2 H), 3.79 (s, 3 H), 4.00 (s, 2 H), 4.66 (s, 2 H), 7.01-8.41 (m, 13 H) |
| 158 | -CH$_2$- | 1,4-phenylene | -C(=O)NH- | 3,4-diCl-phenyl | $^1$H NMR (600 MHz, DMSO-d6) 3.87 (br. s., 2 H), 4.71 (s, 2 H), 7.45-8.35 (m, 12 H), 10.39 (s, 1 H) |
| 159 | -CH$_2$- | 1,4-phenylene | -C(=O)NH- | 4-Cl-phenyl | $^1$H NMR (600 MHz, DMSO-d6) 3.88 (br. s., 2 H), 4.70 (s, 2 H), 7.36-8.35 (m, 13 H), 10.25 (s, 1 H) |

TABLE 6-continued

| Example | X | Z | Y | R[1] | $^1$H NMR (d ppm) |
|---|---|---|---|---|---|
| 160 | *CH2CH2* | *-C6H4-* | *-C(O)NH-CH2CH2-* | *-C6H3(Cl)(Cl)* | $^1$H NMR (600 MHz, DMSO-d6) 2.79-2.83 (m, 2 H), 3.42-3.47 (m, 2 H), 3.99 (s, 2 H), 4.67 (s, 2 H), 7.18-8.42 (m, 13 H) |

Example 161

(1-{4-[(2-phenylethyl)carbamoyl]benzyl}isoquinolin-4-yl)acetic acid (1) To a suspension of the compound (100 mg) obtained in Example 153-(5), 2-phenylethylamine (0.045 ml) and 1-hydroxybenzotriazole hydrate (55 mg) in chloroform (3 ml), 1-ethyl-3-(dimethylaminopropyl)-carbodiimide hydrochloride (69 mg) was added, and the mixture was stirred at room temperature for three hours. The reaction solution was washed with water, and evaporated under reduced pressure to remove the solvent. The resulting crude product was purified by column chromatography (NH type silica gel, ethyl acetate/n-hexane=60 to 100%) to give methyl (1-{4-[(2-phenylethyl)carbamoyl]benzyl}isoquinolin-4-yl)acetate (90 mg) as a pale brownish-colored solid.

$^1$H NMR (600 MHz, CHLOROFORM-d) d ppm 2.90 (t, J=6.9 Hz, 2H), 3.66-3.72 (m, 5H), 4.01 (s, 2H), 4.68 (s, 2H), 5.98-6.07 (m, 1H), 7.18-8.14 (m, 13H), 8.40 (s, 1H)

(2) The same procedure as used in Example 149-(4) was carried out using the compound (90 mg) obtained in Example 161-(1) to give the titled compound (73 mg) as a pale yellow solid.

Compounds of Examples 162 to 251 were obtained by carrying out the same procedures as in Example 161. Structural formulae and NMR values of Examples 161 to 251 are shown in Tables 7-1 to 7-9.

[Ka 29]

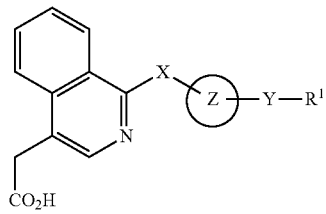

TABLE 7-1

| Example | X | Z | Y | R[1] | $^1$H NMR (d ppm) |
|---|---|---|---|---|---|
| 161 | *CH2CH2* | *-C6H4-* | *-C(O)NH-CH2CH2-* | *-C6H5* | $^1$H NMR (600 MHz, DMSO-d6) 2.80 (t, J = 7.3 Hz, 2 H), 3.41-3.46 (m, 2 H), 4.02 (s, 2 H), 4.68 (s, 2 H), 7.16-8.45 (m, 15 H), 12.52 (br. s., 1 H) |
| 162 | *CH2CH2* | *-C6H4-* | *-C(O)NH-CH2CH2-* | *-C6H4-Cl (o)* | $^1$H NMR (600 MHz, DMSO-d6) 2.91-2.97 (m, 2 H), 3.44-3.50 (m, 2 H), 4.01 (s, 2 H), 4.67 (s, 2 H), 7.21-8.49 (m, 14 H), 12.52 (br. s., 1 H) |
| 163 | *CH2CH2* | *-C6H4-* | *-C(O)NH-CH2CH2-* | *-C6H4-Cl (m)* | $^1$H NMR (600 MHz, DMSO-d6) 2.82 (t, J = 7.1 Hz, 2 H), 3.42-3.48 (m, 2 H), 4.01 (s, 2 H), 4.67 (s, 2 H), 7.14-8.45 (m, 14 H), 12.54 (br. s., 1 H) |
| 164 | *CH2CH2* | *-C6H4-* | *-C(O)NH-CH2CH2CH2-* | *-C6H4-Cl (p)* | $^1$H NMR (600 MHz, DMSO-d6) 1.74-1.80 (m, 2 H), 2.56-2.61 (m, 2 H), 3.19-3.25 (m, 2 H), 4.01 (s, 2 H), 4.67 (s, 2 H), 7.21-8.37 (m, 14 H), 12.54 (br. s., 1 H) |
| 165 | *CH2CH2* | *-C6H4-* | *-C(O)NH-CH2CH2-* | *-C6H4-Me (p)* | $^1$H NMR (600 MHz, DMSO-d6) 2.24 (s, 3 H), 2.75 (t, J = 7.6 Hz, 2 H), 3.36-3.43 (m, 2 H), 4.19 (s, 2 H), 4.90 (s, 2 H), 7.05-8.58 (m, 14 H) |
| 166 | *CH2CH2* | *-C6H4-* | *-C(O)NH-CH2CH2-* | *-C6H4-Me (m)* | $^1$H NMR (600 MHz, DMSO-d6) 2.26 (s, 3 H), 2.73-2.78 (m, 2 H), 3.38-3.44 (m, 2 H), 4.01 (s, 2 H), 4.67 (s, 2 H), 6.97-8.45 (m, 14 H) |

TABLE 7-1-continued

| Example | X | Z | Y | R¹ | ¹H NMR (d ppm) |
|---|---|---|---|---|---|
| 167 | 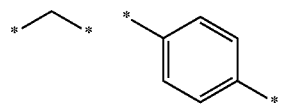 | 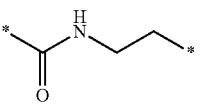 [SMILES: *CCNC(*)=O] | 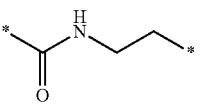 [SMILES: *CCNC(*)=O] | 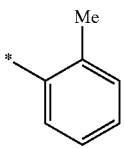 | ¹H NMR (600 MHz, DMSO-d6) 2.30 (s, 3 H), 2.77-2.82 (m, 2 H), 3.36-3.41 (m, 2 H), 4.01 (s, 2 H), 4.68 (s, 2 H), 7.05-8.52 (m, 14 H) |
| 168 | 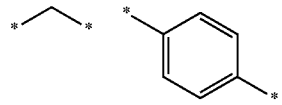 | 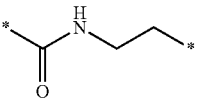 [SMILES: *CCNC(*)=O] | 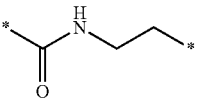 [SMILES: *CCNC(*)=O] | 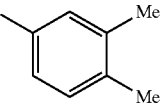 | ¹H NMR (600 MHz, DMSO-d6) 2.15 (s, 3 H), 2.17 (s, 3 H), 2.71 (t, J = 7.3 Hz, 2 H), 3.36-3.42 (m, 2 H), 4.02 (s, 2 H), 4.68 (s, 2 H), 6.88-8.43 (m, 13 H), 12.52 (br. s., 1 H) |
| 169 | 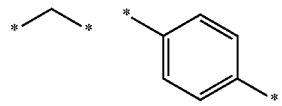 | 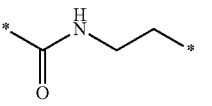 [SMILES: *CCNC(*)=O] | 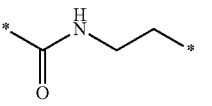 [SMILES: *CCNC(*)=O] | 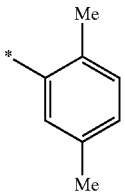 | ¹H NMR (600 MHz, DMSO-d6) 2.21 (s, 3 H), 2.24 (s, 3 H), 2.71-2.77 (m, 2 H), 3.33-3.38 (m, 2 H), 3.98 (s, 2 H), 4.67 (s, 2 H), 6.88-8.51 (m, 13 H) |
| 170 | 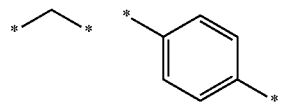 | 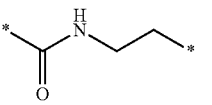 [SMILES: *CCNC(*)=O] | 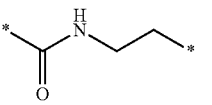 [SMILES: *CCNC(*)=O] | 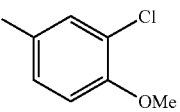 | ¹H NMR (600 MHz, DMSO-d6) 2.74 (t, J = 7.1 Hz, 2 H), 3.37-3.43 (m, 2 H), 3.80 (s, 3 H), 3.98 (s, 2 H), 4.67 (s, 2 H), 7.01-8.41 (m, 13 H) |
| 171 | 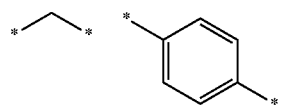 | 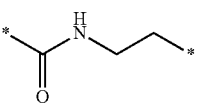 [SMILES: *CCNC(*)=O] | 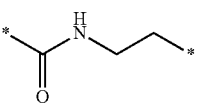 [SMILES: *CCNC(*)=O] | 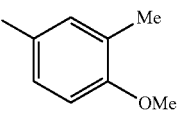 | ¹H NMR (600 MHz, DMSO-d6) 2.10 (s, 3 H), 2.69 (t, J = 7.3 Hz, 2 H), 3.35-3.40 (m, 2 H), 3.73 (s, 3 H), 3.99 (s, 2 H), 4.67 (s, 2 H), 6.80-8.42 (m, 13 H) |

TABLE 7-2

| Example | X | Z | Y | R¹ | ¹H NMR (d ppm) |
|---|---|---|---|---|---|
| 172 | 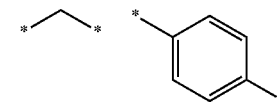 | 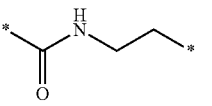 [SMILES: *CCNC(*)=O] | 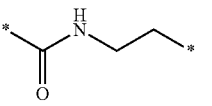 [SMILES: *CCNC(*)=O] | 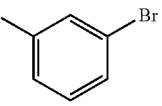 | ¹H NMR (600 MHz, DMSO-d6) 2.81 (t, J = 7.1 Hz, 2 H), 3.41-3.47 (m, 2 H), 4.01 (s, 2 H), 4.67 (s, 2 H), 7.19-8.44 (m, 14 H), 12.54 (br. s., 1 H) |
| 173 | 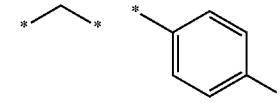 | 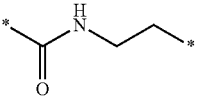 [SMILES: *CCNC(*)=O] | 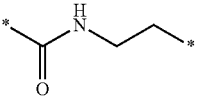 [SMILES: *CCNC(*)=O] | 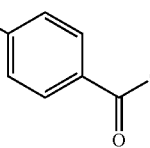 | ¹H NMR (600 MHz, DMSO-d6) 2.84 (t, J = 7.1 Hz, 2 H), 3.41-3.46 (m, 2 H), 3.98 (s, 2 H), 4.64 (s, 2 H), 7.28-8.43 (m, 14 H), 12.62 (br. s., 1 H) |
| 174 | 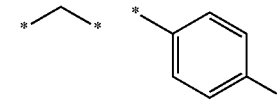 | 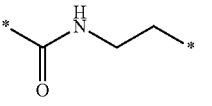 [SMILES: *CCNC(*)=O] | 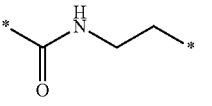 [SMILES: *CCNC(*)=O] | 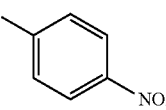 | ¹H NMR (600 MHz, DMSO-d6) 2.96 (t, J = 6.9 Hz, 2 H), 3.48-3.54 (m, 2 H), 4.01 (s, 2 H), 4.67 (s, 2 H), 7.34-8.47 (m, 14 H), 12.58 (br. s., 1 H) |
| 175 | 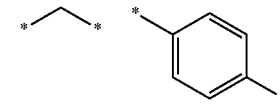 | 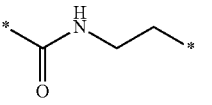 [SMILES: *CCNC(*)=O] | 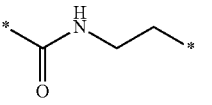 [SMILES: *CCNC(*)=O] | 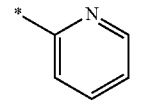 | ¹H NMR (600 MHz, DMSO-d6) 2.92-2.98 (m, 2 H), 3.53-3.59 (m, 2 H), 3.64 (br. s., 2 H), 4.63 (s, 2 H), 7.16-8.50 (m, 14 H) |
| 176 | 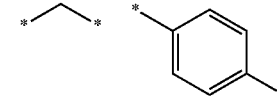 | 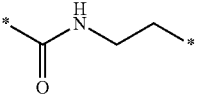 [SMILES: *CCNC(*)=O] | 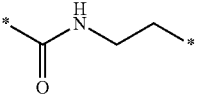 [SMILES: *CCNC(*)=O] | 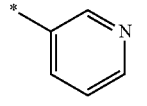 | ¹H NMR (600 MHz, DMSO-d6) 2.83 (t, J = 7.1 Hz, 2 H), 3.43-3.49 (m, 2 H), 3.99 (s, 2 H), 4.67 (s, 2 H), 7.27-8.46 (m, 14 H) |
| 177 | 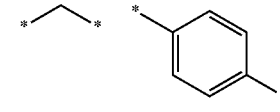 | 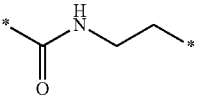 [SMILES: *CCNC(*)=O] | 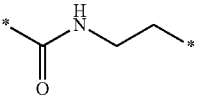 [SMILES: *CCNC(*)=O] | 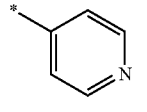 | ¹H NMR (600 MHz, DMSO-d6) 2.80-2.86 (m, 2 H), 3.45-3.51 (m, 2 H), 3.69 (br. s., 2 H), 4.63 (s, 2 H), 7.19-8.48 (m, 14 H) |

TABLE 7-2-continued

| Example | X | Z | Y | R¹ | ¹H NMR (d ppm) |
|---|---|---|---|---|---|
| 178 | 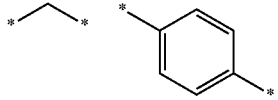 | 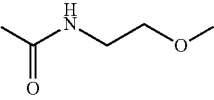 |  | 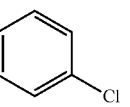 | ¹H NMR (600 MHz, DMSO-d6) 3.52-3.57 (m, 2 H), 3.97 (s, 2 H), 4.03 (t, J = 6.0 Hz, 2 H), 4.64 (s, 2 H), 6.90-8.56 (m, 14 H) |
| 179 | 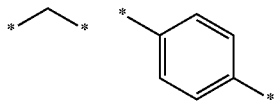 | 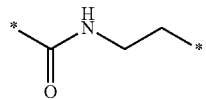 [SMILES: *CCNC(*)=O] | 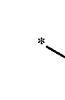 | 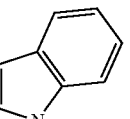 | ¹H NMR (600 MHz, DMSO-d6) 2.90 (t, J = 7.6 Hz, 2 H), 3.47-3.52 (m, 2 H), 4.01 (s, 2 H), 4.68 (s, 2 H), 6.94-8.50 (m, 15 H), 10.78 (br. s, 1 H) |
| 180 | 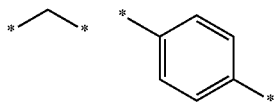 | 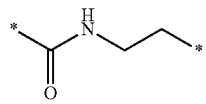 [SMILES: *CCNC(*)=O] |  | 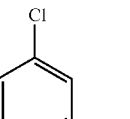 | ¹H NMR (600 MHz, DMSO-d6) 2.92 (t, J = 7.1 Hz, 2 H), 3.43-3.49 (m, 2 H), 4.01 (s, 2 H), 4.67 (s, 2 H), 7.30-8.47 (m, 13 H) |
| 181 | 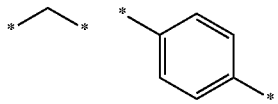 | 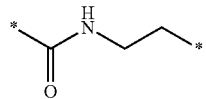 [SMILES: *CCNC(*)=O] |  | 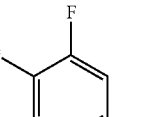 | ¹H NMR (600 MHz, DMSO-d6) 2.84 (t, J = 7.3 Hz, 2 H), 3.40-3.47 (m, 2 H), 3.93 (br. s., 2 H), 4.66 (s, 2 H), 7.08-8.49 (m, 14 H) |
| 182 | 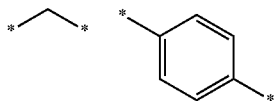 | 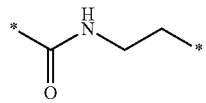 [SMILES: *CCNC(*)=O] |  | 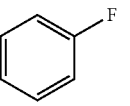 | ¹H NMR (600 MHz, DMSO-d6) 2.83 (t, J = 7.3 Hz, 2 H), 3.42-3.48 (m, 2 H), 4.06 (s, 2 H), 4.72 (s, 2 H), 6.97-8.46 (m, 14 H) |
| 183 | 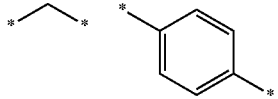 | 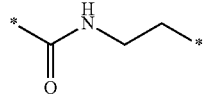 [SMILES: *CCNC(*)=O] |  | 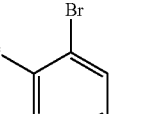 | ¹H NMR (600 MHz, DMSO-d6) 2.94 (t, J = 7.1 Hz, 2 H), 3.43-3.49 (m, 2 H), 4.02 (s, 2 H), 4.68 (s, 2 H), 7.12-8.50 (m, 14 H) |

TABLE 7-3

| Example | X | Z | Y | R¹ | ¹H NMR (d ppm) |
|---|---|---|---|---|---|
| 184 | 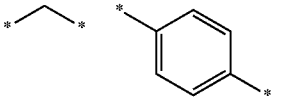 | 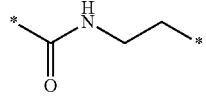 [SMILES: *CCNC(*)=O] |  | 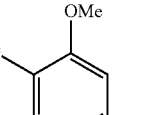 | ¹H NMR (600 MHz, DMSO-d6) 2.76-2.80 (m, 2 H), 3.37-3.42 (m, 2 H), 3.77 (s, 3 H), 4.04 (s, 2 H), 4.70 (s, 2 H), 6.81-8.42 (m, 14 H) |
| 185 | 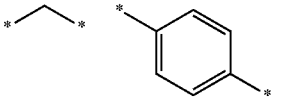 | 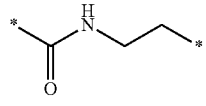 [SMILES: *CCNC(*)=O] |  | 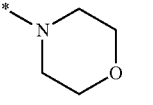 | ¹H NMR (600 MHz, DMSO-d6) 2.36-2.43 (m, 6 H), 2.60-2.62 (m, 2 H), 3.54 (s, 4 H), 3.95 (br. s., 2 H), 4.67 (s, 2 H), 7.32-8.36 (m, 10 H) |
| 186 | 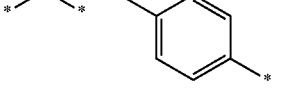 | 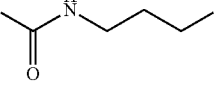 |  |  | ¹H NMR (600 MHz, DMSO-d6) 0.87 (t, J = 7.3 Hz, 3 H), 1.25-1.33 (m, 2 H), 1.43-1.49 (m, 2 H), 3.18-3.23 (m, 2 H), 4.01 (s, 2 H), 4.67 (s, 2 H), 7.34-8.38 (m, 10 H), 12.54 (br. s., 1 H) |
| 187 | 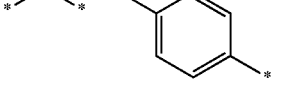 | 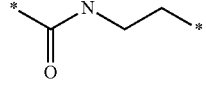 |  | 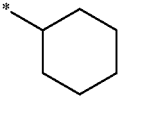 | ¹H NMR (600 MHz, DMO-d6) 0.82-1.72 (m, 13 H), 3.20-3.26 (m, 2 H), 4.01 (s, 2 H), 4.67 (s, 2 H), 7.34-8.39 (m, 10 H), 12.52 (br. s., 1 H) |

TABLE 7-3-continued

| Example | X | Z | Y | R¹ | ¹H NMR (d ppm) |
|---|---|---|---|---|---|
| 188 | *–CH₂CH₂–* | *–C₆H₄–* (para) | *–C(O)NH–CH₂CH₂–* | cyclohexenyl | ¹H NMR (600 MHz, DMSO-d6) 1.44-2.13 (m, 10 H), 3.25-3.30 (m, 2 H), 4.01 (s, 2 H), 4.67 (s, 2 H), 5.38 (br. s., 1 H), 7.33-8.37 (m, 10 H), 12.53 (br. s., 1 H) |
| 189 | *–CH₂CH₂–* | *–C₆H₄–* (para) | *–C(O)NH–CH₂CH₂–* | 3,4-dimethoxyphenyl | ¹H NMR (600 MHz, DMSO-d6) 2.73 (t, J = 7.3 Hz, 2 H), 3.38-3.44 (m, 2 H), 3.68 (s, 3 H), 3.69 (s, 3 H), 4.00 (s, 2 H), 4.67 (s, 2 H), 6.68-8.41 (m, 13 H) |
| 190 | *–CH₂CH₂–* | *–C₆H₄–* (para) | *–C(O)NH–CH₂CH₂–* | 2-chloro-6-fluorophenyl | ¹H NMR (600 MHz, DMSO-d6) 2.98 (t, J = 7.1 Hz, 2 H), 3.40-3.45 (m, 2 H), 3.98 (s, 2 H), 4.67 (s, 2 H), 7.15-8.54 (m, 13 H) |
| 191 | *–CH₂CH₂–* | *–C₆H₄–* (para) | *–C(O)NH–CH₂CH₂–* | 2,6-dichlorophenyl | ¹H NMR (600 MHz, DMSO-d6) 3.13 (t, J = 7.1 Hz, 2 H), 3.43-3.48 (m, 2 H), 4.00 (s, 2 H), 4.67 (s, 2 H), 7.24-8.55 (m, 13 H) |
| 192 | *–CH₂CH₂–* | *–C₆H₄–* (para) | *–C(O)NH–CH₂CH₂–* | pentamethylphenyl | ¹H NMR (600 MHz, DMSO-d6) 2.12-2.15 (m, 9 H), 2.24 (s, 6 H), 2.80-2.85 (m, 2 H), 3.17-3.23 (m, 2 H), 4.01 (s, 2 H), 4.69 (s, 2 H), 7.37-8.63 (m, 10 H) |
| 193 | *–CH₂CH₂–* | *–C₆H₄–* (para) | *–C(O)NH–CH₂CH₂–* | 4-tert-butylphenyl (isopropyl depicted: 4-(2-methylpropan-2-yl)phenyl) | ¹H NMR (600 MHz, CHLOROFORM-d) 1.29 (s, 9 H), 2.83 (t, J = 7.1 Hz, 2 H), 3.60-3.67 (m, 2 H), 4.01 (s, 2 H), 4.66 (s, 2 H), 6.27 (t, J = 6.0 Hz, 1 H), 7.10-8.11 (m, 12 H), 8.40 (s, 1 H) |

TABLE 7-4

| Example | X | Z | Y | R¹ | ¹H NMR (d ppm) |
|---|---|---|---|---|---|
| 194 | *–CH₂CH₂–* | *–C₆H₄–* (para) | *–C(O)NH–CH₂CH₂–* | biphenyl-4-yl | ¹H NMR (600 MHz, DMSO-d6) 2.85 (t, J = 7.3 Hz, 2 H), 3.44-3.50 (m, 2 H), 4.00 (s, 2 H), 4.67 (s, 2 H), 7.27-8.50 (m, 19 H) |
| 195 | *–CH₂CH₂–* | *–C₆H₄–* (para) | *–C(O)NH–CH₂CH₂–* | 4-phenoxyphenyl | ¹H NMR (600 MHz, DMSO-d6) 2.79 (t, J = 7.6 Hz, 2 H), 3.40-3.46 (m, 2 H), 3.99 (s, 2 H), 4.67 (s, 2 H), 6.89-8.45 (m, 19 H) |
| 196 | *–CH₂CH₂–* | *–C₆H₄–* (para) | *–C(O)NH–CH₂CH₂–* | 4-hydroxyphenyl | ¹H NMR (600 MHz, DMSO-d6) 2.67 (t, J = 7.6 Hz, 2 H), 3.34-3.39 (m, 2 H), 4.00 (s, 2 H), 4.67 (s, 2 H), 6.63-8.41 (m, 14 H), 9.15 (br. s., 1 H) |
| 197 | *–CH₂CH₂–* | *–C₆H₄–* (para) | *–C(O)NH–CH₂CH₂–* | 3-methoxyphenyl | ¹H NMR (600 MHz, DMSO-d6) 2.77 (t, J = 7.3 Hz, 2 H), 3.41-3.46 (m, 2 H), 3.69 (s, 3 H), 4.17 (br. s., 2 H), 4.87 (br. s., 2 H), 6.73-8.55 (m, 14 H) |

TABLE 7-4-continued

| Example | X | Z | Y | R¹ | ¹H NMR (d ppm) |
|---|---|---|---|---|---|
| 198 |  | 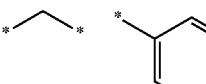 | 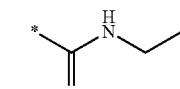 | 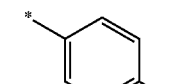 | ¹H NMR (600 MHz, DMSO-d6) 2.73 (t, J = 7.3 Hz, 2 H), 3.36-3.42 (m, 2 H), 3.70 (s, 3 H), 4.22 (s, 2 H), 4.94 (br. s., 2 H), 6.81-8.62 (m, 14 H) |
| 199 |  | 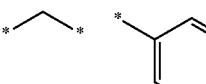 | 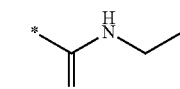 | 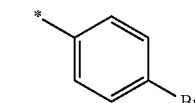 | ¹H NMR (600 MHz, DMSO-d6) 2.78 (t, J = 7.1 Hz, 2 H), 3.39-3.47 (m, 2 H), 4.23 (s, 2 H), 4.96 (br. s., 2 H), 7.15-8.64 (m, 14 H) |
| 200 |  | 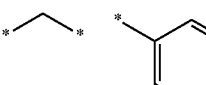 | 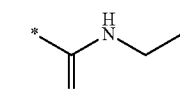 | 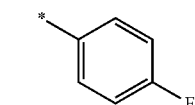 [SMILES: *c1ccc(*)cc1] | ¹H NMR (600 MHz, DMSO-d6) 2.79 (t, J = 7.3 Hz, 2 H), 3.39-3.45 (m, 2 H), 4.04 (s, 2 H), 4.70 (s, 2 H), 7.06-8.44 (m, 14H) |
| 201 |  | 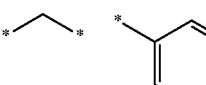 | 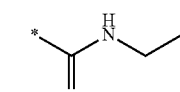 | 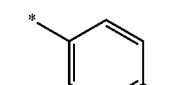 | ¹H NMR (600 MHz, DMSO-d6) 2.90 (t, J = 7.1 Hz, 2 H), 3.45-3.51 (m, 2 H), 4.01 (s, 2 H), 4.67 (s, 2 H), 7.34-8.48 (m, 14 H), 12.54 (br. s., 1 H) |
| 202 |  | 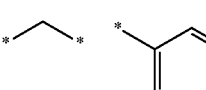 | 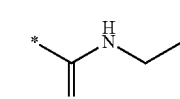 | 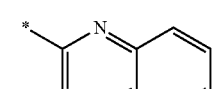 | ¹H NMR (600 MHz, DMSO-d6) 3.15 (t, J = 7.3 Hz, 2 H), 3.66-3.72 (m, 2 H), 4.01 (s, 2 H), 4.67 (s, 2 H), 7.35-8.52 (m, 16 H), 12.55 (br. s., 1 H) |
| 203 |  | 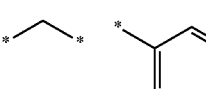 | 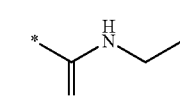 |  | ¹H NMR (600 MHz, DMSO-d6) 2.84 (t, J = 7.3 Hz, 2 H), 3.42-3.47 (m, 2 H), 4.00 (s, 2 H), 4.67 (s, 2 H), 7.24-8.46 (m, 14 H) |
| 204 |  | 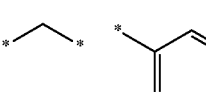 | 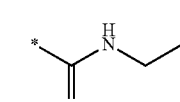 | 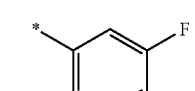 | ¹H NMR (600 MHz, DMSO-d6) 2.17 (s, 3 H), 2.78 (t, J = 7.3 Hz, 2 H), 3.40-3.45 (m, 2 H), 4.01 (s, 2 H), 4.67 (s, 2 H), 6.91-8.42 (m, 13 H) |

TABLE 7-5

| Example | X | Z | Y | R¹ | ¹H NMR (d ppm) |
|---|---|---|---|---|---|
| 205 |  | 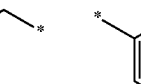 | 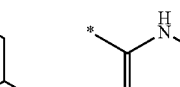 | 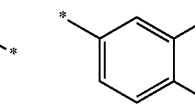 | ¹H NMR (600 MHz, DMSO-d6) 2.98 (t, J = 7.3 Hz, 2 H), 3.50-3.57 (m, 2 H), 4.01 (s, 2 H), 4.67 (s, 2 H), 7.33-8.51 (m, 17 H), 12.56 (br. s., 1 H) |
| 206 |  | 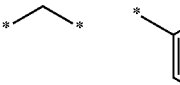 | 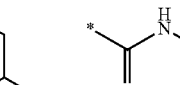 | 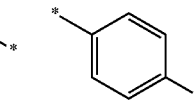 | ¹H NMR (600 MHz, DMSO-d6) 2.67 (t, J = 7.6 Hz, 2 H), 2.83 (s, 6 H), 3.32-3.38 (m, 2 H), 4.00 (s, 2 H), 4.67 (s, 2 H), 6.62-8.40 (m, 14 H) |
| 207 |  | 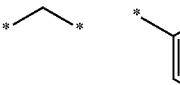 | 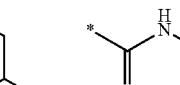 | 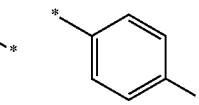 | ¹H NMR (600 MHz, DMSO-d6) 2.89-2.95 (m, 2 H), 3.17 (s, 3 H), 3.45-3.51 (m, 2 H), 4.00 (s, 2 H), 4.67 (s, 2 H), 7.35-8.47 (m, 14 H) |
| 208 |  |  | 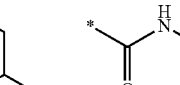 | 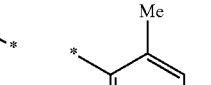 | ¹H NMR (600 MHz, DMSO-d6) 2.21 (s, 3 H), 2.26 (s, 3 H), 2.71-2.77 (m, 2 H), 3.30-3.39 (m, 2 H), 4.04 (s, 2 H), 4.71 (s, 2 H), 6.87-8.50 (m, 13 H) |

TABLE 7-5-continued

| Example | X | Z | Y | R¹ | ¹H NMR (δ ppm) |
|---|---|---|---|---|---|
| 209 |  | 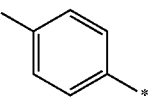 | 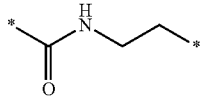 [SMILES: *CCNC(*)=O] | 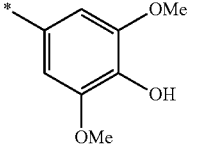 [SMILES: *c1cc(OC)c(O)c(OC)c1] | ¹H NMR (600 MHz, DMSO-d6) 2.69 (t, J = 7.3 Hz, 2 H), 3.37-3.43 (m, 2 H), 3.68 (s, 6 H), 4.01 (s, 2 H), 4.67 (s, 2 H), 6.44 (s, 2 H), 7.34-8.40 (m, 11 H), 12.55 (br. s., 1 H) |
| 210 |  | 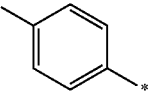 | 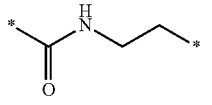 [SMILES: *CCNC(*)=O] | 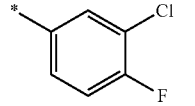 | ¹H NMR (600 MHz, DMSO-d6) 2.80 (t, J = 6.9 Hz, 2 H), 3.41-3.47 (m, 2 H), 4.01 (s, 2 H), 4.67 (s, 2 H), 7.18-8.42 (m, 13 H), 12.55 (br. s, 1 H) |
| 211 |  | 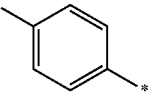 | 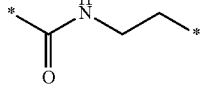 | 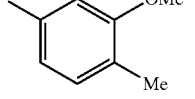 | ¹H NMR (600 MHz, DMSO-d6) 2.08 (s, 3 H), 2.76 (t, J = 7.3 Hz, 2 H), 3.40-3.46 (m, 2 H), 3.71 (s, 3 H), 4.02 (s, 2 H), 4.68 (s, 2 H), 6.65-8.44 (m, 13 H), 12.53 (br. s., 1 H) |
| 212 |  | 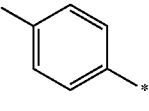 | 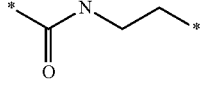 | 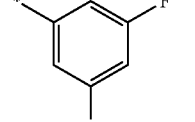 | ¹H NMR (600 MHz, DMSO-d6) 2.84 (t, J = 6.9 Hz, 2 H), 3.43-3.50 (m, 2 H), 4.01 (s, 2 H), 4.67 (s, 2 H), 6.92-8.46 (m, 13 H), 12.55 (br. s., 1 H) |
| 213 |  | 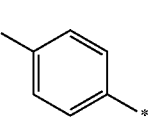 | 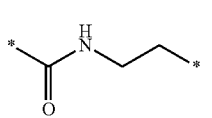 [SMILES: *CCNC(*)=O] | 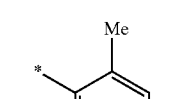 | ¹H NMR (600 MHz, DMSO-d6) 2.25 (s, 3 H), 2.79 (t, J = 7.6 Hz, 2 H), 3.38-3.43 (m, 2 H), 4.01 (s, 2 H), 4.68 (s, 2 H), 6.88-8.52 (m, 13 H), 12.55 (br. s., 1 H) |
| 214 |  | 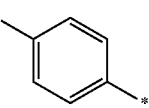 | 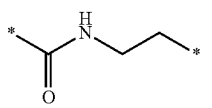 [SMILES: *CCNC(*)=O] | 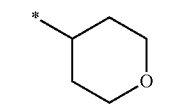 | ¹H NMR (600 MHz, DMSO-d6) 1.07-1.61 (m, 7 H), 3.20-3.28 (m, 4 H), 3.77-3.83 (m, 2 H), 4.01 (s, 2 H), 4.67 (s, 2 H), 7.35-8.37 (m, 10 H), 12.57 (br. s., 1 H) |

TABLE 7-6

| Example | X | Z | Y | R¹ | ¹H NMR (δ ppm) |
|---|---|---|---|---|---|
| 215 |  | 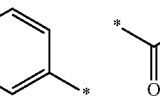 | 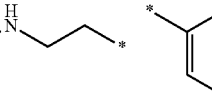 | 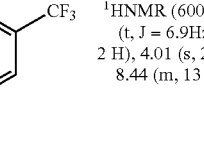 | ¹HNMR (600 MHz, DMSO-d6) 2.93 (t, J = 6.9Hz, 2 H), 3.47-3.53 (m, 2 H), 4.01 (s, 2 H), 4.67 (s, 2 H), 7.33-8.44 (m, 13 H), 12.52 (br. s., 1 H) |
| 216 |  | 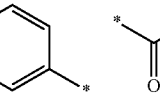 | 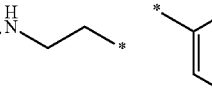 | 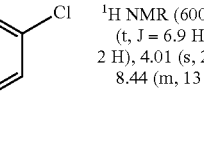 | ¹H NMR (600 MHz, DMSO-d6) 2.83 (t, J = 6.9 Hz, 2 H), 3.44-3.49 (m, 2 H), 4.01 (s, 2 H), 4.67 (s, 2 H), 7.05-8.44 (m, 13 H), 12.52 (br. s., 1 H) |
| 217 |  | 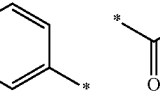 | 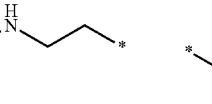 | 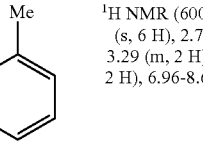 | ¹H NMR (600 MHz, DMSO-d6) 2.33 (s, 6 H), 2.77-2.83 (m, 2 H), 3.23-3.29 (m, 2 H), 4.01 (s, 2 H), 4.68 (s, 2 H), 6.96-8.65 (m, 13 H), 12.58 (br. s., 1 H) |

TABLE 7-6-continued

| Example | X | Z | Y | R¹ | ¹H NMR (d ppm) |
|---|---|---|---|---|---|
| 218 |  | 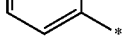 |  | 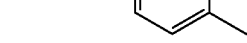 | ¹H NMR (600 MHz, DMSO-d6) 1.66-1.72 (m, 4 H), 2.62-2.68 (m, 4 H), 2.70 (t, J = 7.3 Hz, 2 H), 3.35-3.41 (m, 2 H), 4.01 (s, 2 H), 4.67 (s, 2 H), 6.87-8.43 (m, 13 H), 12.55 (br. s., 1 H) |
| 219 |  | 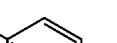 |  |  | ¹H NMR (600 MHz, DMSO-d6) 2.82 (t, J = 6.9 Hz, 2 H), 3.42-3.50 (m, 2 H), 4.07 (s, 2 H), 4.74 (br. s., 2 H), 7.27-8.45 (m, 13 H), 12.60 (br. s., 1 H) |
| 220 |  | 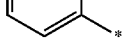 |  |  | ¹H NMR (600 MHz, DMSO-d6) 2.73 (d, J = 4.6 Hz, 3 H), 4.00 (s, 2 H), 4.67 (s, 2 H), 7.32-8.38 (m, 10 H) |
| 221 |  |  |  |  | ¹H NMR (600 MHz, DMSO-d6) 2.82 (t, J = 7.1 Hz, 2 H), 3.42-3.48 (m, 2 H), 4.00 (s, 2 H), 4.67 (s, 2 H), 7.03-8.44 (m, 13 H) |
| 222 |  | 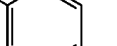 | 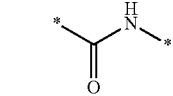 |  | ¹H NMR (600 MHz, DMSO-d6) 3.03 (t, J = 6.9 Hz, 2 H), 3.49-3.56 (m, 2 H), 4.01 (s, 2 H), 4.67 (s, 2 H), 7.33-8.43 (m, 13 H) |
| 223 |  | 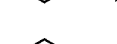 |  |  | ¹H NMR (600 MHz, DMSO-d6) 2.90 (t, J = 7.1 Hz, 2 H), 3.45-3.50 (m, 2 H), 4.00 (s, 2 H), 4.67 (s, 2 H), 7.33-8.46 (m, 14 H), 12.57 (br. s., 1 H) |
| 224 |  | 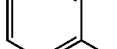 |  |  | ¹H NMR (600 MHz, DMSO-d6) 2.93 (t, J = 7.1 Hz, 2 H), 3.45-3.50 (m, 2 H), 3.97 (br. s., 2 H), 4.67 (s, 2 H), 7.28-8.47 (m, 13 H) |

TABLE 7-7

| Example | X | Z | Y | R¹ | ¹H NMR (d ppm) |
|---|---|---|---|---|---|
| 225 |  | 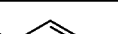 |  | 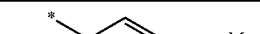 | ¹H NMR (600 MHz, DMSO-d6) 1.22 (d, J = 6.0 Hz, 6 H), 2.72 (t, J = 7.3 Hz, 2 H), 3.36-3.41 (m, 2 H), 4.01 (s, 2 H), 4.49-4.56 (m, 1 H), 4.67 (s, 2 H), 6.77-8.43 (m, 14 H), 12.57 (br. s., 1 H) |
| 226 |  |  |  |  | ¹H NMR (600 MHz, DMSO-d6) 2.99 (t, J = 7.1 Hz, 2 H), 3.45-3.52 (m, 2 H), 4.00 (s, 2 H), 4.67 (s, 2 H), 7.23-8.49 (m, 13 H), 12.59 (br. s., 1 H) |
| 227 |  |  |  | 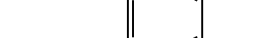 | ¹H NMR (600 MHz, DMSO-d6) 2.90 (t, J = 7.3 Hz, 2 H), 3.52-3.58 (m, 2 H), 3.80 (br. s., 2 H), 4.65 (s, 2 H), 6.78-8.52 (m, 15 H) |

TABLE 7-7-continued

| Example | X | Z | Y | R¹ | ¹H NMR (d ppm) |
|---|---|---|---|---|---|
| 228 | ethylene | 1,4-phenylene | *-C(=O)-NH-CH2CH2-* | 2-chloro-4-fluorophenyl | ¹H NMR (600 MHz, DMSO-d6) 2.93 (t, J = 6.9 Hz, 2 H), 3.45-3.52 (m, 2 H), 4.01 (s, 2 H), 4.67 (s, 2 H), 7.06-8.49 (m, 13 H), 12.54 (br. s., 1 H) |
| 229 | ethylene | 1,4-phenylene | *-C(=O)-NH-CH2CH2-* | 3,4-difluorophenyl | ¹H NMR (600 MHz, DMSO-d6) 2.80 (t, J = 7.1 Hz, 2 H), 3.41-3.47 (m, 2 H), 4.01 (s, 2 H), 4.67 (s, 2 H), 7.01-8.43 (m, 13 H), 12.55 (br. s., 1 H) |
| 230 | ethylene | 1,4-phenylene | *-C(=O)-NH-CH2CH2-* | benzothiophen-3-yl | ¹H NMR (600 MHz, DMSO-d6) 3.06 (t, J = 7.1 Hz, 2 H), 3.53-3.58 (m, 2 H), 4.01 (s, 2 H), 4.68 (s, 2 H), 7.33-8.57 (m, 15 H), 12.55 (br. s., 1 H) |
| 231 | ethylene | 1,4-phenylene | *-C(=O)-NH-CH2CH2-* | 3,5-dimethylphenyl | ¹H NMR (600 MHz, DMSO-d6) 2.21 (s, 6 H), 2.68-2.73 (m, 2 H), 3.36-3.42 (m, 2 H), 4.00 (s, 2 H), 4.67 (s, 2 H), 6.78-8.46 (m, 13 H), 12.59 (br. s., 1 H) |
| 232 | ethylene | 1,4-phenylene | *-C(=O)-NH-CH2CH2-* | 3-fluoro-4-methoxyphenyl | ¹H NMR (600 MHz, DMSO-d6) 2.74 (t, J = 7.1 Hz, 2 H), 3.37-3.45 (m, 2 H), 3.78 (s, 3 H), 4.00 (s, 2 H), 4.67 (s, 2 H), 6.93-8.43 (m, 13 H), 12.60 (br. s., 1 H) |
| 233 | ethylene | 1,4-phenylene | *-C(=O)-NH-CH2CH2-* | 2-chloro-4-fluorophenyl | ¹H NMR (600 MHz, DMSO-d6) 2.91 (t, J = 7.1 Hz, 2 H), 3.42-3.49 (m, 2 H), 4.01 (s, 2 H), 4.67 (s, 2 H), 7.10-8.47 (m, 13 H), 12.59 (br. s., 1 H) |
| 234 | ethylene | 1,4-phenylene | *-C(=O)-NH-CH2CH2-* | 5-chloro-1H-indol-2-yl | ¹H NMR (600 MHz, DMSO-d6) 2.94 (t, J = 7.3 Hz, 2 H), 3.53-3.59 (m, 2 H), 3.98 (s, 2 H), 4.67 (s, 2 H), 6.17-8.52 (m, 14 H), 11.19 (s, 1 H), 12.63 (br. s., 1 H) |

TABLE 7-8

| Example | X | Z | Y | R¹ | ¹H NMR (d ppm) |
|---|---|---|---|---|---|
| 235 | ethylene | 1,4-phenylene | *-C(=O)-NH-CH2CH2-* | 5-fluoro-1H-indol-2-yl | ¹H NMR (600 MHz, DMSO-d6) 2.94 (t, J = 7.3 Hz, 2 H), 3.52-3.59 (m, 2 H), 3.98 (br. s., 2 H), 4.67 (s, 2 H), 6.16-8.53 (m, 14 H), 11.08 (s, 1 H), 12.56 (br. s., 1 H) |

TABLE 7-8-continued

| Example | X | Z | Y | R¹ | ¹H NMR (d ppm) |
|---|---|---|---|---|---|
| 236 | ethylene | 1,4-phenylene | -C(O)NH-CH2CH2- | 5-methoxy-1H-indol-2-yl | ¹H NMR (600 MHz, DMSO-d6) 2.92 (t, J = 7.3 Hz, 2 H), 3.51-3.58 (m, 2 H), 3.71 (s, 3 H), 4.01 (s, 2 H), 4.67 (s, 2 H), 6.08-8.52 (m, 14 H), 10.79 (s, 1 H), 12.53 (br. s., 1 H) |
| 237 | ethylene | 1,4-phenylene | -C(O)NH-CH2CH2- | 4-cyclohexylphenyl | ¹H NMR (600 MHz, DMSO-d6) 1.15-1.41 (m, 5 H), 1.63-1.81 (m, 5 H), 2.39-2.47 (m, 1 H), 2.75 (t, J = 7.6 Hz, 2H), 3.37-3.43 (m, 2 H), 4.00 (s, 2 H), 4.67 (s, 2 H), 7.08-8.49 (m, 14 H), 12.56 (br. s., 1 H) |
| 238 | ethylene | 1,4-phenylene | -C(O)NH-CH2CH2- | 4-hexylphenyl | ¹H NMR (600 MHz, DMSO-d6) 0.81-0.87 (m, 3 H), 1.22-1.30 (m, 6 H), 1.48-1.56 (m, 2 H), 2.48-2.54 (m, 2 H), 2.75 (t, J = 7.6 Hz, 2 H), 3.37-3.44 (m, 2 H), 4.00 (s, 2 H), 4.67 (s, 2 H), 7.05-8.44 (m, 14 H), 12.52 (br. s., 1 H) |
| 239 | ethylene | 1,4-phenylene | -C(O)NH-CH2CH2- | cyclopropyl | ¹H NMR (600 MHz, DMSO-d6) 0.00-0.06 (m, 2 H), 0.34-0.42 (m, 2 H), 0.64-0.74 (m, 1 H), 1.33-1.44 (m, 2 H), 3.23-3.32 (m, 2 H), 4.00 (s, 2 H), 4.67 (s, 2 H), 7.32-8.40 (m, 10 H), 12.57 (br. s., 1 H) |
| 240 | ethylene | 1,4-phenylene | -C(O)NH-CH2CH2- | 1-adamantyl | ¹H NMR (600 MHz, DMSO-d6) 1.24-1.70 (m, 14 H), 1.87-1.95 (m, 3 H), 3.18-3.26 (m, 2 H), 4.00 (s, 2 H), 4.67 (s, 2 H), 7.32-8.37 (m, 10 H), 12.57 (br. s., 1 H) |
| 241 | ethylene | 1,4-phenylene | -C(O)NH-CH2CH2- | 4-(propoxy)phenyl-ethyl | ¹H NMR (600 MHz, DMSO-d6) 0.95 (t, J = 7.3 Hz, 3H), 1.65-1.73 (m, 2 H), 2.72 (t, J = 7.3 Hz, 2 H), 3.35-3.42 (m, 2 H), 3.86 (t, J = 6.6 Hz, 2 H), 4.01 (s, 2 H), 4.67 (s, 2 H), 6.78-8.43 (m, 14 H), 12.57 (br. s, 1 H) |
| 242 | ethylene | 1,4-phenylene | -C(O)NH-CH2CH2- | 5-methylbenzo[b]thiophen-2-yl | ¹H NMR (600 MHz, DMSO-d6) 2.38 (s, 3 H), 3.10 (t, J = 7.1 Hz, 2 H), 3.50-3.57 (m, 2 H), 4.00 (s, 2 H), 4.68 (s, 2 H), 7.06-8.59 (m, 14 H), 12.54 (br. s., 1 H) |
| 243 | ethylene | 1,4-phenylene | -C(O)NH-CH2CH2- | 2-phenoxyphenyl | ¹H NMR (600 MHz, DMSO-d6) 2.78 (t, J = 7.1 Hz, 2 H), 3.39-3.46 (m, 2 H), 4.00 (s, 2 H), 4.67 (s, 2 H), 6.79-8.42 (m, 19 H) |

TABLE 7-9

| Example | X | Z | Y | R¹ | ¹H NMR (d ppm) |
|---|---|---|---|---|---|
| 244 | *-CH₂-CH₂-* | *-C₆H₄-* (para) | *-C(O)-NH-CH₂-CH₂-* | 2-F, 3-Cl phenyl (*) | ¹H NMR (600 MHz, DMSO-d6) 2.88 (t, J = 6.9 Hz, 2 H), 3.42-3.49 (m, 2 H), 4.00 (s, 2 H), 4.67 (s, 2 H), 7.10-8.48 (m, 13 H) |
| 245 | *-CH₂-CH₂-* | *-C₆H₄-* (para) | *-C(O)-NH-CH₂-CH₂-* | 2-Me, 4-Cl phenyl (*) | ¹H NMR (600 MHz, DMSO-d6) 2.27 (s, 3 H), 2.76 (t, J = 7.3 Hz, 2 H), 3.38-3.45 (m, 2 H), 4.00 (s, 2 H), 4.67 (s, 2 H), 7.02-8.44 (m, 13 H) |
| 246 | *-CH₂-CH₂-* | *-C₆H₄-* (para) | *-C(O)-NH-CH₂-(cyclopropyl)-* | 4-Cl phenyl (*) | ¹H NMR (600 MHz, DMSO-d6) 0.70-0.75 (m, 2 H), 0.92-0.96 (m, 2 H), 3.47 (d, J = 6.0 Hz, 2 H), 4.00 (s, 2 H), 4.66 (s, 2 H), 7.26-8.36 (m, 14 H), 12.57 (br. s., 1 H) |
| 247 | *-CH₂-CH₂-* | *-C₆H₄-* (para) | *-C(O)-NH-CH₂-CH₂-NH-C(O)-* | 4-Cl phenyl (*) | ¹H NMR (600 MHz, DMSO-d6) 3.36-3.42 (m, 4 H), 4.00 (s, 2 H), 4.67 (s, 2 H), 7.35-8.65 (m, 15 H), 12.55 (br. s., 1 H) |
| 248 | *-CH₂-CH₂-* | *-C₆H₄-* (para) | *-C(O)-NH-CH₂-CH₂-* | 2-benzimidazolyl (*) | ¹H NMR (600 MHz, DMSO-d6) 3.04 (t, J = 7.3 Hz, 2 H), 3.64-3.69 (m, 2 H), 3.98 (s, 2 H), 4.67 (s, 2 H), 7.07-8.59 (m, 14 H), 12.24 (br. s., 1 H) |
| 249 | *-CH₂-CH₂-* | *-C₆H₄-* (para) | *-C(O)-NH-CH₂-CH₂-* | 2-benzofuranyl (*) | ¹H NMR (600 MHz, DMSO-d6) 3.01 (t, J = 6.9 Hz, 2 H), 3.56-3.62 (m, 2 H), 3.99 (s, 2 H), 4.67 (s, 2 H), 6.61-8.57 (m, 15 H), 12.57 (br. s, 1 H) |
| 250 | *-CH₂-CH₂-* | *-C₆H₄-* (para) | *-C(O)-NH-CH₂-CH₂-* | 2-benzothiazolyl (*) | ¹H NMR (600 MHz, DMSO-d6) 3.31-3.36 (m, 2 H), 3.65-3.72 (m, 2 H), 4.00 (s, 2 H), 4.67 (s, 2 H), 7.34-8.64 (m, 14 H), 12.57 (br. s., 1 H) |
| 251 | *-CH₂-CH₂-* | *-C₆H₄-* (para) | *-C(O)-NH-CH₂-C(Me)₂-* | 4-Cl phenyl (*) | ¹H NMR (600 MHz, DMSO-d6) 1.25 (s, 6 H), 3.39 (d, J = 6.4 Hz, 2 H), 3.99 (s, 2 H), 4.66 (s, 2 H), 7.29-8.35 (m, 14 H) |

Example 252

(1-{2-[(4-chlorobenzyl)oxy]benzyl}isoquinolin-4-yl) acetic acid (1) The same procedure as used in Example 153-(1) was carried out using 2-methoxybenzyl chloride (3.81 g) to give tributyl(2-methoxybenzyl)phosphonium chloride (8.13 g) as a colorless solid.

¹H NMR (600 MHz, CHLOROFORM-d) d ppm 0.89-0.97 (m, 9H), 1.38-1.51 (m, 12H), 2.37-2.47 (m, 6H), 3.85 (s, 3H), 4.10-4.16 (m, 2H), 6.87-7.75 (m, 4H)

(2) The same procedure as used in Example 153-(2) was carried out using the compound (2.27 g) obtained in Example 252-(1) to give methyl 1-(2-methoxybenzyl)isoquinoline-4-carboxylate (436 mg) as a pale orange-colored solid.

¹H NMR (600 MHz, CHLOROFORM-d) d ppm 3.89 (s, 3H), 4.01 (s, 3H), 4.71 (s, 2H), 6.75-8.99 (m, 8H), 9.13 (s, 1H)

(3) The same procedure as used in Example 153-(3) was carried out using the compound (436 mg) obtained in Example 252-(2) to give 1-(2-methoxybenzyl)isoquinoline-4-carboxylic acid (335 mg) as a pale yellow solid.

¹H NMR (600 MHz, DMSO-d₆) d ppm 3.82 (s, 3H), 4.63 (s, 2H), 6.76-8.93 (m, 8H), 8.96 (s, 1H), 13.38 (br. s., 1H)

(4) The same procedure as used in Example 153-(4) was carried out using the compound (335 mg) obtained in Example 252-(3) to give methyl [142-methoxybenzyl)isoquinolin-4-yl]acetate (108 mg) as a brown oily substance.

¹H NMR (600 MHz, CHLOROFORM-d) d ppm 3.69 (s, 3H), 3.91 (s, 3H), 4.01 (s, 2H), 4.65 (s, 2H), 6.75-8.24 (m, 8H), 8.40 (s, 1H)

(5) The same procedure as used in Example 149-(2) was carried out using the compound (70 mg) obtained in Example 252-(4) to give methyl [1-(2-hydroxybenzyl)isoquinolin-4-yl]acetate (39 mg) as a yellow solid.

¹H NMR (600 MHz, CHLOROFORM-d) d ppm 3.68 (s, 3H), 3.98 (s, 2H), 4.60 (s, 2H), 6.79-8.52 (m, 9H), 11.41 (br. s., 1H)

(6) The same procedure as used in Example 134-(5) was carried out using the compound (39 mg) obtained in Example 252-(5) and 4-chlorobenzyl bromide (42 mg) to give methyl {1-[2-(4-chlorobenzyloxy)benzyl]isoquinolin-4-yl}acetate (57 mg) as a yellow oily substance.

¹H NMR (600 MHz, CHLOROFORM-d) d ppm 3.69 (s, 3H), 4.00 (s, 2H), 4.68 (s, 2H), 5.08 (s, 2H), 6.81-8.20 (m, 12H), 8.38 (s, 1H)

(7) The same procedure as used in Example 149-(4) was carried out using the compound (57 mg) obtained in Example 252-(6) to give the titled compound (25 mg) as a pale yellow solid.

Example 253

[1-(4-{[2-(4-chlorophenyl)ethyl]carbamoyl}benzyl)-6-fluoroisoquinoline-4-yl]acetic acid (1) To methyl 6-fluoro-1oxo-1,2-dihydroisoquinoline-4-carboxylate (756 mg), phosphoryl chloride (5 ml) was added, and the mixture stirred at 100° C. for one hour. The resulting solution was returned to room temperature, and evaporated under reduced pressure to remove the solvent. To the resulting crude product, saturated sodium bicarbonate water was added, followed by extraction with ethyl acetate. The organic layer was washed with a saturated saline solution, dried over anhydrous magnesium sulfate, and evaporated under reduced pressure to remove the solvent to give methyl 1-chloro-6-fluoroisoquinoline-4-carboxylate (792 mg) as a brown solid.

¹H NMR (600 MHz, CHLOROFORM-d) d ppm 4.03 (s, 3H), 7.48-8.77 (m, 3H), 8.97 (s, 1H)

(2) To a solution of 4-(bromomethyl)benzoic acid (5.00 g) in chloroform (40 ml), oxalyl chloride (4 ml) and N,N-dimethylformamide (2 drops) were added in an ice bath, and the mixed solution was stirred at room temperature for three hours. The reaction solution was removed by evaporation under reduced pressure, and to the resulting crude product, toluene (70 ml) and n-hexane (70 ml) were added. The resulting solution was stirred at room temperature while 2-(4-chlorophenyl)ethylamine (3.02 g) and pyridine (1.6 ml) were added dropwise. The resulting solution was stirred at room temperature for 65 hours, and then 1N aqueous hydrochloric acid solution was added thereto, followed by extraction with ethyl acetate. The organic layer was washed with a saturated saline solution, dried over anhydrous magnesium sulfate, and evaporated under reduced pressure to remove the solvent. The resulting crude product was purified by column chromatography (neutral OH type silica gel, ethyl acetate/n-hexane=10 to 80%) to give 4-(bromomethyl)-N-[2-(4-chlorophenyl)ethyl]benzamide (4.36 g) as a colorless solid.

¹H NMR (600 MHz, DMSO-d₆) d ppm 2.84 (t, J=7.1 Hz, 2H), 3.44-3.51 (m, 2H), 4.73 (s, 1H), 4.80 (s, 1H), 7.22-7.83 (m, 8H), 8.51-8.59 (m, 1H)

(3) The same procedure as used in Example 153-(1) was carried out using the compound (4.35 g) obtained in Example 253-(2) to give tributyl(4-{[2-(4-chlorophenyl)ethyl]carbamoyl}benzyl)phosphonium bromide (6.01 g) as a colorless solid.

¹H NMR (600 MHz, CHLOROFORM-d) d ppm 0.86-0.96 (m, 9H), 1.40-1.50 (m, 12H), 2.28-2.38 (m, 6H), 3.00 (t, J=7.6 Hz, 2H), 3.67-3.74 (m, 2H), 4.36-4.42 (m, 2H), 7.21-7.90 (m, 9H)

(4) To a solution of the compound (787 mg) obtained in Example 253-(1) and compound (2.19 g) obtained in Example 253-(3) in tetrahydrofuran (15 ml), sodium bis(trimethylsilyl)amide (5.5 ml, 1.9 M solution) was added dropwise at −30° C., and the solution was stirred at room temperature for one hour. Furthermore, the solution was stirred at 50° C. for two hours, and then, a solution of sodium carbonate (695 mg) in water (7 ml) was added. The solution was stirred at 60° C. for five hours. The solution was stirred at room temperature for 16 hours, and then 1N aqueous hydrochloric acid solution was added, followed by extraction with ethyl acetate. The organic layer was washed with a saturated saline solution, dried over anhydrous magnesium sulfate, and evaporated under reduced pressure to remove the solvent. The resulting crude product was purified by column chromatography (neutral OH type silica gel, methanol/chloroform=10%) to give 1-(4-{[2-(4-chlorophenyl)ethyl]carbamoyl}benzyl)-6-fluoroisoquinoline-4-carboxylic acid (180 mg) as a colorless solid.

¹H NMR (600 MHz, DMSO-d₆) d ppm 2.80 (t, J=7.3 Hz, 2H), 3.40-3.47 (m, 2H), 4.77 (s, 2H), 7.21-8.71 (m, 12H), 9.07 (s, 1H), 13.55 (br. s., 1H)

(5) The same procedure as used in Example 15245) was carried out using the compound (173 mg) obtained in Example 253-(4) to give the titled compound (5 mg) as a colorless solid.

Example 254

2-[1-(4-{[2-(4-chlorophenyl)ethyl]carbamoyl}benzyl)isoquinolin-4-yl]propanoic acid (1) To a solution of the compound (500 mg) obtained in Example 153-(4) in tetrahydrofuran (5 ml), tert-butoxy potassium (150 mg) was added at −30° C., and the mixed solution was stirred for 5 min, and then methyl iodide (0.159 ml) was added. The mixed solution was stirred for 1.5 hours. Furthermore, methyl iodide (0.159 ml) was added thereto at −30° C., and the solution was stirred for 1.5 hours, and a saturated aqueous ammonium chloride solution was added, followed by extraction with ethyl acetate. The organic layer was dried over anhydrous magnesium sulfate, and evaporated under reduced pressure to remove the solvent. The resulting crude product was purified by column chromatography (neutral OH type silica gel, ethyl acetate/n-hexane=10 to 20%) to give tert-butyl 4-{[4-(1-methoxy-1-oxopropan-2-yl)isoquinolin-1-yl]methyl}benzoate (319 mg) as a yellow oily substance.

¹H NMR (600 MHz, CHLOROFORM-d) d ppm 1.55 (s, 9H), 1.70 (d, J=7.0 Hz, 3H), 3.67 (s, 3H), 4.36 (q, J=7.0 Hz, 1H), 4.70 (s, 2H), 7.30-8.14 (m, 8H), 8.45 (s, 1H)

(2) The same procedure as used in Example 15345) was carried out using the compound (319 mg) obtained in Example 254-(1) to give 4-{[4-(1-methoxy-1-oxopropan-2-yl)isoquinolin-1-yl]methyl}benzoic acid (254 mg) as a pale yellow solid.

¹H NMR (600 MHz, DMSO-d₆) d ppm 1.58 (d, J=6.9 Hz, 3H), 3.59 (s, 3H), 4.56 (q, J=6.9 Hz, 1H), 4.73 (s, 2H), 7.42-8.41 (m, 9H)

(3) The same procedure as used in Example 161-(1) was carried out using the compound (254 mg) obtained in Example 254-(2) to give methyl 2-[1-(4-{[2-(4-chlorophenyl)ethyl]carbamoyl}benzyl)isoquinolin-4-yl]propanoate (234 mg) as a pale yellow amorphous substance.

¹H NMR (600 MHz, CHLOROFORM-d) d ppm 1.70 (d, J=7.2 Hz, 3H), 2.87 (t, J=6.9 Hz, 2H), 3.63-3.66 (m, 2H), 3.67 (s, 3H), 4.36 (q, J=7.2 Hz, 1H), 4.68 (s, 2H), 6.03 (br. s., 1H), 7.12-8.14 (m, 12H), 8.45 (s, 1H)

(4) The same procedure as used in Example 149-(4) was carried out using the compound (110 mg) obtained in Example 254-(3) to give the titled compound (58 mg) as a colorless solid.

Example 255

2-{1-[(4-{[2-(4-chlorophenyl)ethyl]carbamoyl}phenyl)carbonyl]isoquinolin-4-yl}-2-methylpropanoic acid (1) To a solution of the compound (181 mg) obtained in Example 135-(3) in N,N-dimethylformamide (3.6 ml), sodium hydride (38 mg) was added in an ice bath. The mixed solution was stirred for 10 min, and methyl iodide (0.058 ml) was added thereto, and the mixed solution was stirred for 1.5 hours. A saturated aqueous of ammonium chloride solution was added, followed by extraction with ethyl acetate. Then, the organic layer was dried over anhydrous magnesium sulfate, and evaporated under reduced pressure to remove the solvent. The resulting crude product was purified by column chromatography (neutral OH type silica gel, ethyl acetate/n-hexane=10 to 30%) to give tert-butyl 4-{[4-(1-methoxy-2-methyl-1-oxopropan-2-yl)isoquinolin-1-yl]carbonyl}benzoate (139 mg) as a colorless amorphous substance.
$^1$H NMR (600 MHz, CHLOROFORM-d) d ppm 1.61 (s, 9H), 1.84 (s, 6H), 3.63 (s, 3H), 7.59-8.31 (m, 8H), 8.65 (s, 1H)

(2) The same procedure as used in Example 153-(5) was carried out using the compound (139 mg) obtained in Example 255-(1) to give 4-{[4-(1-methoxy-2-methyl-1-oxopropan-2-yl)isoquinolin-1-yl]carbonyl}benzoic acid (128 mg) as a colorless amorphous substance.
$^1$H NMR (600 MHz, DMSO-$d_6$) d ppm 1.75 (s, 6H), 3.55 (s, 3H), 7.68-8.17 (m, 8H), 8.66 (s, 1H)

(3) The same procedure as used in Example 161-(1) was carried out using the compound (128 mg) obtained in Example 255-(2) to give methyl 2-{1-[(4-{[2-(4-chlorophenyl)ethyl]carbamoyl}phenyl)carbonyl]isoquinolin-4-yl}-2-methylpropanoate (73 mg) as a colorless amorphous substance.
$^1$H NMR (600 MHz, CHLOROFORM-d) d ppm 1.84 (s, 6H), 2.91-2.95 (m, 2H), 3.63 (s, 3H), 3.69-3.75 (m, 2H), 6.10-6.15 (m, 1H), 7.15-8.33 (m, 12H), 8.64 (s, 1H)

(4) To a solution of the compound (70 mg) obtained in Example 255-(3) in 1,4-dioxane (1.4 ml), 1N aqueous lithium hydroxide solution (1.4 ml) was added, and the mixed solution was stirred at 100° C. for one hour. The solution was adjusted to pH4 by adding 1N aqueous hydrochloric acid solution, and then extracted with ethyl acetate. The organic layer was washed with a saturated saline solution, dried over anhydrous magnesium sulfate, and evaporated under reduced pressure to remove the solvent. The resulting crude product was purified by column chromatography (acidic OH type silica gel, ethyl acetate/n-hexane=30 to 60%), diethyl ether was added thereto, and the resulting solution was stirred for 15 hours. The produced solid was filtered out to give the titled compound (21 mg) as a pale yellow solid.

Example 256

4-{[4-(2-amino-2-oxoethyl)isoquinolin-1-yl]methyl}-N-[2-(4-chlorophenyl)ethyl]benzamide To a suspension of the compound (400 mg) obtained in Example 153-(7) in tetrahydrofuran (9 ml), 1,1'-carbonyldiimidazole (283 mg) was added. The mixed solution was stirred at room temperature for two hours. Then, 28% aqueous ammonia (0.45 ml) was added thereto, and the resulting solution was stirred at room temperature for one hour. The precipitate was filtered out and dried to give the titled compound (384 mg) as a colorless solid.

Example 257

N-[2-(4-chlorophenyl)ethyl]-4-{[4-(1H-tetrazol-5-ylmethyl)isoquinolin-1-yl]methyl}benzamide (1) To the compound (362 mg) obtained in Example 256-(1), phosphoryl chloride (0.088 ml) was added, and the mixed solution was stirred at room temperature for one hour. To the reaction solution, ice water was added, followed by extraction with chloroform. Then, the organic layer was dried over anhydrous magnesium sulfate and evaporated under reduced pressure to remove the solvent. The resulting crude product was purified by column chromatography (neutral OH type silica gel, methanol/chloroform=2 to 10%) to give N-[2-(4-chlorophenyl)ethyl]-4-{[4-(cyanomethyl)isoquinolin-1-yl]methyl}benzamide (256 mg) as a pale yellow solid.
$^1$H NMR (600 MHz, DMSO-$d_6$) d ppm 2.80 (t, J=7.3 Hz, 2H), 3.40-3.47 (m, 2H), 4.45 (s, 2H), 4.70 (s, 2H), 7.20-8.44 (m, 13H), 8.49 (s, 1H)

(2) To a suspension of the compound (20 mg) obtained in Example 257-(1) in toluene (0.45 ml), sodium azide (9 mg) and triethylamine hydrochloride (19 mg) were added, and the mixture was refluxed for 72 hours. Methanol/chloroform (10%) was added thereto. The organic layer was washed with water, dried over anhydrous magnesium sulfate, and evaporated under reduced pressure to remove the solvent. The resulting crude product was purified by column chromatography (neutral OH type silica gel, methanol/chloroform=10 to 20%). To the resulting solid, methanol/chloroform (10%) was added, and the mixture was washed with 0.5; N aqueous hydrochloric acid solution, and then washed with water. The organic layer was dried over anhydrous magnesium sulfate and then evaporated under reduced pressure to remove the solvent to give the titled compound (3.1 mg) as a colorless solid.

Example 258

N-[2-(4-chlorophenyl)ethyl]-4-({4-[2-(hydroxyamino)-2-oxoethyl]isoquinolin-1-yl}methyl)benzamide (1) To a solution of the compound (41 mg) obtained in Example 153-(7), O-(tetrahydro-2H-pyran-2-yl)hydroxylamine (12 mg) and 1-hydroxybenzotriazole hydrate (15 mg) in N,N-dimethylformamide (2 ml), 1-ethyl-3-(dimethylaminopropyl)-carbodiimide hydrochloride (19 mg) was added, and the mixture solution was stirred at room temperature for one hour. Ethyl acetate was added, and the reaction solution was washed with water and then washed with a saturated saline solution. The organic layer was dried over anhydrous magnesium sulfate, and then evaporated under reduced pressure to remove the solvent. The resulting crude product was purified by column chromatography (neutral OH type silica gel, methanol/chloroform=0 to 20%) to give N-[2-(4-chlorophenyl)ethyl]-4-[(4-{2-oxo-2-[(tetrahydro-2H-pyran-2-yloxy)amino]ethyl}isoquinolin-1-yl)methyl]benzamide (49 mg) as a pale yellow solid.
$^1$H NMR (600 MHz, CHLOROFORM-d) d ppm 1.20-1.85 (m, 6H), 2.83-2.91 (m, 4H), 3.59-3.98 (m, 5H), 4.67 (s, 2H), 4.84-4.95 (m, 1H), 5.98-6.07 (m, 1H), 7.10-8.29 (m, 12H), 8.40 (s, 1H)

(2) To a solution of the compound (49 mg) obtained in Example 258-(1) in methanol (2 ml), 4 N hydrochloric acid-ethyl acetate (0.223 ml) was added in an ice bath, and the mixed solution was stirred at room temperature for three hours. Chloroform was added thereto, and the reaction solution was washed with water and then washed with a saturated saline solution. The organic layer was dried over anhydrous magnesium sulfate, and then evaporated under reduced pressure to remove the solvent. The resulting crude product was purified by column chromatography (neutral OH type silica gel, methanol/chloroform=2 to 20%) to give the titled compound (17 mg) as a pale yellow solid.

Example 259

{1-[(4-{[2-(4-chlorophenyl)ethyl]carbamoyl}phenyl)carbonyl]-6,7-dimethoxyisoquinolin-4-yl}acetic acid (1) To a solution of 4-(2-methoxy-2-oxoethyl)benzoic acid (1.00 g) in acetonitrile (50 ml), N,N-diisopropyl ethyl amine (2.63 ml), O-(7-azabenzotriazol-1-yl)-1,1,3,3-tetramethyluronium hexafluorophosphate (2.94 g) and 2-(4-chlorophenyl)ethylamine (790 ml) were added, and the mixed solution was stirred at room temperature for 16 hours. The solvent was removed by evaporation under reduced pressure, and the resulting crude product was purified by column chromatography (neutral OH type silica gel, ethyl acetate/n-hexane=30 to 50%) to give methyl (4-{[2-(4-chlorophenyl)ethyl]carbamoyl}phenyl)acetate (2.02 g).

$^1$H NMR (600 MHz, CHLOROFORM-d) d ppm 2.88-2.93 (m, 2H), 3.65-3.72 (m, 7H), 6.08-6.19 (m, 1H), 7.14-7.35 (m, 7H), 7.63-7.67 (m, 1H)

(2) The same procedure as used in Example 153-(3) was carried out using the compound (2.02 g) obtained in Example 259-(1) to give (4-{[2-(4-chlorophenyl)ethyl]carbamoyl}phenyl)acetic acid (1.78 g).

$^1$H NMR (600 MHz, CHLOROFORM-d) d ppm 2.88-2.93 (m, 2H), 3.67-3.72 (m, 4H), 6.09 (br. s., 1H), 7.15-7.67 (m, 8H)

(3) To a solution of the compound (250 mg) obtained in Example 259-(2) in N,N-dimethylformamide (8 ml), N,N-diisopropyl ethyl amine (0.401 ml), O-(7-azabenzotriazol-1-yl)-1,1,3,3-tetramethyluronium hexafluorophosphate (449 mg) and ethyl 4-amino-3-(3,4-dimethoxyphenyl)butanoate (231 mg) was added, and the mixed solution was stirred at room temperature for 15 hours. Ethyl acetate was added thereto, and the reaction solution was washed with water and then washed with a saturated saline solution. The solvent was removed by evaporation under reduced pressure, and the resulting crude product was purified by column chromatography (neutral OH type silica gel, ethyl acetate/n-hexane=30 to 75%) to give ethyl 4-{[(4-{[2-(4-chlorophenyl)ethyl]carbamoyl}phenyl)acetyl]amino}-3-(3,4-dimethoxyphenyl)butanoate (130 mg).

$^1$H NMR (600 MHz, CHLOROFORM-d) d ppm 1.11-1.20 (m, 3H), 2.49-4.10 (m, 19H), 5.18-5.24 (m, 1H), 6.30-6.36 (m, 1H), 6.51-7.57 (m, 11H)

(4) To a solution of the compound (130 mg) obtained in Example 259-(3) in chloroform (2.3 ml), 2-chloropyridine (0.026 ml) was added and cooled to −60° C., and then trifluoromethanesulfonic anhydride (0.042 ml) was added. The mixed solution was stirred for 5 min. The resulting solution was stirred for 5 min in an ice bath, and further stirred at room temperature for one hour. Saturated sodium bicarbonate water was added, followed by extraction with chloroform. The organic layer was dried over anhydrous sodium sulfate, and then evaporated under reduced pressure to remove the solvent. To the resulting crude product, sulfur (9 mg) was added, and the mixed solution was stirred at 165° C. for 15 min. Ethanol was added and insolubles were removed by filtration, and the solvent in the filtrate was removed by evaporation under reduced pressure. The resulting crude product was purified by column chromatography (neutral OH type silica gel, ethyl acetate/n-hexane=33 to 75%) to give ethyl {1-[(4-{[2-(4-chlorophenyl)ethyl]carbamoyl}phenyl)carbonyl]-6,7-dimethoxyisoquinolin-4-yl}acetate (30 mg).

$^1$H NMR (600 MHz, CHLOROFORM-d) d ppm 1.23-1.28 (m, 3H), 2.91-2.95 (m, 2H), 3.69-3.74 (m, 2H), 3.99 (s, 3H), 4.03 (s, 2H), 4.07 (s, 3H), 4.16-4.21 (m, 2H), 6.13-6.17 (m, 1H), 7.15-8.02 (m, 10H), 8.38 (s, 1H)

(5) The same procedure as used in Example 149-(4) was carried out using the compound (27 mg) obtained in Example 259-(4) to give the titled compound (7 mg) as a pale yellow solid.

Example 260

{1-[(4-{[2-(4-chlorophenyl)ethyl]carbamoyl}phenyl)carbonyl]-6-methoxyisoquinolin-4-yl}acetic acid (1) To a solution of ethyl 3-cyano-3-(3-methoxyphenyl)propanoate (11.9 g) in ethanol (41 ml), 12 N hydrochloric acid (3.8 ml) and 20% palladium hydroxide on carbon (2.10 g) was added, and the mixed solution was stirred in hydrogen atmosphere at room temperature for 15 hours. The solvent was removed by evaporation under reduced pressure, and resulting crude product was purified by column chromatography (neutral OH type silica gel, methanol/chloroform=2 to 9%) to give ethyl 4-amino-3-(3-methoxyphenyl)butanoate (3.80 g).

$^1$H NMR (600 MHz, CHLOROFORM-d) d ppm 1.11-1.16 (m, 3H), 2.65-2.72 (m, 1H), 2.79-2.86 (m, 1H), 3.06-3.12 (m, 1H), 3.24-3.30 (m, 1H), 3.46-3.53 (m, 1H), 3.76-3.79 (m, 3H), 4.00-4.07 (m, 2H), 6.76-7.26 (m, 4H)

(2) The same procedure as used in Example 153-(6) was carried out using the compound (280 mg) obtained in Example 260-(1) and the compound (250 mg) obtained in Example 259-(2) to give ethyl 4-{[(4-{[2-(4-chlorophenyl)ethyl]carbamoyl}phenyl)acetyl]amino}-3-(3-methoxyphenyl)butanoate (210 mg).

$^1$H NMR (600 MHz, CHLOROFORM-d) d ppm 1.12-1.18 (m, 3H), 2.52-2.61 (m, 2H), 2.90-2.95 (m, 2H), 3.18-3.32 (m, 2H), 3.48 (s, 2H), 3.58-3.64 (m, 1H), 3.68-3.73 (m, 2H), 3.74 (s, 3H), 4.01-4.07 (m, 2H), 5.25-5.30 (m, 1H), 6.14-6.19 (m, 1H), 6.57-7.60 (m, 12H)

(3) The same procedure as used in Example 259-(4) was carried out using the compound (201 mg) obtained in Example 260-(2) to give ethyl {1-[(4-{[2-(4-chlorophenyl)ethyl]carbamoyl}phenyl)carbonyl]-6-methoxyisoquinolin-4-yl}acetate (40 mg).

$^1$H NMR (600 MHz, CHLOROFORM-d) d ppm 1.26 (t, J=7.3 Hz, 3H), 2.90-2.95 (m, 2H), 3.69-3.73 (m, 2H), 3.99 (s, 3H), 4.04 (s, 2H), 4.20 (q, J=7.3 Hz, 2H), 6.12-6.16 (m, 1H), 7.15-8.24 (m, 11H), 8.44 (s, 1H)

(4) The same procedure as used in Example 149-(4) was carried out using the compound (37 mg) obtained in Example 260-(3) to give the titled compound (20 mg) as a pale yellow solid.

Example 261

[1-(4-{[2-(4-chlorophenyl)ethyl]carbamoyl}phenoxy)isoquinolin-4-yl]acetic acid (1) A suspension of N-[2-(4-chlorophenyl)ethyl]-4-hydroxy benzamide (605 mg) and 1-chloro-isoquinoline-4-carboxylic acid methyl ester (443 mg) and potassium carbonate (332 mg) in DMF (4 ml) was stirred at 60° C. for two hours.

Ethyl acetate was added thereto, and the reaction solution was washed with water, and then washed with a saturated saline solution. The organic layer was dried over anhydrous magnesium sulfate, and then evaporated under reduced pressure to remove the solvent. The resulting crude product was purified by column chromatography (NH type silica gel, chloroform/n-hexane=50 to 80%) to give methyl 1-(4-{[2-(4-chlorophenyl)ethyl]carbamoyl}phenoxy)isoquinoline-4-carboxylate (782 mg) as a colorless solid.

$^1$H NMR (600 MHz, CHLOROFORM-d) d ppm 2.93 (t, J=7.1 Hz, 2H), 3.70-3.76 (m, 2H), 3.98 (s, 3H), 6.10 (t, J=5.5 Hz, 1H), 7.15-8.52 (m, 11H), 8.72 (s, 1H), 9.01 (d, J=8.3 Hz, 1H)

(2) The same procedure as used in Example 152-(4) was carried out using the compound (782 mg) obtained in Example 261-(1) to give 1-(4-{[2-(4-chlorophenyl)ethyl]carbamoyl}phenoxy)isoquinoline-4-carboxylic acid (781 mg) as a colorless solid.

$^1$H NMR (600 MHz, DMSO-d$_6$) d ppm 2.87 (t, J=7.1 Hz, 2H), 3.48-3.54 (m, 2H), 7.26-9.01 (m, 14H)

(3) The same procedure as used in Example 152-(5) was carried out using the compound (350 mg) obtained in Example 261-(2) to give the titled compound (5 mg) as a colorless solid.

Structural formulae and NMR values of Examples 252 to 261 are shown in Tables 8-1 to 8-2.

TABLE 8-1

| Example | Structural formula | $^1$H NMR (d ppm) |
| --- | --- | --- |
| 252 | | $^1$H NMR (600 MHz, DMSO-d6) 3.94 (br. s., 2 H), 4.58 (s, 2 H), 5.14 (s, 2 H), 6.78-8.30 (m, 13 H) |
| 253 | | $^1$H NMR (600 MHz, DMSO-d6) 2.80 (t, J = 7.3 Hz, 2 H), 3.41-3.46 (m, 2 H), 4.05 (s, 2 H), 4.72 (s, 2 H), 7.19-8.54 (m, 13 H) |
| 254 | | $^1$H NMR (600 MHz, DMSO-d6) 1.55 (d, J = 7.3 Hz, 3 H), 2.77-2.83 (m, 2 H), 3.40-3.46 (m, 2 H), 4.39 (q, J = 7.3 Hz, 1 H), 4.67 (s, 2 H), 7.21-8.44 (m, 14 H) |
| 255 | | $^1$H NMR (600 MHz, DMSO-d6) 1.76 (s, 6 H), 2.83-2.89 (m, 2 H), 3.47-3.53 (m, 2 H), 7.24-8.77 (m, 14 H), 12.80 (br. s., 1 H) |
| 256 | | $^1$H NMR (600 MHz, DMSO-d6) 2.77-2.82 (m, 2 H), 3.40-3.45 (m, 2 H), 3.81 (s, 2 H), 4.66 (s, 2 H), 7.00-8.43 (m, 16 H) |

TABLE 8-1-continued
| Example | Structural formula | $^1$H NMR (d ppm) |
|---|---|---|
| 257 | 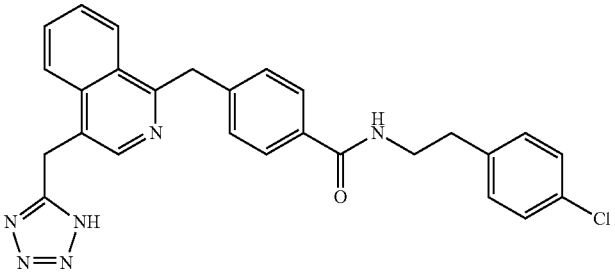 [SMILES: O=C(NCCc1ccc(Cl)cc1)c1ccc(Cc2ncc(Cc3nnn[nH]3)c3ccccc23)cc1] | $^1$H NMR (600 MHz, DMSO-d6) 2.77-2.82 (m, 2 H), 3.40-3.46 (m, 2 H), 4.69 (s, 2 H), 4.68 (s, 2 H), 7.21-8.45 (m, 14 H) |
| 258 | 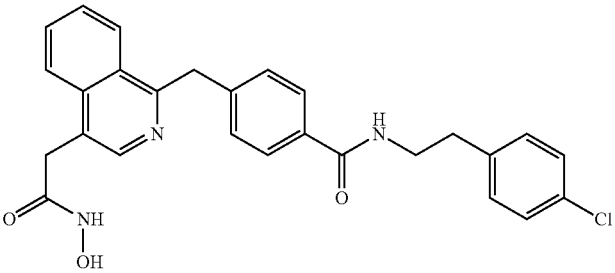 [SMILES: O=C(Cc1cnc(Cc2ccc(C(=O)NCCc3ccc(Cl)cc3)cc2)c2ccccc12)NO] | $^1$H NMR (600 MHz, DMSO-d6) 2.76-2.82 (m, 2 H), 3.39-3.46 (m, 2 H), 3.74 (s, 2 H), 4.66 (s, 2 H), 7.21-8.45 (m, 14 H), 8.87 (br. s., 1 H) |
TABLE 8-2
| Example | Structural formula | $^1$H NMR (d ppm) |
|---|---|---|
| 259 | 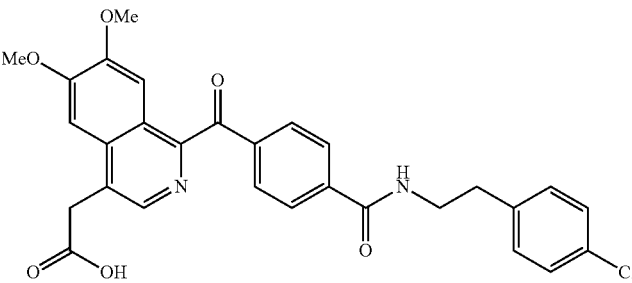 [SMILES: COc1cc2c(CC(=O)O)cnc(C(=O)c3ccc(C(=O)NCCc4ccc(Cl)cc4)cc3)c2cc1OC] | $^1$H NMR (600 MHz, DMSO-d6) 2.82-2.90 (m, 2 H), 3.46-3.54 (m, 2 H), 3.84 (s, 3 H), 3.87 (br. s., 2 H), 3.96 (s, 3 H), 7.23-8.82 (m, 12 H) |
| 260 | 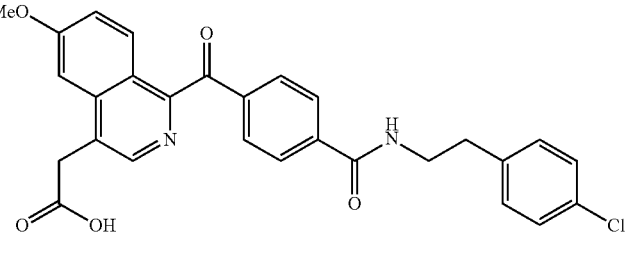 | $^1$H NMR (600 MHz, DMSO-d6) 2.81-2.89 (m, 2 H), 3.46-3.54 (m, 2 H), 3.95 (s, 3 H), 4.05 (br. s., 2 H), 7.23-8.79 (m, 13 H) |
| 261 | 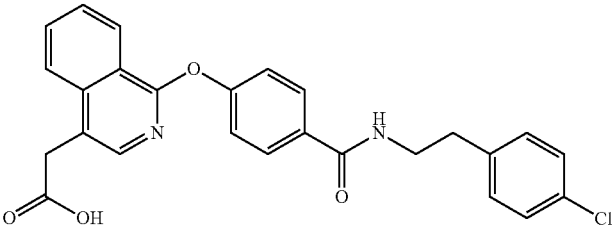 [SMILES: O=C(O)Cc1cnc(Oc2ccc(C(=O)NCCc3ccc(Cl)cc3)cc2)c2ccccc12] | $^1$H NMR (600 MHz, DMSO-d6) 2.87 (t, J = 7.1 Hz, 2 H), 3.46-3.55 (m, 2 H), 3.92 (s, 2 H), 7.26-8.91 (m, 14 H) |

Test Example 1

CRTH2 Binding Test

CRTH2 binding inhibitory activity of the compound of the present invention was considered by using a binding test between human CRTH2 expression cell KB8 (BML, INC.) and $^3$H-labeled prostaglandin D2 (hereinafter, abbreviated as $^3$H-PGD2, manufactured by GE Healthcare).

KB8 was suspended in a reaction buffer solution (Hank's balanced salt solution (Invitrogen) containing 10 mM HEPES (Invitrogen)), which was dispensed in a 96 well plate (Coaster) so that $2\times10^5$ cells/well are placed. Furthermore, the compound of the present invention and $^3$H-PGD2 (final concentration: 5 nM) were added, stirred, and incubated at 4° C.

One hour later, cells were collected on GF/C Filter Plate (PerkinElmer) that had been pre-coated with 0.5% polyethyleneimine solution (SIGMA) by using a Cell Harvester (Packard BioScience), and the radioactivity of the cells was measured by using Top count NXT (PerkinElmer) (a value measured herein was represented by a measurement value "a"). The same procedure was carried out in the absence of the compound, and a measurement value "b" was obtained; and the same procedure was carried out in the absence of the compound and in the presence of non-labeled PGD2 (final concentration: 50 μM), a measurement value "c" was obtained.

The binding inhibition rate of the compound was calculated by the following calculation formula:

Bonding inhibitory rate(%)=$[1-(a-c)/(b-c)]\times100$

Furthermore, the CRTH2 binding inhibitory activity of a compound to be tested was calculated as a value ($IC_{50}$ value) exhibiting 50% inhibitory activity with respect to the binding amount in the absence of the compound. That is to say, by using binding inhibition rates of compounds to be tested having various concentrations, the $IC_{50}$ value was calculated according to a dose-dependent inhibition curve analyzed by using XLfit (IDBS) as a data analysis software, and the calculated value was defined as an indicator of the inhibitory activity. The test results are shown in Table 9. In Table 9, A denotes an inhibitory activity showing the $IC_{50}$ value of less than 50 nM; B denotes an inhibitory activity showing the $IC_{50}$ value of 50 nM or greater and less than 500 nM; C denotes an inhibitory activity showing the $IC_{50}$ value of 500 nM or greater and less than 1000 nM; and D denotes an inhibitory activity showing the $IC_{50}$ value of 1000 nM or greater. Specific values include, for example, Example 18 ($IC_{50}$ value; 3.5 nM), Example 57 ($IC_{50}$ value; 3.4 nM), Example 75 ($IC_{50}$ value; 2.9 nM), Example 82 ($IC_{50}$ value; 2.8 nM) and Example 143 ($IC_{50}$ value; 9.9 nM).

TABLE 9

| Example | binding inhibitory activity |
| --- | --- |
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | B |
| 20 | A |
| 21 | A |
| 22 | A |
| 23 | A |
| 27 | A |
| 29 | A |
| 34 | A |
| 50 | A |
| 57 | A |
| 75 | A |
| 82 | A |
| 83 | A |
| 92 | A |
| 127 | B |
| 128 | B |
| 129 | B |
| 130 | A |
| 131 | A |
| 132 | A |
| 133 | A |
| 134 | A |
| 135 | A |
| 136 | A |
| 137 | A |
| 138 | A |
| 139 | A |
| 141 | A |
| 142 | A |
| 143 | A |
| 144 | B |
| 148 | A |
| 153 | A |

Test Example 2

CRTH2 Antagonist Test

The antagonist activity of the compound of the present invention was considered by using the intracellular calcium ion concentration increase reaction induced when the prostaglandin D2 was added to KB8 cells.

Fluo-4-AM (4-(6-acetoxymethoxy-2,7-difluoro-3-oxo-9-xanthenyl)-4'-methyl-2,2'-(ethylenedioxy)dianilide-N,N,N', N'-tetraacetic acid tetrakis(acetoxymethyl) ester (SIGMA, final concentration: 1 μM) was added to KB8 cells, and the cells were incubated at 37° C. for 30 min, washed with phosphate buffer (Invitrogen), and then suspended in Hank's balanced salt solution (Invitrogen)) containing a reaction buffer solution (10 mM HEPES (Invitrogen), and 1 mM calcium chloride (SIGMA). The suspension was dispensed in a 96 well plate (Nunc) so that $2\times10^5$ cells/well were placed, and the compound of the present invention and PGD2 (final concentration: 100 nM) were added. The fluorescence intensity thereof was measured over time by using FDSS6000 (Hamamatsu Photonics), and thus the maximum fluorescence intensity value "d" was obtained. The same procedure was carried out in the absence of the compound, and the maximum fluorescence intensity value "e" was obtained; and the same procedure was carried out in the absence of the compound and in the presence of non-labeled PGD2, and the maximum fluorescence intensity value "f" was obtained.

The calcium ion concentration increase inhibition rate of a compound was calculated by the following calculation formula:

$$\text{Inhibitory rate}(\%) = [1-(d-f)/(e-f)] \times 100$$

Furthermore, the CRTH2 antagonist activity of a compound to be tested was calculated as a value ($IC_{50}$ value) exhibiting 50% inhibitory activity with respect to the calcium ion concentration increase in the absence of the compound. That is to say, by using calcium ion concentration increase inhibitory rates of compounds to be tested having various concentrations, the $IC_{50}$ value was calculated according to a dose-dependent inhibition curve analyzed by using XLfit (IDBS) as a data analysis software, and the value was defined as an indicator of the antagonist activity. The test results are shown in Tables 10-1 and 10-2. In Tables, A denotes an inhibitory activity showing the $IC_{50}$ value of less than 50 nM; B denotes an inhibitory activity showing the $IC_{50}$ value of 50 nM or greater and less than 500 nM; C denotes an inhibitory activity showing the $IC_{50}$ value of 500 nM or greater and less than 1000 nM; and D denotes an inhibitory activity showing the $IC_{50}$ value of 1000 nM or greater. Specific values include, for example, Example 122 ($IC_{50}$ value; 2.3 nM), Example 153 ($IC_{50}$ value; 12 nM), Example 201 ($IC_{50}$ value; 20 nM), Example 234 ($IC_{50}$ value; 5.9 nM), and Example 240 ($IC_{50}$ value; 6.6 nM).

TABLE 10-1

| Example | antagonist activity |
| --- | --- |
| 1 | B |
| 2 | A |
| 3 | A |
| 4 | A |
| 5 | B |
| 6 | A |
| 7 | A |
| 8 | A |
| 9 | B |
| 10 | A |
| 11 | A |
| 12 | A |
| 13 | D |
| 14 | A |
| 15 | A |
| 17 | A |
| 18 | A |
| 21 | B |
| 22 | B |
| 23 | A |
| 24 | D |
| 25 | D |
| 26 | B |
| 27 | A |
| 28 | A |
| 29 | A |
| 30 | C |
| 31 | A |
| 32 | A |
| 33 | D |
| 34 | A |
| 35 | A |
| 36 | D |
| 37 | A |
| 38 | A |
| 39 | C |
| 40 | D |
| 41 | B |
| 42 | C |
| 43 | B |
| 44 | B |
| 45 | B |
| 46 | B |
| 47 | C |
| 48 | D |
| 49 | D |
| 50 | A |
| 51 | D |
| 52 | B |
| 53 | B |
| 54 | A |
| 55 | C |
| 56 | B |
| 57 | A |
| 58 | D |
| 59 | B |
| 60 | B |
| 61 | B |
| 62 | B |
| 63 | B |
| 64 | A |
| 65 | C |
| 66 | D |
| 67 | B |
| 68 | B |
| 69 | D |
| 70 | B |
| 71 | B |
| 72 | A |
| 73 | A |
| 74 | B |
| 75 | A |
| 76 | B |
| 77 | A |
| 78 | A |
| 79 | D |
| 80 | B |
| 81 | D |
| 82 | A |
| 83 | A |
| 84 | A |
| 85 | A |
| 86 | B |
| 87 | B |
| 88 | A |
| 89 | A |
| 90 | B |
| 91 | A |
| 92 | A |
| 93 | A |
| 94 | A |
| 95 | B |
| 96 | A |
| 97 | D |
| 98 | D |
| 99 | A |
| 100 | A |
| 101 | A |
| 102 | A |
| 103 | A |
| 104 | D |
| 105 | C |
| 106 | B |
| 107 | A |
| 108 | A |
| 109 | B |
| 110 | A |
| 111 | A |
| 112 | A |
| 113 | A |
| 114 | A |
| 115 | A |
| 116 | A |
| 117 | C |
| 118 | C |
| 119 | A |
| 120 | A |
| 121 | B |
| 122 | A |
| 123 | A |
| 124 | C |
| 125 | C |

TABLE 10-1-continued

| Example | antagonist activity |
|---|---|
| 126 | A |
| 130 | A |
| 131 | A |
| 132 | B |
| 133 | A |
| 134 | B |
| 135 | A |
| 136 | A |
| 137 | A |
| 138 | A |
| 139 | A |
| 140 | A |
| 141 | B |
| 142 | B |
| 143 | B |
| 145 | D |
| 146 | B |
| 147 | D |
| 148 | A |
| 149 | C |
| 150 | B |
| 151 | B |
| 152 | B |
| 153 | A |
| 154 | B |
| 155 | A |
| 156 | B |
| 157 | A |

TABLE 10-2

| Example | antagonist activity |
|---|---|
| 158 | A |
| 159 | A |
| 160 | A |
| 161 | B |
| 162 | A |
| 163 | A |
| 164 | A |
| 165 | A |
| 166 | A |
| 167 | A |
| 168 | B |
| 169 | B |
| 170 | B |
| 171 | B |
| 172 | B |
| 173 | D |
| 174 | B |
| 175 | D |
| 176 | D |
| 177 | D |
| 178 | B |
| 179 | A |
| 180 | A |
| 181 | B |
| 182 | B |
| 183 | A |
| 184 | B |
| 185 | D |
| 186 | C |
| 187 | A |
| 188 | B |
| 189 | D |
| 190 | B |
| 191 | B |
| 192 | A |
| 193 | A |
| 194 | A |
| 195 | A |
| 196 | C |
| 197 | B |
| 198 | B |
| 199 | A |

TABLE 10-2-continued

| Example | antagonist activity |
|---|---|
| 200 | B |
| 201 | A |
| 202 | B |
| 203 | A |
| 204 | A |
| 205 | A |
| 206 | B |
| 207 | D |
| 208 | A |
| 209 | D |
| 210 | A |
| 211 | B |
| 212 | B |
| 213 | B |
| 214 | D |
| 215 | B |
| 216 | B |
| 217 | A |
| 218 | A |
| 219 | B |
| 220 | D |
| 221 | A |
| 222 | A |
| 223 | B |
| 224 | B |
| 225 | A |
| 226 | A |
| 227 | D |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | B |
| 240 | A |
| 241 | A |
| 242 | A |
| 243 | A |
| 244 | A |
| 245 | A |
| 246 | B |
| 247 | B |
| 248 | B |
| 249 | A |
| 250 | A |
| 251 | B |
| 252 | D |
| 253 | A |
| 254 | C |
| 255 | D |
| 256 | D |
| 257 | D |
| 258 | D |
| 259 | B |
| 260 | B |
| 261 | D |

INDUSTRIAL APPLICABILITY

A compound of the present invention has a CRTH2 inhibitory activity, and can be used as preventive agents or therapeutic agents for allergic diseases such as asthma, atopic dermatitis, and allergic rhinitis.

The invention claimed is:
1. A compound represented by formula (I):

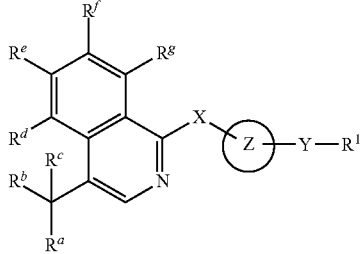

(I)

wherein $R^1$ represents a $C_{1-6}$ alkyl group, a $C_{2-6}$ alkenyl group, a $C_{3-6}$ cycloalkyl group, a $C_{3-6}$ cycloalkenyl group, an adamantyl group, an indanyl group, a tetrahydronaphthyl group, a tetrahydroindolyl group, a tetrahydropyranyl group, a morpholinyl group, a phenyl group, a naphthyl group, or an aromatic heterocyclic group, wherein the phenyl group, the naphthyl group, and the aromatic heterocyclic group may be substituted with 1 to 5 substituent(s) selected from the group consisting of a $C_{1-6}$ alkyl group, a $C_{2-6}$ alkenyl group, a $C_{3-6}$ cycloalkyl group, a halogen atom, a $C_{1-6}$ alkoxy group, a hydroxy group, a $C_{1-6}$ alkylthio group, a $C_{1-6}$ haloalkyl group, a $C_{1-6}$ haloalkoxy group, a $C_{1-6}$ haloalkylthio group, a cyano group, a nitro group, a guanidino group, a $C_{1-6}$ alkylsulfonyl group, a carboxy group, a $C_{2-7}$ alkoxycarbonyl group, a $C_{2-7}$ alkanoyloxy group, a phenyl group, a benzoyl group, a phenoxy group, a pyrrolyl group, a thienyl group, an imidazolyl group, a thiadiazolyl group, a morpholino group, the formula: —$NR^5R^6$, the formula: —$SO_2NR^7R^8$, the formula: —$NR^9SO_2R^{10}$, the formula: —$CONR^{11}R^{12}$, and the formula: —$NR^{13}COR^{14}$, wherein $R^5$, $R^6$, $R^7$, $R^8$, $R^9$, $R^{10}$, $R^{11}$, $R^{12}$, $R^{13}$, and $R^{14}$ each independently represent a hydrogen atom or a $C_{1-6}$ alkyl group;

X represents an oxygen atom, a sulfur atom, the formula: —$CH_2$—, the formula: —CO—, or the formula: —$NR^2$—, wherein $R^2$ represents a hydrogen atom or a $C_{1-6}$ alkyl group;

Y represents a single bond, the formula: —$NR^3CO$—W—, the formula: —$NR^3CO$—W—O—, the formula: —$NR^3CO_2$—W—, the formula: —$NR^3$—W—, the formula: —$NR^3SO_2$—W—, the formula: —$NR^3CONR^4$—W—, the formula: —$NR^3CO$—W—$NR^4SO_2$—, the formula: —$SO_2NR^3$—W—, the formula: —$CH_2$—W—, the formula: —$CONR^3$—W—, the formula: —$CONR^3$—W—O—, the formula: —$CH_2$—O—W—, the formula: —$CH_2NR^3$—W—, the formula: —$CONR^3$—W—$NR^4CO$—, the formula: —O—W—, or the formula: —O—W—O—, wherein $R^3$ and $R^4$ each independently represent a hydrogen atom or a $C_{1-6}$ alkyl group, W is a single bond, a $C_{1-6}$ alkylene group, a $C_{2-6}$ alkylene group including a carbon atom that is also a member of a $C_{3-6}$ cycloalkyl ring, a $C_{2-6}$ alkenylene group, or a $C_{3-6}$ cycloalkylene group (provided that, when Y is the formula: —$CONR^3$—W—$NR^4CO$— or the formula: —O—W—O—, W is not a single bond);

Z represents a benzene ring, a pyrimidine ring, or a pyrazine ring;

$R^a$ represents a carboxy group, a carbamoyl group, a tetrazolyl group, or the formula: —CONHOH;

$R^b$ and $R^c$ each independently represent a hydrogen atom, a halogen atom, or a $C_{1-6}$ alkyl group; and $R^d$, $R^e$, $R^f$ and $R^g$ each independently represent a hydrogen atom, a halogen atom, a $C_{1-6}$ alkyl group, or a $C_{1-6}$ alkoxy group (provided that the compound is not {1-[3-(butan-2-yloxy)benzyl]-6,7-dimethoxyisoquinolin-4-yl}acetic acid, (1-{[3-(butan-2-yl)phenyl]carbonyl}-6,7-dimethoxyisoquinolin-4-yl)acetic acid, (1-{[3-(butan-2-yloxy)phenyl]carbonyl}-6,7-dimethoxyisoquinolin-4-yl)acetic acid, 2-(6,7-dimethoxy-1-{[3-(propan-2-yloxy)phenyl]carbonyl}isoquinolin-4-yl)acetamide, (6,7-dimethoxy-1-{[3-(propan-2-yloxy)phenyl]carbonyl}isoquinolin-4-yl)acetic acid, 2-{6,7-dimethoxy-1-[(3-methoxyphenyl)carbonyl]isoquinolin-4-yl}acetamide, or {6,7-dimethoxy-1-[(3-methoxyphenyl)carbonyl]isoquinolin-4-yl}acetic acid);

or a pharmaceutically acceptable salt thereof.

2. The compound or a pharmaceutically acceptable salt thereof according to claim 1, wherein $R^d$, $R^e$, $R^f$ and $R^g$ each independently represent a hydrogen atom, a halogen atom, a $C_{1-6}$ alkyl group, or a $C_{1-6}$ alkoxy group (except the compound or a pharmaceutically acceptable salt thereof in which both $R^d$ and $R^g$ are hydrogen atoms and both $R^e$ and $R^f$ are $C_{1-6}$ alkoxy groups).

3. The compound or a pharmaceutically acceptable salt thereof according to claim 1, wherein $R^1$ is a $C_{1-6}$ alkyl group, a $C_{2-6}$ alkenyl group, a $C_{3-6}$ cycloalkyl group, a $C_{3-6}$ cycloalkenyl group, an adamantyl group, an indanyl group, a tetrahydronaphthyl group, a tetrahydroindolyl group, a tetrahydropyranyl group, a morpholinyl group, a phenyl group, a naphthyl group, or an aromatic heterocyclic group, wherein the phenyl group, the naphthyl group, and the aromatic heterocyclic group may be substituted with 1 to 5 substituent(s) selected from the group consisting of a $C_{1-6}$ alkyl group, a $C_{2-6}$ alkenyl group, a $C_{3-6}$ cycloalkyl group, a halogen atom, a $C_{1-6}$ alkoxy group, a hydroxy group, a $C_{1-6}$ haloalkyl group, a $C_{1-6}$ haloalkoxy group, a cyano group, a nitro group, a $C_{1-6}$ alkylsulfonyl group, a carboxy group, a phenyl group, a benzoyl group, a phenoxy group, the formula: —$NR^5R^6$, and the formula: —$SO_2NR^7R^8$;

X is an oxygen atom, the formula: —$CH_2$—, or the formula: —CO—;

Z is a benzene ring;

$R^a$ is a carboxy group, a carbamoyl group, a tetrazolyl group, or the formula: —CONHOH;

$R^b$ and $R^c$ each independently represent a hydrogen atom, or a $C_{1-6}$ alkyl group; and $R^d$, $R^e$, $R^f$ and $R^g$ each independently represent a hydrogen atom, a halogen atom, or a $C_{1-6}$ alkoxy group.

4. The compound or a pharmaceutically acceptable salt thereof according to claim 1, wherein $R^1$ is a $C_{1-6}$ alkyl group, a $C_{3-6}$ cycloalkyl group, a phenyl group, a naphthyl group, or an aromatic heterocyclic group, wherein the phenyl group, the naphthyl group, and the aromatic heterocyclic group may be substituted with 1 to 3 substituent(s) selected from the group consisting of a $C_{1-6}$ alkyl group, a halogen atom, a $C_{1-6}$ alkoxy group, a hydroxy group, a $C_{1-6}$ alkylthio group, a $C_{1-6}$ haloalkyl group, a $C_{1-6}$ haloalkoxy group, a $C_{1-6}$ haloalkylthio group, a cyano group, a nitro group, a guanidino group, a $C_{1-6}$ alkylsulfonyl group, a carboxy group, a $C_{2-7}$ alkoxycarbonyl group, a $C_{2-7}$ alkanoyloxy group, a phenyl group, a phenoxy group, a pyrrolyl group, a thienyl group, an imidazolyl group, a thiadiazolyl group, a morpholino group, the formula: —NR$^5$R$^6$, the formula: —SO$_2$NR$^7$R$^8$, the formula: —NR$^9$SO$_2$R$^{10}$, the formula: —CONR$^{11}$R$^{12}$, and the formula: —NR$^{13}$COR$^{14}$;

Y is a single bond, the formula: —NR$^3$CO—W—, the formula: —NR$^3$CO—W—O—, the formula: —NR$^3$CO$_2$—W—, the formula: —NR$^3$—W—, the formula: —NR$^3$SO$_2$—W—, the formula: —NR$^3$CONR$^4$—W—, the formula: —CONR$^3$—W—, the formula: —O—W—, the formula: —CH$_2$O—, or the formula: —CH$_2$NR$^3$—;

W is a single bond, a C$_{1-6}$ alkylene group, a C$_{2-6}$ alkenylene group, or a C$_{3-6}$ cycloalkylene group;

R$^a$ is a carboxy group;

R$^b$ and R$^c$ are each a hydrogen atom, and

R$^d$, R$^e$, R$^f$ and R$^g$ are each a hydrogen atom.

5. The compound or a pharmaceutically acceptable salt thereof according to claim 1, wherein R$^1$ is a C$_{1-6}$ alkyl group, a C$_{3-6}$ cycloalkyl group, a phenyl group, a naphthyl group, or an aromatic heterocyclic group, wherein the phenyl group, the naphthyl group, and the aromatic heterocyclic group may be substituted with 1 to 3 substituent(s) selected from the group consisting of a C$_{1-6}$ alkyl group, a halogen atom, a C$_{1-6}$ alkoxy group, a C$_{1-6}$ haloalkyl group, a C$_{1-6}$ haloalkoxy group, a cyano group, a nitro group, a phenyl group, a phenoxy group, and the formula: —NR$^5$R$^6$;

X is the formula: —CH$_2$—, or the formula: —CO—;

Y is the formula: —NR$^3$CO—W—, the formula: —NR$^3$CO—W—O—, the formula: —NR$^3$CO$_2$—W—, the formula: —NR$^3$—W—, the formula: —NR$^3$SO$_2$—W—, the formula: —NR$^3$CONR$^4$—W—, or the formula: —O—W—;

W is a single bond, a C$_{1-6}$ alkylene group, a C$_{2-6}$ alkenylene group, or a C$_{3-6}$ cycloalkylene group;

Z is a benzene ring;

R$^a$ is a carboxy group;

R$^b$ and R$^c$ are each a hydrogen atom, and

R$^d$, R$^e$, R$^f$ and R$^g$ are each a hydrogen atom.

6. The compound or a pharmaceutically acceptable salt thereof according to claim 1, which is represented by formula (II):

[Ka 2]

(II)

wherein,

R$^{1'}$ is a C$_{3-6}$ cycloalkyl group, a C$_{3-6}$ cycloalkenyl group, an adamantyl group, an indanyl group, a tetrahydronaphthyl group, a tetrahydroindolyl group, a phenyl group, a naphthyl group, or an aromatic heterocyclic group, wherein the phenyl group, the naphthyl group, and the aromatic heterocyclic group may be substituted with 1 to 5 substituent(s) selected from the group consisting of a C$_{1-6}$ alkyl group, a C$_{2-6}$ alkenyl group, a C$_{3-6}$ cycloalkyl group, a halogen atom, a C$_{1-6}$ alkoxy group, a hydroxy group, a C$_{1-6}$ haloalkyl group, a C$_{1-6}$ haloalkoxy group, a cyano group, a nitro group, a C$_{1-6}$ alkylsulfonyl group, a phenyl group, a benzoyl group, a phenoxy group, the formula: —NR$^5$R$^6$, and the formula: —SO$_2$NR$^7$R$^8$, wherein R$^5$, R$^6$, R$^7$, and R$^8$ each independently represent a hydrogen atom or a C$_{1-6}$ alkyl group;

X' is the formula: —CH$_2$—, or the formula: —CO—; and

W' is a single bond, a C$_{1-6}$ alkylene group, a C$_{2-6}$ alkenylene group, or a C$_{3-6}$ cycloalkylene group.

7. The compound or a pharmaceutically acceptable salt thereof according to claim 6, wherein R$^{1'}$ is a C$_{3-6}$ cycloalkyl group, a tetrahydronaphthyl group, a tetrahydroindolyl group, a phenyl group, a naphthyl group, an indolyl group, a benzofuranyl group, a benzothienyl group, a quinolyl group, or an isoquinolyl group, wherein the phenyl group, the naphthyl group, the indolyl group, the benzofuranyl group, the benzothienyl group, the quinolyl group, and the isoquinolyl group may be substituted with 1 to 3 substituent(s) selected from the group consisting of a C$_{1-6}$ alkyl group, a halogen atom, a C$_{1-6}$ alkoxy group, a C$_{1-6}$ haloalkyl group, a C$_{1-6}$ haloalkoxy group, a cyano group, a nitro group, a phenyl group, a phenoxy group, and the formula: —NR$^5$R$^6$.

8. The compound or a pharmaceutically acceptable salt thereof according to claim 6, wherein R$^{1'}$ is a phenyl group, which may be substituted with 1 to 3 substituent(s) selected from the group consisting of a C$_{1-6}$ alkyl group, a halogen atom, a C$_{1-6}$ alkoxy group, a C$_{1-6}$ haloalkyl group, a C$_{1-6}$ haloalkoxy group, a cyano group, a nitro group, a phenyl group, a phenoxy group, and the formula: —NR$^5$R$^6$; and W' is a single bond.

9. The compound or a pharmaceutically acceptable salt thereof according to claim 6, wherein X' is the formula: —CH$_2$—.

10. The compound or a pharmaceutically acceptable salt thereof according to claim 8, wherein X' is the formula: —CO—.

11. The compound or a pharmaceutically acceptable salt thereof according to claim 1, which is represented by formula (III):

[Ka 3]

(III)

wherein,

R$^{1''}$ is a C$_{3-6}$ cycloalkyl group, a C$_{3-6}$ cycloalkenyl group, an adamantyl group, a tetrahydronaphthyl group, a tetrahydroindolyl group, a phenyl group, a naphthyl group, or an aromatic heterocyclic group, wherein the phenyl group, the naphthyl group, and the aromatic heterocyclic group may be substituted with 1 to 5 substituent(s) selected from the group consisting of a C$_{1-6}$ alkyl group, a C$_{3-6}$ cycloalkyl group, a halogen atom, a C$_{1-6}$ alkoxy group, a hydroxy group, a C$_{1-6}$ haloalkyl group, a C$_{1-6}$ haloalkoxy group, a cyano group, a nitro group, a phenyl group, a phenoxy group, and the formula: —NR$^5$R$^6$;

$R^5$ and $R^6$ each independently represent a hydrogen atom or a $C_{1-6}$ alkyl group;

X" is the formula: —$CH_2$—, or the formula: —CO—; and

W" is a single bond, a $C_{2-6}$ alkylene group including a carbon atom that is also a member of a $C_{3-6}$ cycloalkyl ring, or a $C_{1-6}$ alkylene group.

12. The compound or a pharmaceutically acceptable salt thereof according to claim 11, wherein $R^{1''}$ is a $C_{3-6}$ cycloalkyl group, an adamantyl group, a tetrahydronaphthyl group, a phenyl group, a naphthyl group, an indolyl group, a benzothiazolyl group, a benzofuranyl group, or a benzothienyl group, wherein the phenyl group, the naphthyl group, the indolyl group, benzothiazolyl group, the benzofuranyl group, and the benzothienyl group may be substituted with 1 to 3 substituent(s) selected from the group consisting of a $C_{1-6}$ alkyl group, a $C_{3-6}$ cycloalkyl group, a halogen atom, a $C_{1-6}$ alkoxy group, a $C_{1-6}$ haloalkyl group, a $C_{1-6}$ haloalkoxy group, a phenyl group, and a phenoxy group.

13. The compound or a pharmaceutically acceptable salt thereof according to claim 11, wherein X" is the formula: —$CH_2$—.

14. The compound or a pharmaceutically acceptable salt thereof according to claim 11, wherein W" is a $C_{1-6}$ alkylene group.

* * * * *